US008114962B2

(12) United States Patent
Weininger et al.

(10) Patent No.: US 8,114,962 B2
(45) Date of Patent: *Feb. 14, 2012

(54) METHOD OF DETECTION OF NUCLEIC ACIDS WITH A SPECIFIC SEQUENCE COMPOSITION

(75) Inventors: Susan Weininger, Seattle, WA (US); Arthur M. Weininger, Seattle, WA (US)

(73) Assignee: The Gene Pool, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/493,877

(22) Filed: Jun. 29, 2009

(65) Prior Publication Data

US 2010/0113344 A1   May 6, 2010

Related U.S. Application Data

(63) Continuation of application No. 10/407,543, filed on Apr. 3, 2003, now abandoned, which is a continuation of application No. 08/860,844, filed as application No. PCT/US95/15944 on Dec. 7, 1995, now abandoned, said application No. 08/860,844 is a continuation-in-part of application No. 08/353,476, filed on Dec. 9, 1994, now Pat. No. 5,871,902.

(51) Int. Cl.
A61K 38/16 (2006.01)
G01N 33/53 (2006.01)
(52) U.S. Cl. .......................................... 530/358; 435/7.1
(58) Field of Classification Search .......................... None
See application file for complete search history.

(56) References Cited

U.S. PATENT DOCUMENTS

| | | |
|---|---|---|
| 4,556,643 A | 12/1985 | Paau et al. |
| 4,623,627 A | 11/1986 | Huang et al. |
| 4,683,195 A | 7/1987 | Mullis et al. |
| 4,724,202 A | 2/1988 | Dattagupta et al. |
| 4,751,177 A | 6/1988 | Stabinsky |
| 4,775,619 A | 10/1988 | Urdea |
| 4,777,129 A | 10/1988 | Dattagupta et al. |
| 4,794,075 A | 12/1988 | Ford et al. |
| 4,868,105 A | 9/1989 | Urdea et al. |
| 4,882,269 A | 11/1989 | Schneider et al. |
| 4,948,882 A | 8/1990 | Ruth |
| 4,960,691 A | 10/1990 | Gordon et al. |
| 5,096,815 A | 3/1992 | Ladner et al. |
| 5,118,605 A | 6/1992 | Urdea |
| 5,122,600 A | 6/1992 | Kawaguchi et al. |
| 5,124,246 A | 6/1992 | Urdea et al. |
| 5,198,346 A | 3/1993 | Ladner et al. |
| 5,200,314 A | 4/1993 | Urdea |
| 5,215,882 A | 6/1993 | Bahl et al. |
| 5,215,899 A | 6/1993 | Dattagupta |
| 5,290,677 A | 3/1994 | Robertson et al. |
| 5,306,614 A | 4/1994 | Alizon et al. |
| 5,306,619 A | 4/1994 | Edwards et al. |
| 5,310,650 A | 5/1994 | McMahon et al. |
| 5,314,809 A | 5/1994 | Erlich et al. |
| 5,324,829 A | 6/1994 | Bahl et al. |
| 5,459,039 A | 10/1995 | Modrich et al. |
| 5,556,750 A | 9/1996 | Modrich et al. |
| 5,593,834 A | 1/1997 | Lane et al. |
| 5,668,255 A | 9/1997 | Murphy |
| 5,674,980 A | 10/1997 | Frankel et al. |
| 5,679,522 A | 10/1997 | Modrich et al. |
| 5,830,458 A | 11/1998 | Gruber et al. |
| 5,871,902 A * | 2/1999 | Weininger et al. ................ 435/5 |
| 5,882,941 A | 3/1999 | Essigmann et al. |
| 6,017,524 A | 1/2000 | Roth et al. |
| 2003/0059767 A1 | 3/2003 | Barbas, III et al. |

FOREIGN PATENT DOCUMENTS

| | | |
|---|---|---|
| EP | 0 146 039 | 6/1985 |
| EP | 0 147 665 | 7/1985 |
| EP | 0 204 510 | 12/1986 |
| EP | 0 357 336 | 3/1990 |
| EP | 0 450 594 | 10/1991 |
| EP | 0 453 301 | 10/1991 |
| EP | 0 593 789 | 4/1994 |
| JP | 5-308999 | 11/1993 |
| JP | 10-510157 | 10/1998 |
| WO | WO 87/03622 | 6/1987 |
| WO | WO 88/06601 | 9/1988 |

(Continued)

OTHER PUBLICATIONS

Jones et al. Sp1 binds to promoter sequences and activates herpes simplex virus "immediate early" gene transcription in vitro. Nature, vol. 317, pp. 179-182 (1985).*
Letovsky et al. Measurement of the binding of transcription factor Sp1 to a single GC box rercognition sequence. Nucleic Acids Research, vol. 17, pp. 2639-2653 (1989).*
Kattar-Cooley et al. Characterization of the DNA-Binding Properties of Herpes Simplex Virus Regulatory Protein ICP4. Journal of Virology, vol. 63, pp. 696-704 (1989).*
Gu et al. Herpes simplex virus infected cell polypeptide 4 preferentially represses Sp1-activated over basal transcription from its own promoter. Proceedings of the National Academy of Sciences USA vol. 90, pp. 9528-9532 (1993).*

(Continued)

*Primary Examiner* — John S Brusca
(74) *Attorney, Agent, or Firm* — Saliwanchik, Lloyd & Eisenschenk

(57) ABSTRACT

This invention is a novel method for detecting and localizing specific nucleic acid sequences in a sample with a high degree of sensitivity and specificity. The method and novel compositions used in the method involve the use of Probe Nucleic Acids, the production of nucleic acid binding regions and the use of nucleic acid Target Binding Assemblies to detect and localize specific Target Nucleic Acids. The detection and localization of the Target Nucleic Acid is accomplished even in the presence of nucleic acids which have similar sequences. The method provides for a high degree of amplification of the signal produced by each specific binding event. In particular, methods and compositions are presented for the detection of HIV and HPV nucleic acid in samples. These methods and compositions find use in diagnosis of disease, genetic monitoring, forensics, and analysis of nucleic acid mixtures. Some of the novel compositions used in the detection method are useful in preventing or treating pathogenic conditions.

9 Claims, 29 Drawing Sheets

FOREIGN PATENT DOCUMENTS

| | | |
|---|---|---|
| WO | WO 91/06679 | 5/1991 |
| WO | WO 92/20698 | 11/1992 |
| WO | WO 93/00446 | 1/1993 |
| WO | WO 93/15226 | 8/1993 |
| WO | WO 93/20233 | 10/1993 |
| WO | WO 94/17087 | 8/1994 |
| WO | WO 96/17956 | 6/1996 |

OTHER PUBLICATIONS

"Branch a good antisense molecule is hard to fiind", *Trends in Biochem. Sci.*, 1998, vol. 23, pp. 45-50.

American Society of Clinical Pathologists. "The Abott IMx" *Laboratory Med.* (1989), 20(1):47-49.

Anderson, W.F. et al., "Structure of the cro repressor fram bacteriophage λ and its interaction with DNA" *Nature* (1981), 290:754-758.

Antoni, B.A., et al., "$NF_\kappa B$-Dependent and—Independent pathways of HIV Activation in a Chronically Infected T Cell Line" *Virol.* (1994), 202:684-694.

Arya, S.K. et al., "*Trans*-Activator Gene of Human T-Lymphotrophic Virus Type III (HTLV-III)" *Science* (1985), 229:69-72.

Baker, C.C. and Howley, P.M. "Differential promoter utilization by the bovine papillomavirus in transformed cells and productively infected wart tissue", *EMBO J.* (1987), 6(4):1027-1035.

Baker, C.C. et al., "Structural and Transcriptional Analysis of Human Papillomavirus Type 16 Sequences in Cervical Carcinoma Cell Lines", *J. Virol.* (1987), 61(4):962-971.

Baldwin, A.S., Jr., et al., "Induction of $NF_\kappa B$ DNA-Binding Activity during the $G_0$-to-$G_1$ Transition in Mouse Fibroblasts", *Molecular and Cellular Biology* (1991), 11(10):4943-4951.

Beg, A.A., et al., "IκB interacts with the nuclear localization of the subunits of $NF_\kappa B$: a mechanism for cytoplasmic retention", *Genes & Development* (1992), 6:1899-1913.

Berg, J.M. "Potential Metal-Binding Domains in Nucleic Acid Binding Proteins" *Science* (1986), 232:485-487.

Bulow, et al., "A general and sensitive method for staining DNA and RNA blots", *Nucleic Acids Res.* (1986), 14(9):3973.

Chandrasegaran et al., "Chimeric Restriction Enzymes: What is Next?", *Biol. Chem.*, 1999, vol. 380, pp. 841-848.

Chapman et al., "Ubiquitous GFP expression in transgenic chickens using a lentiviral vector", *Development*, vol. 132, issue 5, pp. 935-940.

Courey, A.J. and Tijan, R. "Analysis of Sp1 In Vivo Reveals Multiple Transcriptional Domains, including a Novel Glutamine-Rich Activation Motif" *Cell* (1988), 55:887-898.

Danheiser, S.L. "bDNA Assay Allows Monitoring of Virus Loan in HIV and HCV" *Genetic Engineering News* (1994), 14(18):1-27.

Desjarlais et al., "Use of a zinc-finger consensus sequence framework and specificity rules to design specific DNA binding proteins", *Proc. Natl. Acad. Sci.*, 1993, vol. 90, pp. 2256-2260.

Dittmer, J. et al., "Regulation of Parathyroid Hormone-related Protein (PTHrP) Gene Expression: Sp1 Binds Through an Inverted CACCC Motif and Regulates Promoter Activity in Cooperation with Ets1," *The Journal of Biological Chemistry*, Aug. 26, 1994, vol. 269, No. 34, pp. 21428-21434.

Dodd et al., "Octamerization of λ CI repressor is needed for effective repression of $P_{RM}$ and efficient switching from lysogeny", *Genes & Development*, 2001, vol. 15, pp. 3013-3022.

Dodd et al., "Cooperativity in the long-range gene regulation by the λ CI repressor", *Genes & Development*, 2004, vol. 18, pp. 344-354.

"Ansari Fingers reach for the genome" *Nature Biotechnology*, 2003, vol. 21, pp. 242-243.

Franzoso, G. et al., "The oncoprotein Bcl-3 can facilitate $NF_\kappa B$-mediated transactivation by removing inhibiting p50 homodimers from select κB" *EMBO J.* (1993), 12(10):3893-3901.

Ghosh, S. et al., "Cloning of the p50 DNA Binding Subunit of NF-KB: Homology to *rel* and *dorsal*", *Cell* (1990), 62:1019-1029.

Gill, G. et al., "A glutamine-rich hydrophobic patch in transcription factor Sp1 contacts the $dTAF_{II}110$ component of the *Drosophila* TFIID complex and mediates transcriptional activation" *Proc. Natl. Acad. Sci. USA* (1994), 91:192-196.

Grimm, S. and Baeuerle, P.A. "The inducible transcription factor $NF_\kappa B$: structure-function relationship of its protein subunits", *Biochem. J.* (1993), 290(Pt 2):297-308.

Harrich, D.J., et al., "TAR independent activation of the human immunodeficiency virus in phorbol ester stimulated T lymphocytes", *EMBO J.* (1990), 9:4417-4423.

Harrison, S.C. and Aggarwal, A.K. "DNA Recognition by Proteins with Helix-Turn-Helix Motif" *Annu. Rev. Biochem.* (1990), 59:933-969.

Haugen, T.H. et al., "*Trans*-activation of an upstream early gene promoter of bovine papilloma virus-1 by a product of the viral E2 gene", *EMBO J.* (1987), 6(1):145-152.

Hegde, R.S., et al., "Crystal structure at 1.7A of the bovine papillomavirus-1 E2 DNA-binding domain bound to its DNA target", *Nature* (1992), 359:505-512.

Henkel, T., et al., "Intramolecular Masking of the Nuclear Location Signal and Dimerization Domain in the Precursor for the p50 $NF_\kappa B$ Subunit", *Cell* (1992), 68:1121-1133.

Hiscott, J., et al., "Induction of Human Interferon Gene Expression is Associated with Nuclear Factor that Interacts with the $NF_\kappa B$ Site of the Human Immunodeficiency Virus Enhancer" *J. Virol.* (1989), 63(3):2557-2566.

Hochschild, A. and Ptashne, M. "Cooperative Binding of λ Repressors to Sites Separated by Integral Turns of the DNA Helix" *Cell* (1986), 44:681-687.

Hoffmann, A., et al., "Highly conserved core domain and unique N terminus with presumptive regulatory motifs in a human TATA factor (TFID)", *Nature* (1990), 346:387-396.

Anderson Human Gene Therapy, *Nature*, 1998, vol. 392 supplement, pp. 25-30.

Ikeda, T., et al., "Isolation of the chicken $NF_\kappa B$ p65 subunit-encoding cDNA and characterization of its products" *Gene* (1993), 133:237-242.

Jones, K.A. et al., "Activation of the AIDS Retrovirus Promoter by the Cellular Transcription Factor, Sp1" *Science* (1986), 232:755-759.

Jones, K.A., Luciw, P.A., Duchange, N., "Structural arrangements of transcription control domains within the 5'-untranslated leader regions of the HIV-1 and HIV-2 promoters", *Genes & Development* (1988), pp. 1101-1114.

Kadonaga, J.T. et al., "Isolation of cDNA Encoding Transcription Factor Sp1 and Functional Analysis of the DNA Binding Domain" *Cell* (1987), 51:1079-1090.

Keller, G.H., and Manak, M.M. *DNA Probes*, Stockton Press (1989), pp. v-xiii, 192-210, 215-230.

Kerr, L.D. et al., "Association between protp-oncoprotein Rel and TATA-binding protein mediates transcriptional activation by $NF_\kappa B$" *Nature* (1993), 365:412-419.

Kim, Y., et al. "Crystal structure of a yeast TBP/TATA-box complex" *Nature* (1993), 365:512-521.

Kim, J.L., et al., "Co-crystal structure of TBP recognizing the minor groove of a TATA element" *Nature* (1993), 365:520-527.

Koken, S.E.C., et al., "Natural Variants of the HIV-1 Long Terminal Request: Analysis of Promoters with Duplicated DNA Regulatory Motifs", *Virol.* (1992), 191:968-972.

Kunsch, C. et al., "Selection of Optimal κB/Rel DNA-Binding Motifs: Interaction of Both Subunits of $NF_\kappa B$ with DNA is required for Transcriptional Adtivation" *Mol. Cell. Biol.* (1992), 12(10):4412-4421.

Lambert, P.F., et al., "A Transcriptional Repressor Encoded by BPV-1 Shares a Common Caboxy-Terminal Domain with the E2 Transactivator" *Cell* (1987), 57:287-294.

Langdon, et al. "A chimeric activator of transcription that uses two DNA-binding domains to make simultaneous contact with pairs of recognition sites", *Molecular Microbiology*, 2001, vol. 41, issue 4, pp. 885-896.

Larson, et al., "Influence of template strandedness on in vitro replication of mutagen-damaged DNA", *Biochemistry* (1987), 26:2471-2479.

Leonardo, M.J. et al., "The Involvement of $NF_\kappa B$ in β-Interferon Gene Regulation Reveals Its Role as Widely Inducible Mediator of Signal Transduction" *Cell* (1989), 57:287-294.

Margolis, D.M., et al., "Transactivation of the HIV-1 LTR by HSV-1 Immediate-Early Gens", *Virol.* (1992), 186:788-791.

Matthews, J.A., et al., "Analytical strategies for the use of DNA probes", *Analyt. Biochem.*, 1988, 169:1-25.

Matthews, J.R. et al., "Rate of cysteine$_{62}$ in DNA recognition by the P50 subunit of NF$_\kappa$B", *Nuc. Acids Res.* (1993), 21(8):1727-1734.

Matsusaka, T., et al., "Transcription factors NF-IL6 and NF$_\kappa$B synergistaically activate transcription of the inflammatory cytokines, interleukin 8", *Proc. Natl. Acad. Sci. USA* (1993), 90:10193-10197.

McBride, A.A., et al., "The Papillomavirus E2 Regulatory Proteins" *J. Biol. Chem.* (1991), 266(28):18411-1814.

McBride, A.A., et al., "The carboxy-terminal domain shared by the bovine papillomavirus E2 transactivator and repressor proteins contains a specific DNA binding activity", *EMBO J.* (1988), 7(2):533-539.

Mukaida, N., et al., "Cooperative Interaction of Nuclear Factor -κB- and *cis*-Regulatory Enhancer Binding Protein-like Factor Binding Elements in Activating the Interleukin-8 Gene by Pro-inflammatory Cytokines", *J. Biol. Chem.* (1990), 265(34):21128-21133.

Musso, T., et al., "LPS-inducible nuclear factor in human monocytes that binds the negative regulatory element of the HIV LTR", *J. Leukocyte Biol.* (1994), 56:21-26.

Nikolov, D.B. et al., "Crystal structure of TFIID TATA-box binding protein", *Nature* (1992), 360:40-46.

Northtrop, J.P. et al., "NF-AT components define a family of transcription factors targeted in T-cell activation", *Nature* (1994), 369:497-502.

Perkins, N.D. et al., "A cooperative interaction between NF$_\kappa$B and Sp1 is required for HIV-1 enhancer activation", *The EMBO J.* (1993), 12(9):3551-3558.

Perkins et al., "Transcription Factor AP-2 Regulates Human Immunodeficiency Virus Type 1 Gene Expression," *Journal of Virology*, Oct. 1994, vol. 69, No. 10, pp. 6820-6823.

Peterson, M.G., et al., "Functional Domains and Upstrean Activation Properties of Cloned Human TATA Binding Protein", *Science* (1990), 1624-1630.

Phelps, W.C. and Howley, P.M. "Transcriptional *trans*-Activation by the Human Paillomavirus Type 16 E2 Gene Product" *J. Virol.* (1987), 61(5):1630-1638.

Ptashne, M., and Johnson, A.D., Pabo, C.O., "A Genetic Switch in a Bacterial Virus", *Scientific American* (1982), 247(5):128-140.

Ptashne, M. "How Gene Activators Work" *Scientific American* (1989), January 40-47.

Rosin, H. "Bad Blood", *The New Republic* (1994), p. 12.

Schwarz, E. et al., "Structure and transcription of human papillomavirus sequences in cervical carcinoma cells" *Nature* (1985), 314:111-114.

Sodroski, J. et al., "Location of the *Trans*-Activating Region on the Genome of Human T-Cell Lymphotropic Virus Type III", *Science* (1985), 229-74-77.

Sorscher, D. H. et al., "Initiation of Transcription at the Human Terminal Deoxynucleotidyl Transferase Gene Promoter: A Novel Role for the TATA Binding Protein," *Biochemistry*, Sep. 1994, vol. 33, No. 36, pp. 11025-11032.

Spalholz, B.A. et al., "Bovine Papillomavirus Transcriptional Regulation: Localization of the E2-Responsive Elements of the Long Control Region" *J. Virol.* (1987), 61(7)2128-2137.

Spalholz, B.A., Yang, Y.-C., Howley, P.M., "Transactivation of a Bovine Papilloma Virus Transcriptional Regulatory Element by the E2 Gene Product" *Cell* (1985), 42:183-191.

Tan, S. et al., "The Human Papillomavirus Type 16 E2 Transcription Factor Binds with Low Cooperativity to Two Flanking Sites and Represses the E6 Promoter through Displacement of Sp1 and TFIID," *Journal of Virology*, Oct. 1994, vol. 68, No. 10, pp. 6411-6420.

Taylor, I. "Johnson & Johnson leads race for over-the-counter HIV test" *Newark Star Ledger*, Jul. 24, 1994.

Tong-Starksen, S.E., et al., "Human Immunodeficiency virus long terminal repeat responds to T-cell activation signals", *Proc. Natl. Acad. Sci. USA* (1987), 84:6845-6849.

Urban, M.B., et al., "NF$_\kappa$B contacts DNA by a heterodimer of the p50 and p65 subunit", *EMBO J.* (1991), 10(7)1817-1825.

Verma et al., "Gene therapy—promises, problems, and prospects", *Nature*, 1997, vol. 389, pp. 239-242.

Wu, F.K., et al., "Purification of the human immunodeficiency virus type 1 enhancer and TAR binding proteins EBP-1 and UBP-1" *EMBO J.* (1988). 7(7):2117-2129.

Yee, C. et al. "Presence and Expression of Human Pailiomavirus Sequences in Human Cervical Carcinoma Cell Lines" *Am. J. Pathol.* (1985), 119:361-366.

Zabel, U., et al., "Nuclear uptake control of NF$_\kappa$B by MAD-3, an IκB protein present in the nucleus", *EMBO J.* (1993), 12(1):201-211.

Messer et al., "Tumor Necrosis Factor β (TNF-β) Induces Binding of the NF-κB Transcription Factor to a High-Affinity κB Element in the TNF-β Promoter," *Cytokine*, Nov. 1990, vol. 2, No. 6, pp. 389-397.

\* cited by examiner

SEQ. ID: 37:
```
          1234567890123456789012345678901234567890
CTACAAGGACTTTCCGCTGGGACTTTCCAGGAGGCGTGGCCTGGGCGGACTGGGGAGTGGCGTCCC
++++++++++++++++++++++++++++++++++++++
     NF-kB          NF-kB       SP1        SP1         SP1
```

HIV Test Kit PNA1 (+++ from above), SEQ.ID:38:

*CTACAAGGACTTTCCGCTGGGACTTTCCAGGAGG*

HIV Test Kit PNA2 (=== from above), SEQ. ID:39:

CGGGACTGGGGAGTGGCGTCCC###

The sticky end sequence in PNA2 is complimentary to one of the ends of the operator DNA formed from:

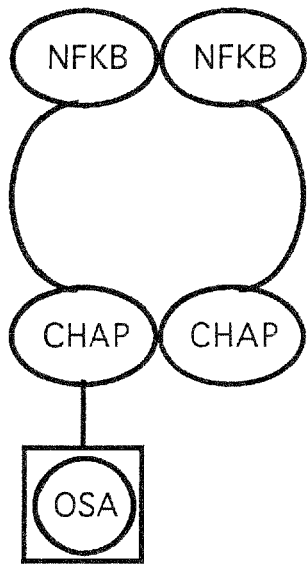
HIV-DETECT I
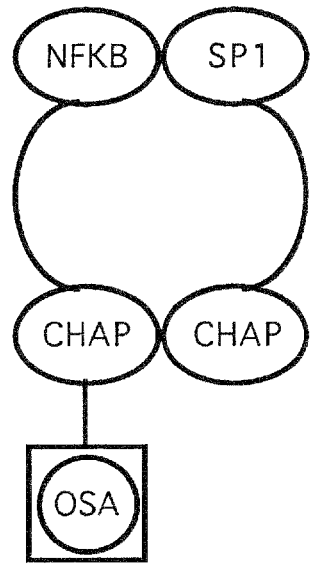
HIV-DETECT II
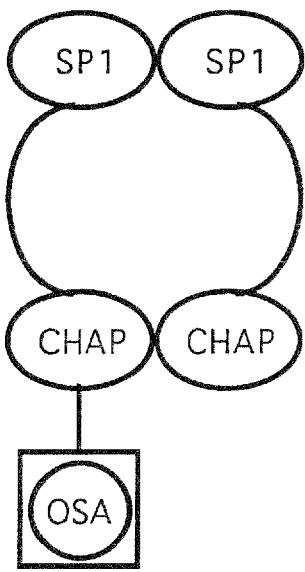
HIV-DETECT III
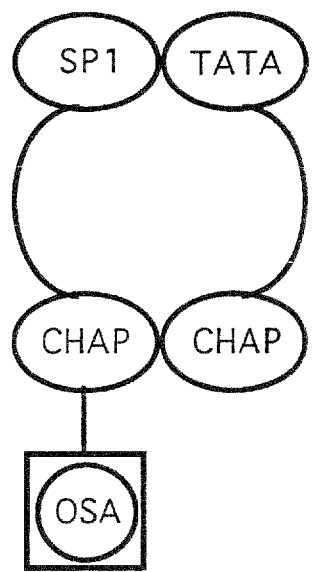
HIV-DETECT IV
FIG. 10

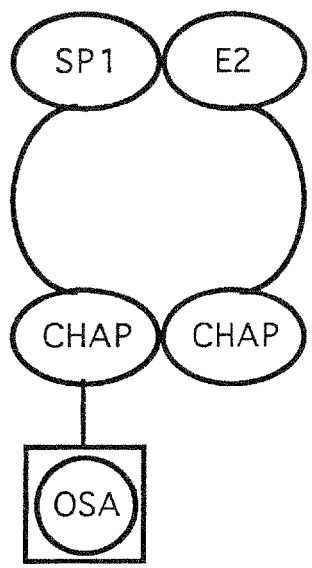
HPV-DETECT I
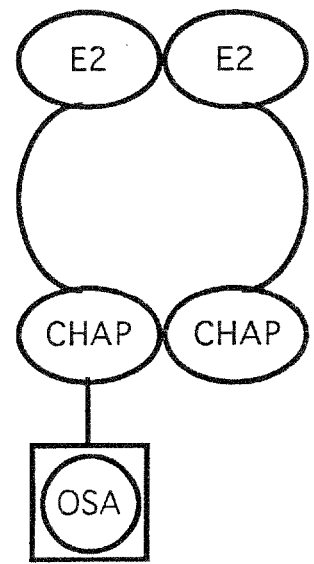
HPV-DETECT II
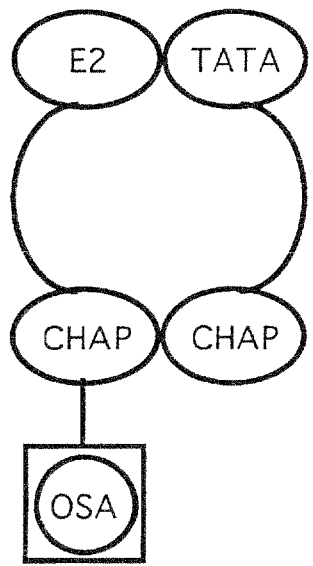
HPV-DETECT III
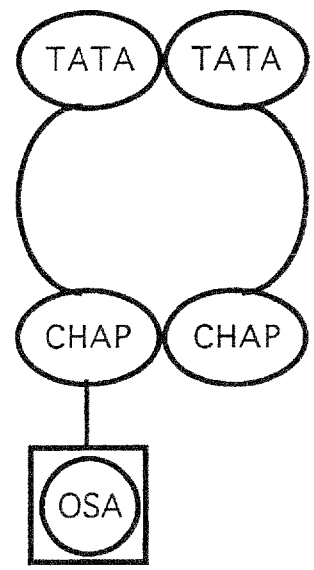
HPV-DETECT IV
FIG. 11

METHOD OF DETECTION OF NUCLEIC ACIDS WITH A SPECIFIC SEQUENCE COMPOSITION

CROSS-REFERENCE TO A RELATED APPLICATIONS

This application is a continuation application of application Ser. No. 10/407,543, filed Apr. 3, 2003, now abandoned; which is a continuation application of Ser. No. 08/860,844; filed Sep. 29, 1997, now abandoned; which is a 371 application of PCT/US95/15944, filed Dec. 7, 1995; said application Ser. No. 08/860,844 is a continuation-in-part application of Ser. No. 08/353,476, filed Dec. 9, 1994, now U.S. Pat. No. 5,871,902, all of which are incorporated herein by reference in their entireties.

BACKGROUND OF THE INVENTION

1. Field of the Invention

This invention provides a method and compositions for use in binding, detecting, and amplifying the detection of specific Target Nucleic Acid sequences in a sample with fidelity and accuracy, even in the presence of closely related but different nucleic acids. The binding may involve the chaperoning and assembly of specific molecules into Target Binding Assemblies which specifically bind Target Binding Regions formed by the hybridization of Probe Nucleic Acids and Target Nucleic Acid sequences. The amplifying may involve the chaperoning and/or assembly of specific molecules into Booster Binding Assemblies which specifically bind Booster Binding Regions formed by the hybridization of Booster Nucleic Acids with Probe Nucleic Acids, Target Nucleic Acids, or other Booster Nucleic Acids. A method, and compositions, involving Hairpin Nucleic Acids is also provided to enable control of the size of specifically or non-specifically elongated Booster Nucleic Acids and Booster Binding Assemblies used in the amplification. The detecting involves providing one or more detectable labels, including radioactive, light- or fluorescent-emitting, enzymatic, or other detectable or signal-generating molecules, in association with the Probe Nucleic Acid, the Target Binding Assembly, the Booster Nucleic Acid, the Booster Binding Assembly, or the Hairpin Nucleic Acid. A method is presented for isolating nucleic acid fragments from an organism which has TBA component binding sites in order to create a probe nucleic acid and a TBA which is unique for that fragment and/or organism. Therapeutic and prophylactic uses of the Target Binding Assemblies and compositions for such use are also provided.

2. Background and Description of Related Art

There are an increasing number of cases in which it is important to be able to detect nucleic acids containing a specific sequence, hereinafter named Target Nucleic Acids (TNAs), in a sample. It is desirable to be able to detect the TNAs with the smallest number of processing steps, with the simplest components and to the exclusion of other similar but different nucleic acids, hereinafter named Cousin Nucleic Acids (CNAs). It is desirable to be able to detect specific TNAs to the exclusion of any and all CNAs in the detection sample without the necessity of amplification or other post-detection processing.

There are numerous methods which use immobilized or tagged nucleic acids as probes for TNAs. However, using known methods, it is difficult to discriminate between a TNA bound to the Probe Nucleic Acid (PNA) as opposed to a CNA bound to the PNA. For example, one or more base mismatches between the PNA and a CNA can still result in a CNA-PNA hybridization which is almost indistinguishable from a TNA-PNA hybridization. Thus, hybridization alone is not an optimal indicator that a PNA has hybridized to a unique TNA.

There are many situations in which a PNA would be used to try to determine whether a TNA was present in a sample which may contain CNAs. Hybridization of the PNA to any CNA in this situation would limit the diagnostic value that the PNA might have for the detection of a TNA, absent additional verification. Furthermore, it is desirable to be able to detect and localize TNAs with low copy numbers in samples which may contain many copies of CNAs, without the necessity of creating additional copies of the TNA. It would also be desirable to be able to confirm the presence of CNAs, independent of the TNAs, without the necessity of separating the CNAs and TNAs in the sample.

Furthermore, it would be desirable to be able to amplify the signal of even a low frequency hybridization of a particular TNA-PNA. For this purpose, a method of polymerizing multiple copies of a label, hereinafter referred to as a Booster Nucleic Acid (BNA) onto the TNA-PNA would be desirable.

The instant invention provides methods and compositions for achieving the foregoing desired objectives. As revealed by the following review, the instant compositions and methods have not been reported or suggested in the art. A general and comprehensive review of the state of art of nucleic acid detection is provided in Keller, H., M. M. Manak (1989) *DNA Probes*, Stockton Press.

A method has been reported for detecting base pair mismatches by chemical means in order to determine whether a PNA has hybridized to a CNA rather than to a TNA. In U.S. Pat. No. 4,794,075 to Ford et al., a method for distinguishing fragments of DNA which contain single base mismatches from their perfectly paired homologs is discussed. Single stranded regions within a duplex fragment are modified with carbodiimide, which reacts with unpaired guanine (G) and thymine (T) residues in DNA. Linear duplex DNA molecules do not react, while DNA molecules with single base mismatches react quantitatively. Following reaction with carbodiimide, the DNA molecules are fractionated on high percentage polyacrylamide gels such that modified and unmodified fragments can be distinguished. Ford et at applied this technique in order to locate and purify DNA sequence differences responsible for phenotype variation and inherited disease. Although this method is useful for following variations in genetic material, it has a large number of steps, it requires costly components, and it does not offer a direct means of determining whether a PNA has hybridized to the TNA exclusive of CNAs in the sample.

There have been some attempts to assure that at least a portion of the hybridization between the PNA and another nucleic acid is complementary. One method involves the monitoring of transcription products which are produced if the PNA hybridizes to a nucleic acid sufficiently to be transcribed from a promoter site contained in the probe. U.S. Pat. No. 5,215,899 to Dattagupta discloses how specific nucleic acid sequences are amplified through the use of a hairpin probe which, upon hybridization with and ligation to a target sequence, is capable of being transcribed. The probe comprises a single stranded self-complementary sequence which, under hybridizing conditions, forms a hairpin structure having a functional promoter region, and further comprises a single stranded probe sequence extending from the 3' end of the hairpin sequence. Upon hybridization with a target sequence complementary to the probe sequence and ligation of the 3' end of the hybridized target sequence to the 5' end of the hairpin probe, the target sequence is rendered transcribable in the presence of a suitable RNA polymerase and appropriate ribonucleoside triphosphates (rNTPs). Amplification is accomplished by hybridizing the desired TNA sequence with the probe, ligating the TNA to the PNA, adding the RNA polymerase and the rNTPs to the separated hybrids, and allowing transcription to proceed until a desired amount of RNA transcription product has accumulated. That method generally and specifically involves the use of hairpin DNA formed with a single stranded unpaired end to anneal a target sequence. When the target sequence is bound, the production of RNA transcription products is enabled. Thus, the method involves the detection of secondary transcription products rather than the use of a nucleic acid binding assembly to directly immobilize and/or localize a target sequence. A CNA could easily bind to the probe, and the lack of complementarity would not necessarily interfere with the formation of a CNA-PNA hybrid which could then support the production of unwanted transcription products.

A CNA bound to the PNA might be detected if the lack of complementarity interferes with the susceptibility of the hybrid CNA-PNA pair to be cut by a restriction endonuclease. In U.S. Pat. No. 5,118,605 to Urdea and U.S. Pat. No. 4,775,619 to Urdea, novel methods for assaying a nucleic acid analyte were provided, which employ polynucleotides having oligonucleotide sequences substantially homologous to a sequence of interest in the analyte, where the presence or absence of hybridization at a predetermined stringency provides for the release of a label from a support. Various techniques are employed for binding a label to a support, whereupon cleavage of either a single or double strand, a label may be released from a support, and the release of the label can be detected as indicative of the presence of a particular polynucleotide sequence in a sample. However, this technique has the shortcoming that a CNA-PNA pair could be cut by the restriction endonuclease, even if there is a mismatch, so long as the mismatch was outside of the endonuclease recognition region. This would lead to failure of the assay to identify a CNA-PNA hybrid.

Another method uses a branched DNA probe to detect nucleic acids. U.S. Pat. No. 5,124,246 to Urdea et al. discloses linear or branched oligonucleotide multimers useful as amplifiers in biochemical assays which comprise (1) at least one first single-stranded oligonucleotide unit (PNA) that is complementary to a single-stranded oligonucleotide sequence of interest (TNA), and (2) a multiplicity of second single-stranded, oligonucleotide units that are complementary to a single-stranded labeled oligonucleotide. Although amplified sandwich nucleic acid hybridizations and immunoassays using the multimers are described, the method has the limitation that PNA-CNA hybridization could occur and would result in production of unwanted signal.

In addition to methods for identification of TNAs, methods have been disclosed for the amplification of this DNA. In U.S. Pat. No. 5,200,314 to Urdea, an analyte polynucleotide strand having an analyte sequence (TNA) is detected within a sample containing polynucleotides by contacting the analyte polynucleotide with a capture probe (PNA) under hybridizing conditions, where the capture probe has a first binding partner specific for the TNA, and a second binding sequence specific for a solid phase third binding partner. The resulting duplex is then immobilized by specific binding between the binding partners, and non-hound polynucleotides are separated from the bound species. The analyte polynucleotide is optionally displaced from the solid phase, then amplified by PCR. The PCR primers each have a polynucleotide region capable of hybridizing to a region of the analyte polynucleotide, and at least one of the primers further has an additional binding partner capable of binding a solid-phase binding partner. The amplified product is then separated from the reaction mixture by specific binding between the binding partners, and the amplified product is detected. Although it is possible to confirm (by PCR) that a particular nucleic acid has hybridized with the PNA, confirmation is expensive and involves multiple steps.

As for reports that involve the interaction of a double stranded nucleic acid and a DNA-binding protein, a method has been described whereby a sequence of immobilized DNA which contains binding sites for a single protein is used to purify that protein. U.S. Pat. No. 5,122,600 to Kawaguchi et al. discloses a DNA-immobilized microsphere comprising DNA chains having base sequences which specifically bind a particular protein, and a carrier having a particle size of not more than 50 μm and not less than 0.01 μm which does not adsorb any protein, said carrier and said DNA chains being bound to each other by a chemical bond, and a process for purifying a protein using said microsphere. As this is a purification method for a protein, it does not disclose a method of detection of a TNA nor a method whereby more than one protein is bound to a double stranded nucleic acid for the purposes of detection and localization of specific TNA sequences.

In EP 0 453 301, a method for detecting a polynucleotide target sequence in a sample was described wherein sequences in a TNA are detected by hybridizing a first and a second PNA to the TNA. Each of said first and second PNAs contained a pre-formed duplex sequence, or a duplex that is formed through chain extension, capable of binding a nucleotide sequence specific binding protein. A method for binding a nucleotide specific binding protein to a duplex formed between a TNA and a PNA only upon formation of a duplex between the PNA and TNA is neither disclosed nor suggested.

In U.S. Pat. No. 4,556,643, a method was disclosed for the non-radioactive detection of specific nucleotide sequences in a sample which involved hybridization of a probe containing DNA binding protein specific sequences. However, this disclosure neither taught nor suggested a method for binding a nucleotide specific binding protein to a duplex formed between a TNA and a PNA only upon formation of a duplex between sequences present in the PNA and sequences present in the TNA.

BRIEF SUMMARY OF THE INVENTION

Disclosed are methods by which specific Target Nucleic Acid (TNA) sequences are detected through the use of Probe Nucleic Acids (PNAs) which, upon hybridization with TNAs, are capable of binding Target Binding Assemblies (TBAs). Each TBA binds at least one specific region of the PNA-TNA hybrid pair, the Target Binding Region (TBR). The TBA is comprised of one or more molecules, one or more of which can bind to TBR sequences in a specific and sequence or conformation dependent manner. The TBA may comprise one or more piloting sequences, called "PILOTS" or "Asymmetry Sequences," which assemble and constrain the nucleotide binding components of the TBA to specific geometries. The PILOTS act to assemble specific nucleic acid recognition units or other pilots to which specific nucleic acid recognition units are attached into the TBAs in a predetermined fashion. The TBA may also contain one or more molecules which anchor or localize the TBA. Novel TBAs having unique discriminating characteristics which surprisingly render the TBAs useful not only as diagnostic tools but also as prophylactic or therapeutic compounds, are also disclosed. Disclosed are methods and compositions for utilization of the PNAs, TBRs, TBAs, and TBA PILOTS, including their utilization as components of diagnostic and forensic test kits and the utilization of the novel TBAs as prophylactic or therapeutic agents.

The PNAs, in addition to TNA-specific sequences, may also contain one or more sequences, 1/2 BBRs, capable of hybridizing with complementary 1/2 BBRs in Booster Nucleic Acids (BNAs). Through hybridization of added BNAs to the starter 1/2 BBRs present in the PNAs, extensions of the PNAs are made in the form of PNA-BNA and then BNA-BNA hybrids. These extensions can contain one or more Booster Binding Regions (BBRs). Each BBR is capable of binding a Booster Binding Assembly (BBA). The BBA is comprised of molecules, one or more of which can bind to a BBR in a specific and sequence or conformation dependent manner. The BBA may comprise one or more piloting sequences, called "PILOTS" or "Asymmetry Sequences," which assemble and constrain the nucleotide binding components of the TBA to specific geometries. The PILOTS act to assemble specific nucleic acid recognition units or other pilots to which specific nucleic acid recognition units are attached into the BBAs in a predetermined fashion. The BBA may contain molecules which anchor or localize the BBA or which allow for detection of the bound BBAs and thereby of the TBA-TNA-PNA complexes to which they, in turn, are bound. Disclosed are methods and compositions for utilization of the 1/2 BBRs, BNAs, BBRs, BBAs, and BBA PILOTS, including their utilization as components of diagnostic and forensic test kits.

Methods and compositions are disclosed for the use of Hairpin Nucleic Acids (HNAs) as capping structures. The HNAs contain a self-hybridizing region and a single stranded 1/2 BBR which, under hybridizing conditions, can hybridize directly to the 1/2 BBRs in the PNAs or the 1/2 BBRs in BNAs already bound to the PNAs, to terminate the extension of BNAs onto the PNA or onto other BNAs.

Methods and compositions are disclosed for test procedures and the production of a test kit containing PNAs, TBAs, TBRs, BNAs, BBRs, BBAs and HNAs for the detection, localization and differentiation of specific nucleic acid sequences, including nucleic acid sequences which are found in human cells, in the Human Immunodeficiency Virus (HIV), Human Papillomavirus (HPV), and in other nucleic acid containing systems including viruses and bacteria.

Accordingly, it is an object of this invention to provide methods and compositions for use in binding, detecting, and amplifying the detection of specific Target Nucelic Acid sequences in a sample with fidelity and accuracy, even in the presence of closely related but different nucleic acid sequences. Accordingly, it is an object of this invention to provide methods and compositions for the creation of Target Binding Assemblies which specifically bind Target Binding Regions formed by the hybridization of Probe Nucleic Acids and Target Nucleic Acid sequences.

Another object of this invention is to provide a method and compositions for the creation of Booster Binding Assemblies which specifically bind Booster Binding Regions funned by the hybridization of Booster Nucleic Acid sequences with Probe Nucleic Acids, Booster Nucleic Acids and Hairpin Nucleic Acids.

Another object of this invention is to provide a method and compositions containing Hairpin Nucleic Acids which enable the control of the size of specifically or non-specifically elongated Booster Nucleic Acids and Booster Binding Assemblies used in amplification of PNA-TNA hybridization events.

Another object of this invention is to provide a method and compositions for use in the selection, assembly and or chaperoning of specific molecules, each with nucleic acid binding discriminating capabilities, into Target and Booster Binding Assemblies.

Another object of this invention is to provide a method and compositions for use in amplifying the detection of Target Binding assemblies bound to Target Binding Regions using Booster Binding Assemblies and Booster Nucleic Acids.

Another object of this invention is to provide a method and compositions which allow the use of one or more detectable labels, including but limited to radioactive labels, light emitting, fluorescent, enzymatic or other signal generating molecules. These labels are used in association with Probe Nucleic Acids, Target Binding Assemblies, Booster Binding Assemblies, Booster Nucleic Acids or Hairpin Nucleic Acids.

Another object of this invention is to provide a method for isolating nucleic acid fragments form an organism which has TBA component binding sites in order to create Probe Nucleic Acids and TBAs which are unique for that fragment or organism.

BRIEF DESCRIPTION OF THE DRAWINGS

The following illustrations are contained in FIG. 1: FIG. 1-IIa is a TNA to which is added the components of FIG. 1-I, and, under hybridizing conditions, binds the PNA to form the components of FIG. 1-IIIa, a PNA-TNA hybrid containing at least one TBR. FIG. 1-IVa is a BNA which is added to the components of FIG. 1-IIIa and, under hybridizing conditions, binds the 1/2 BBR of FIG. 1-IIIa to form a PNA-BNA hybrid containing a BBR shown in FIG. 1-Va.

FIG. 1-IIb is a BNA which is added the components of FIG. 1-I, and which, under hybridizing conditions, binds the PNA to form the components of FIG. 1-IIIb, a PNA-TNA hybrid containing a BBR. FIG. 1-IVb is a TNA to which is added the components of FIG. 1-IIIb and which, under hybridizing conditions, binds the 1/2 TBR of FIG. 1-IIIb to form a PNA-BNA hybrid containing a TBR shown in FIG. 1-Vb.

FIG. 1-IIc is a HNA which is added to the components of FIG. 1-I and which, under hybridizing conditions, binds the PNA to form the components of FIG. 1-IIIc, a PNA-HNA hybrid containing a BBR. FIG. 1-IVc is a TNA which is added to the components of FIG. 1-IIIc and which, under hybridizing conditions, binds the 1/2 TBR of FIG. 1-IIIc to form a PNA-BNA hybrid containing a BBR shown in FIG. 1-IVc.

Figure 1:
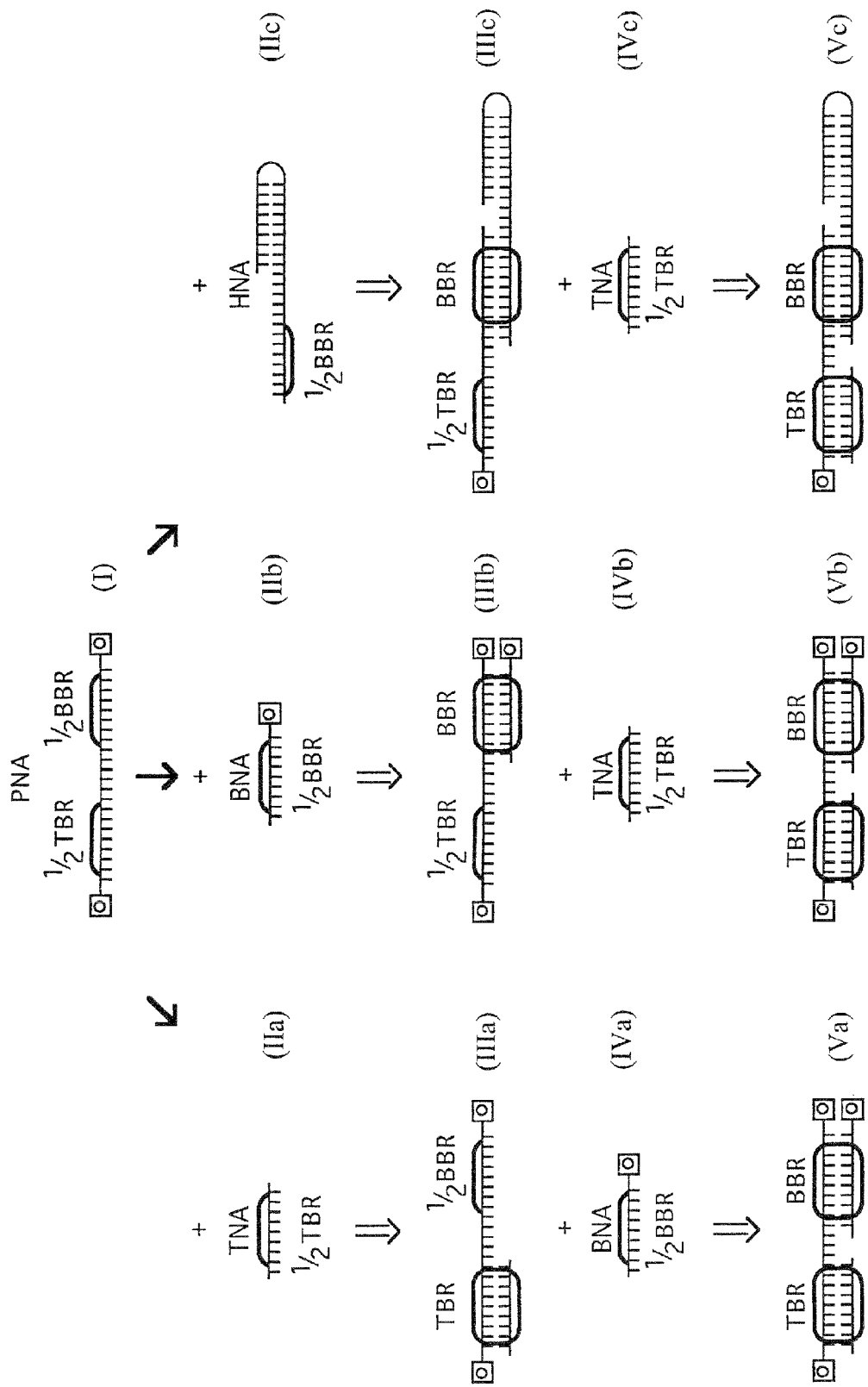
FIG. 1-I is a PNA containing a 1/2 TBR, which is a single-stranded sequence which is complementary to a TNA and a 1/2 BBR sequence.

The hybrids which form the TBRs and BBRs are useful in the present invention. The PNAs and BNAs, as indicated in FIG. 1, may contain no attached support and/or indicator (OSA), or an attached support or other means of localization, including, but not limited to, attachment to beads, polymers, and surfaces, and/or indicators.

Figure 2A:
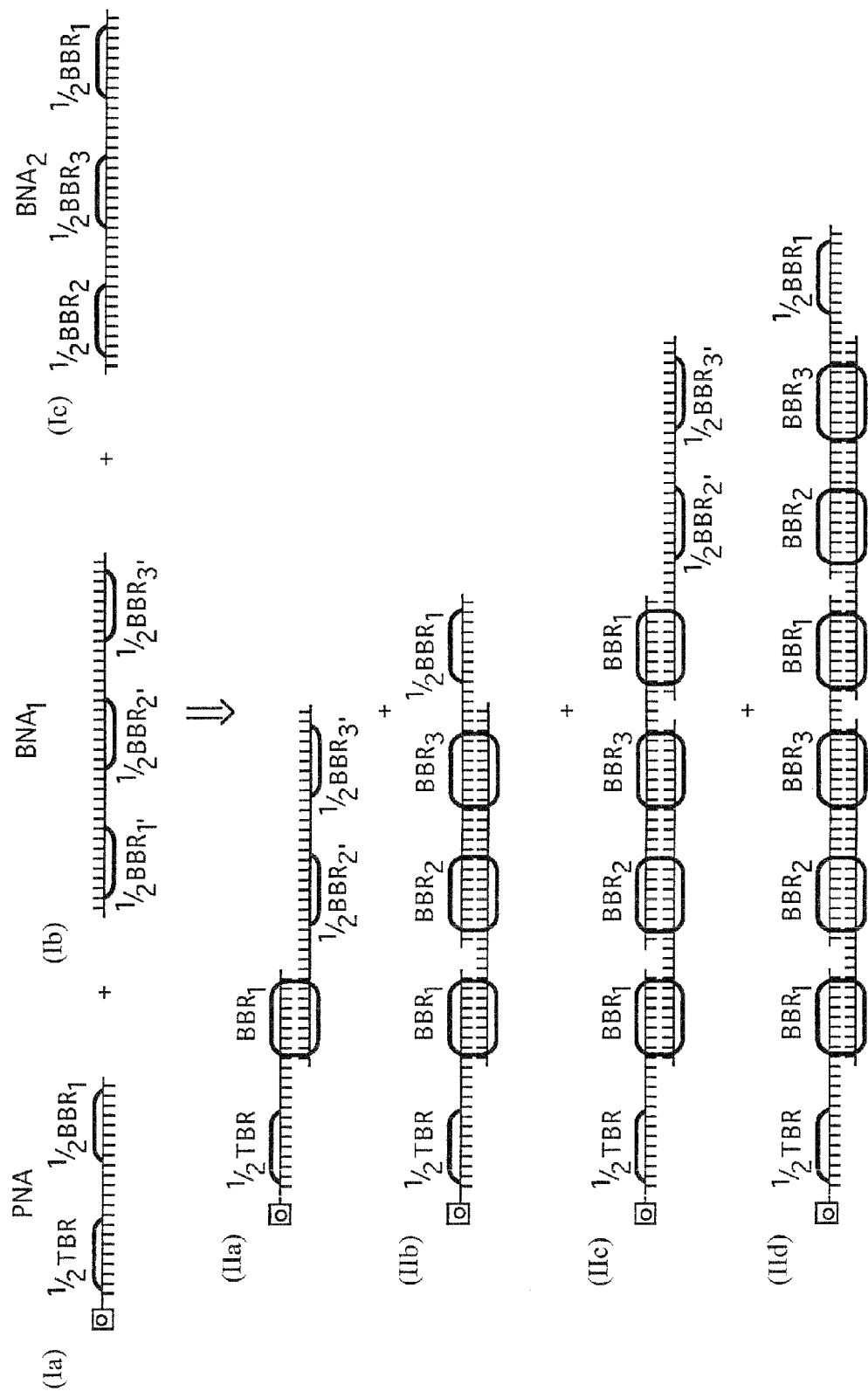

FIG. 2a is a diagram of strategies for polymerization of BNAs onto PNAs and capping by HNAs.

Figure 2B:
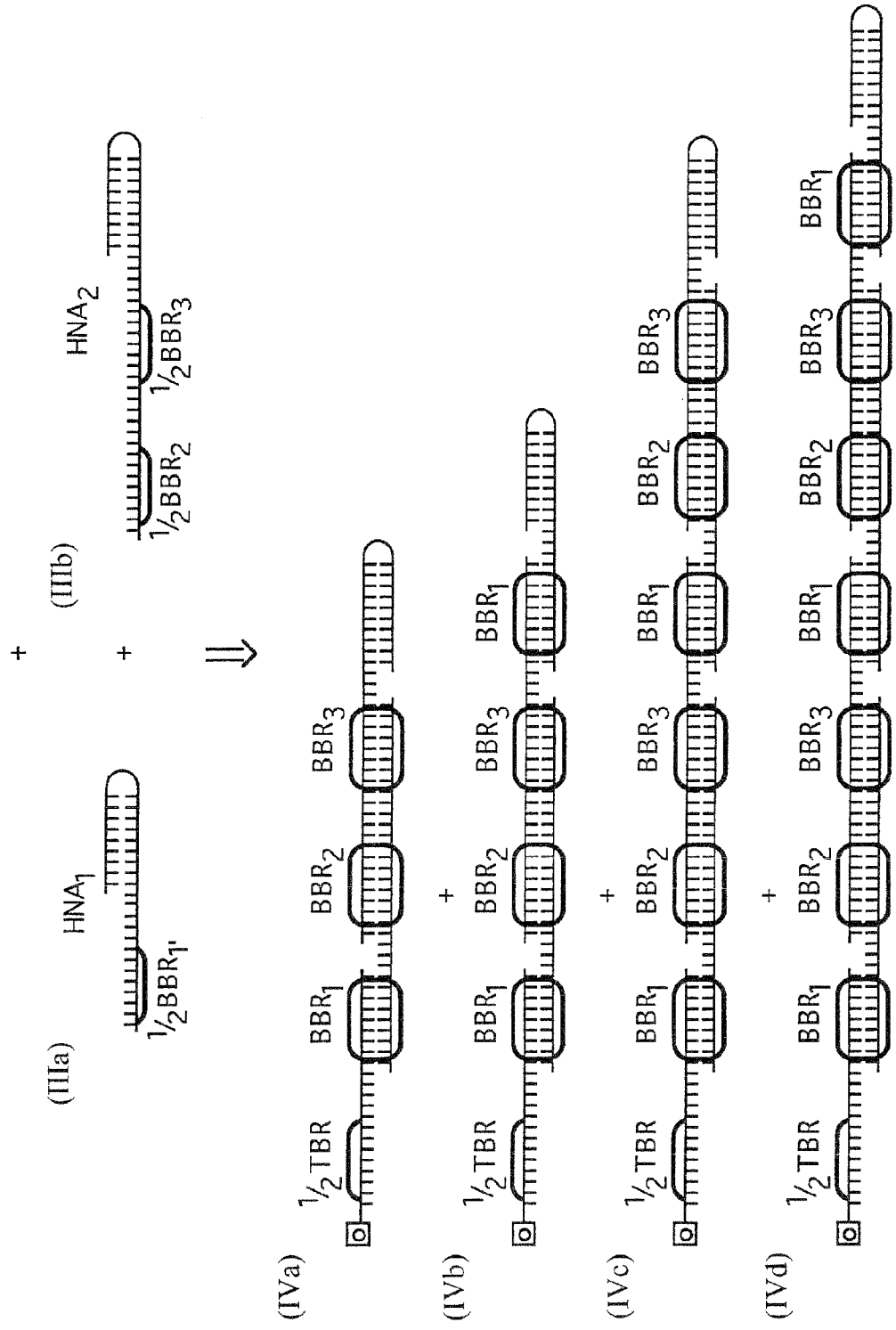
Figure 2C:
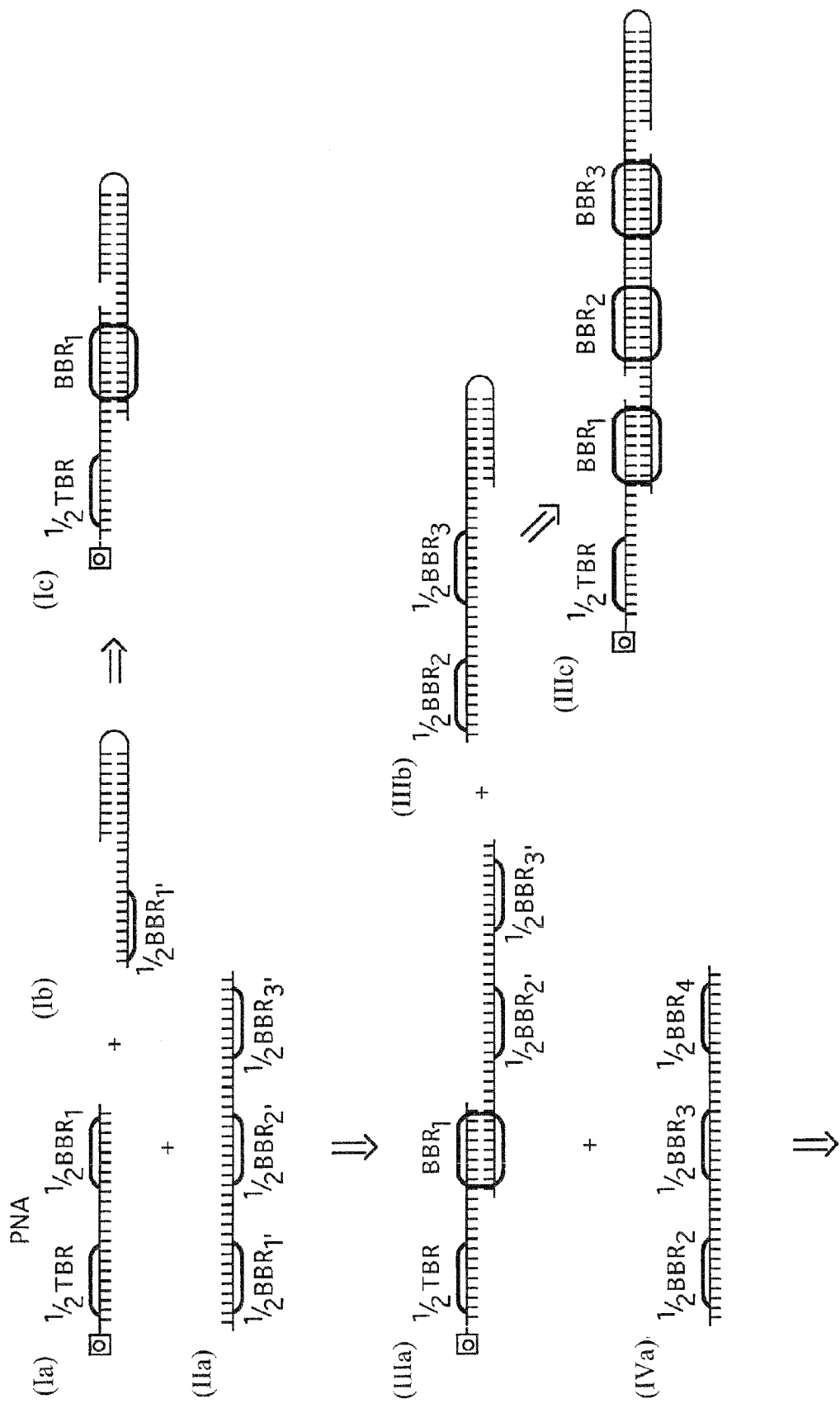
Figure 2D:
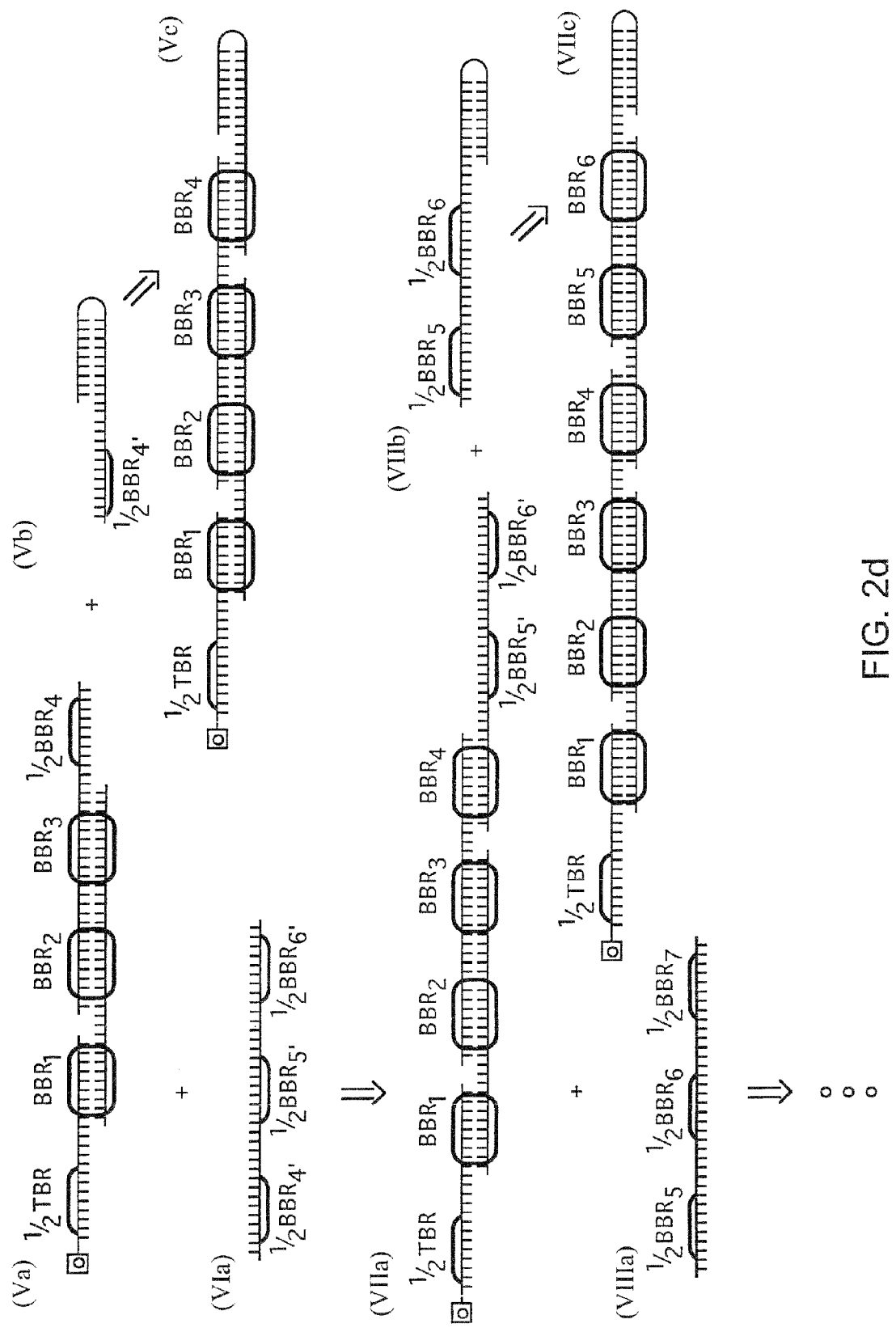

FIGS. 2b, 2c and 2d are diagrams of additional strategies for amplifying PNA-TNA signals via polymerization of BNAs and capping by HNAs.

Figure 3A:
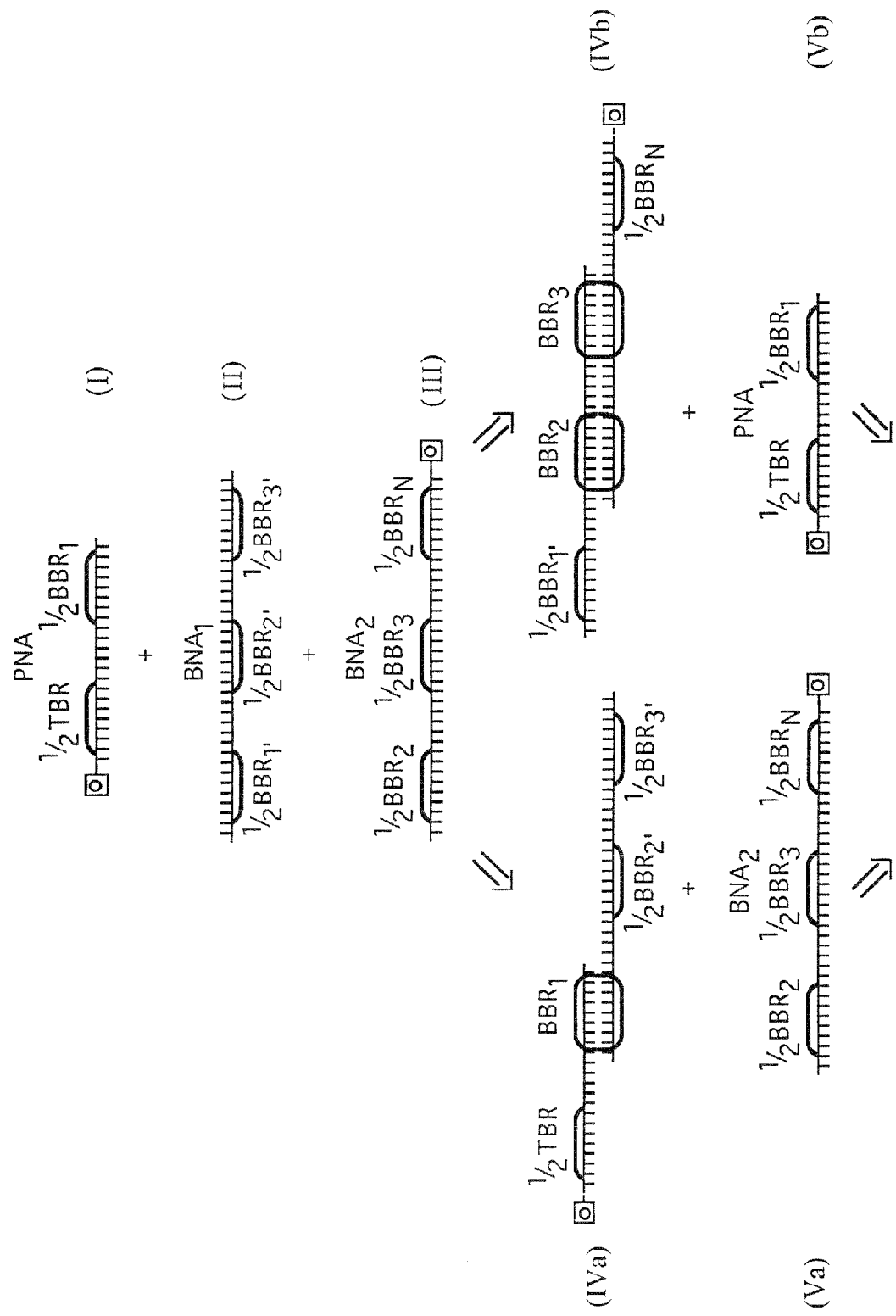
Figure 3B:
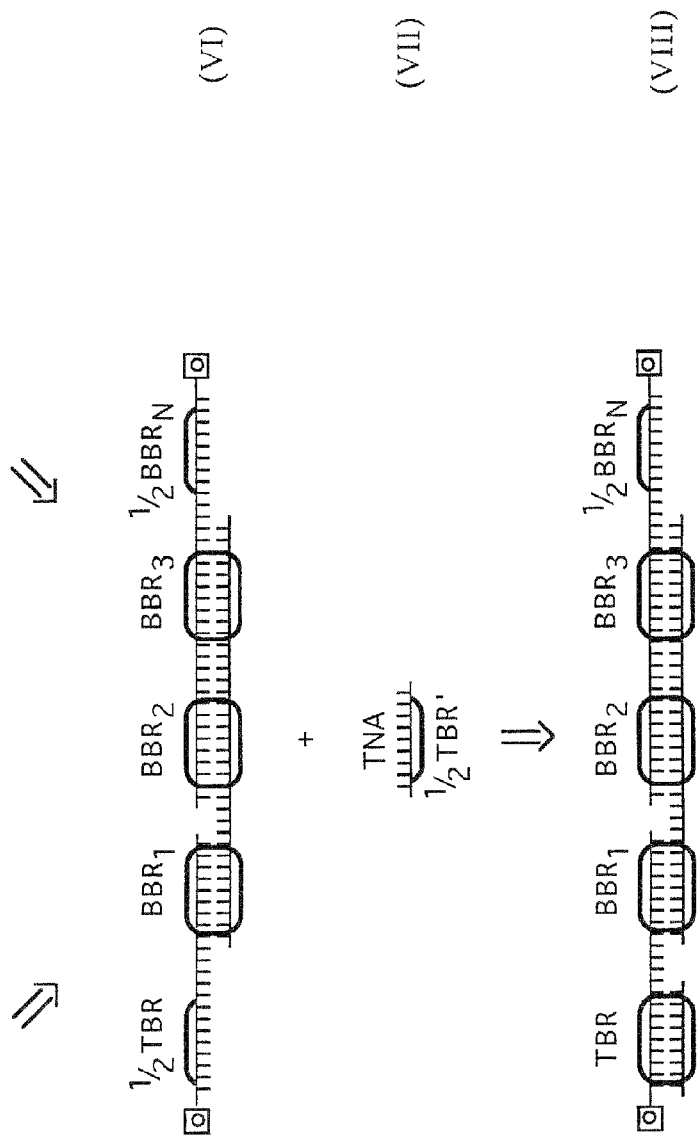

FIGS. 3a and 3b are diagrams showing the use of BNAs containing multiple 1/2 BBRs per BNA.

Figure 4A:
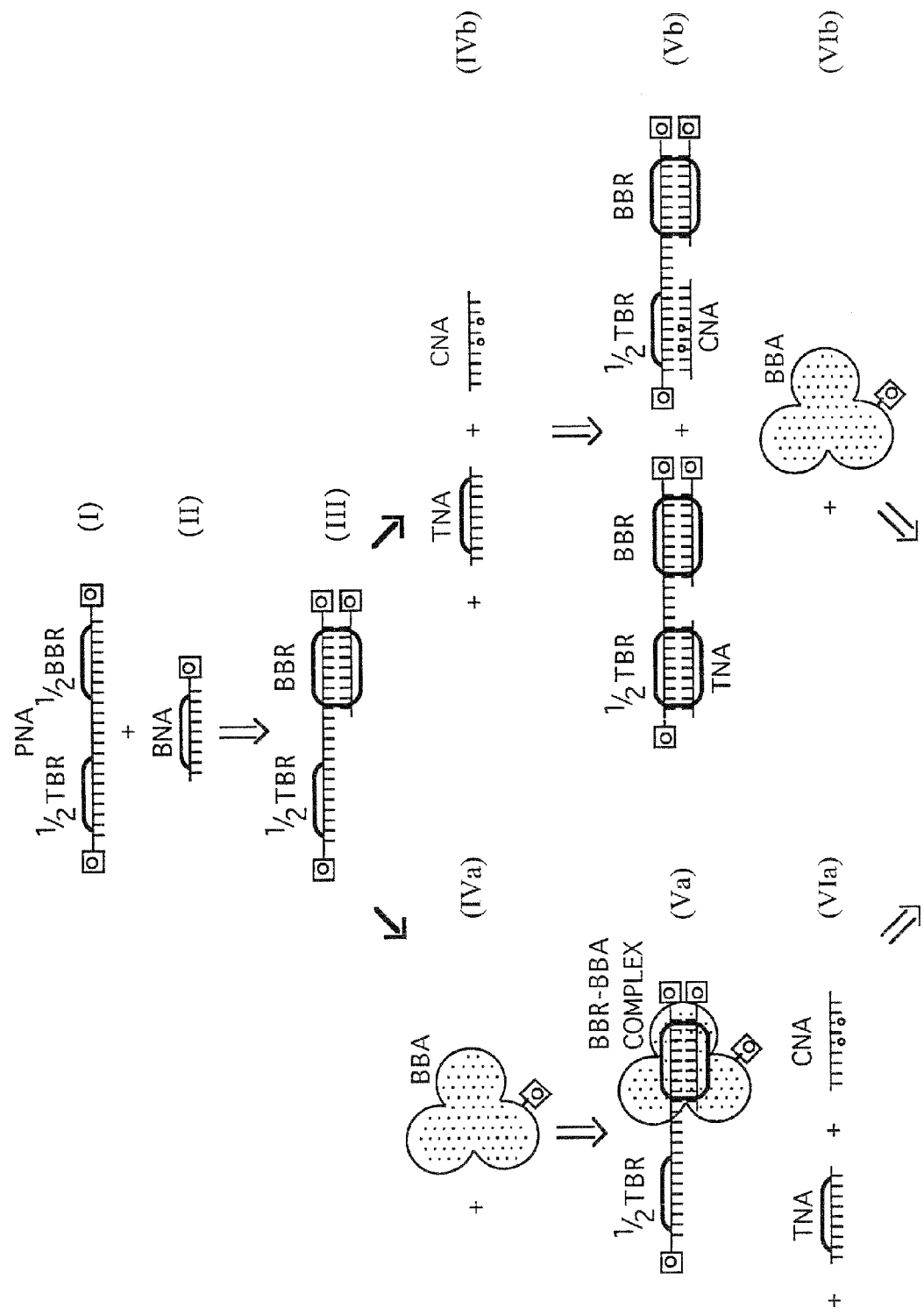

FIG. 4a is a diagram showing the binding of TBAs and BBAs to TBRs and BBRs, and the ability of the TBA to discriminate between TNAs and CNAs. According to this embodiment, if the TBA is immobilized, either on a bead, microtiter plate surface, or any other such surface, only complexes such as complex X would be retained and detected, while complexes such as complex XI would not.

Figure 4B:
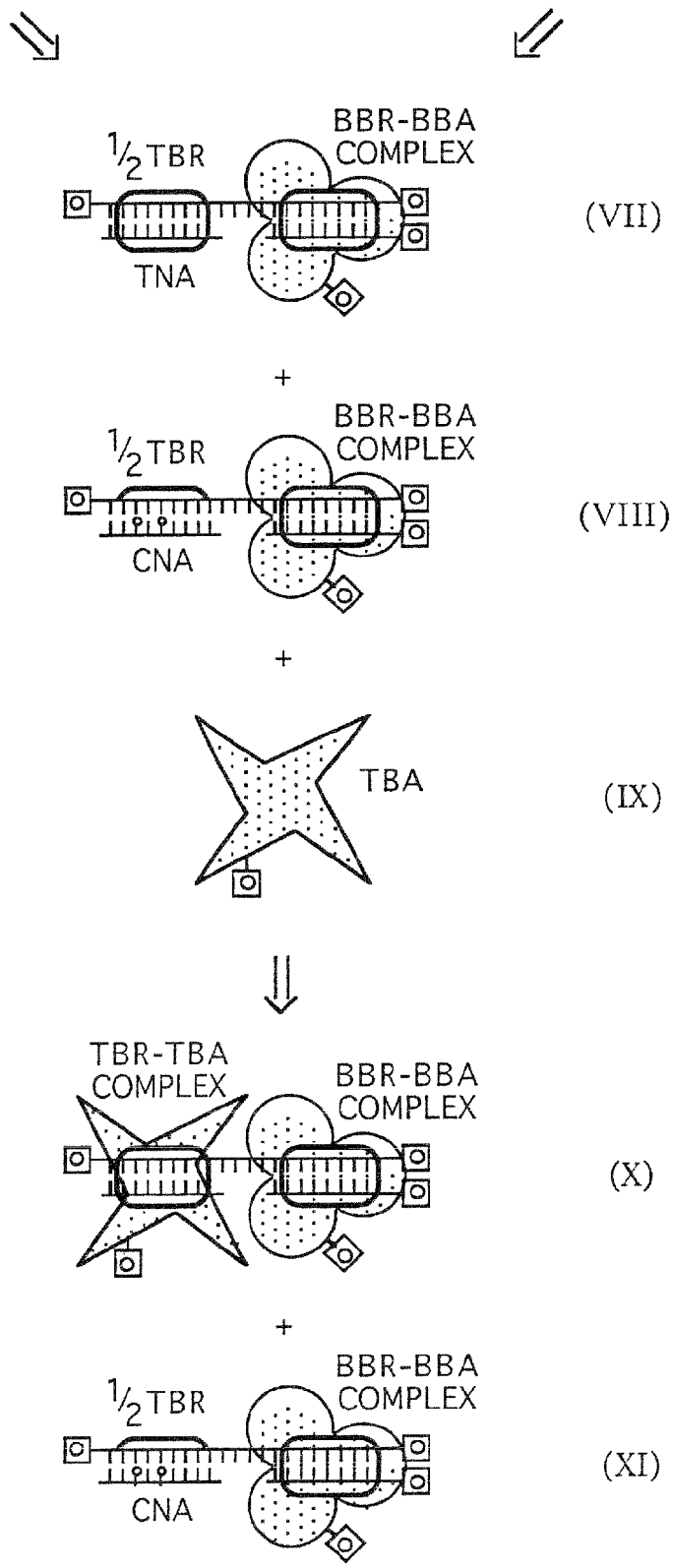

FIG. 4b is a diagram exemplifying events similar to those shown in FIG. 4a but in a slightly different order of occurrence.

Figure 4C:
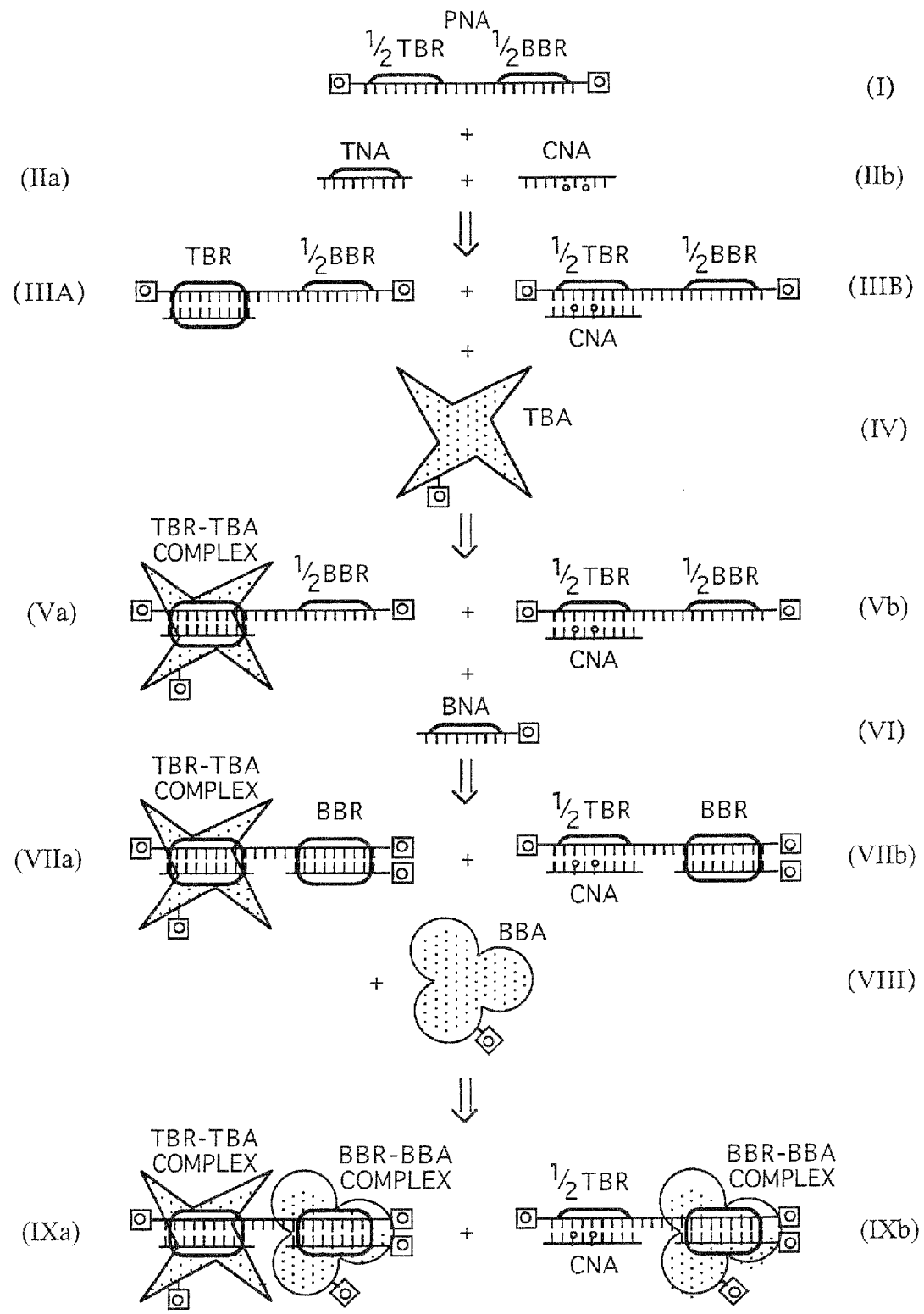

FIG. 4c is a diagram exemplifying events similar to those shown in FIG. 4a, but in a slightly different order of occurrence.

Figure 5:
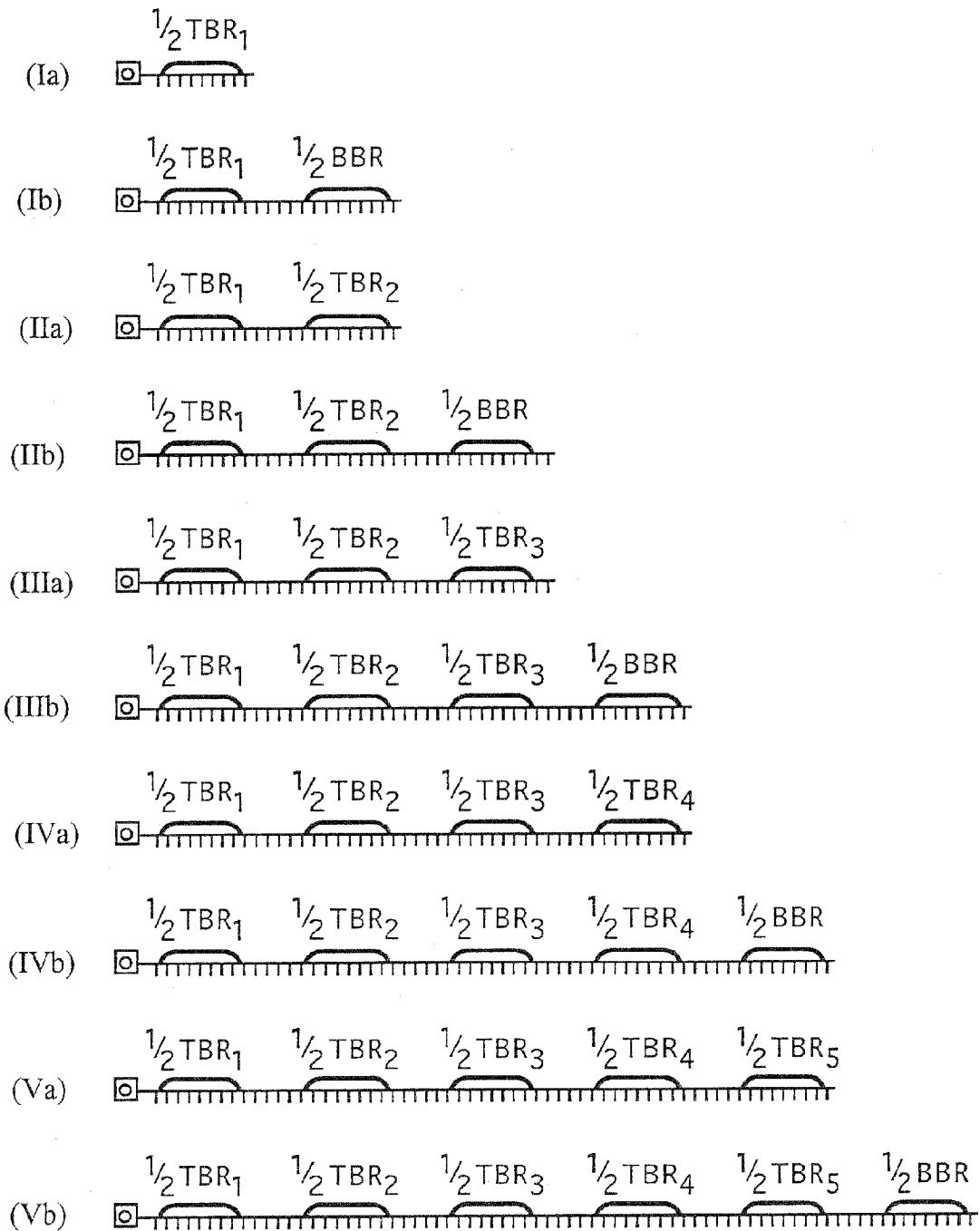

FIG. 5 is a diagram exemplifying PNAs containing between one 1/2 TBR and no 1/2 BBR to PNAs containing up to five 1/2 TBRs and one 1/2 BBR. The (a) and (b) members of each numeral (I, II, III, IV, V) form a set which, upon hybridization to a TNA, provide TBRs either with ((a) members) or without ((b) members) an available 1/2 BBR for amplification via hybridization to BNAs having complementary 1/2 BBRs.

Figure 6A:
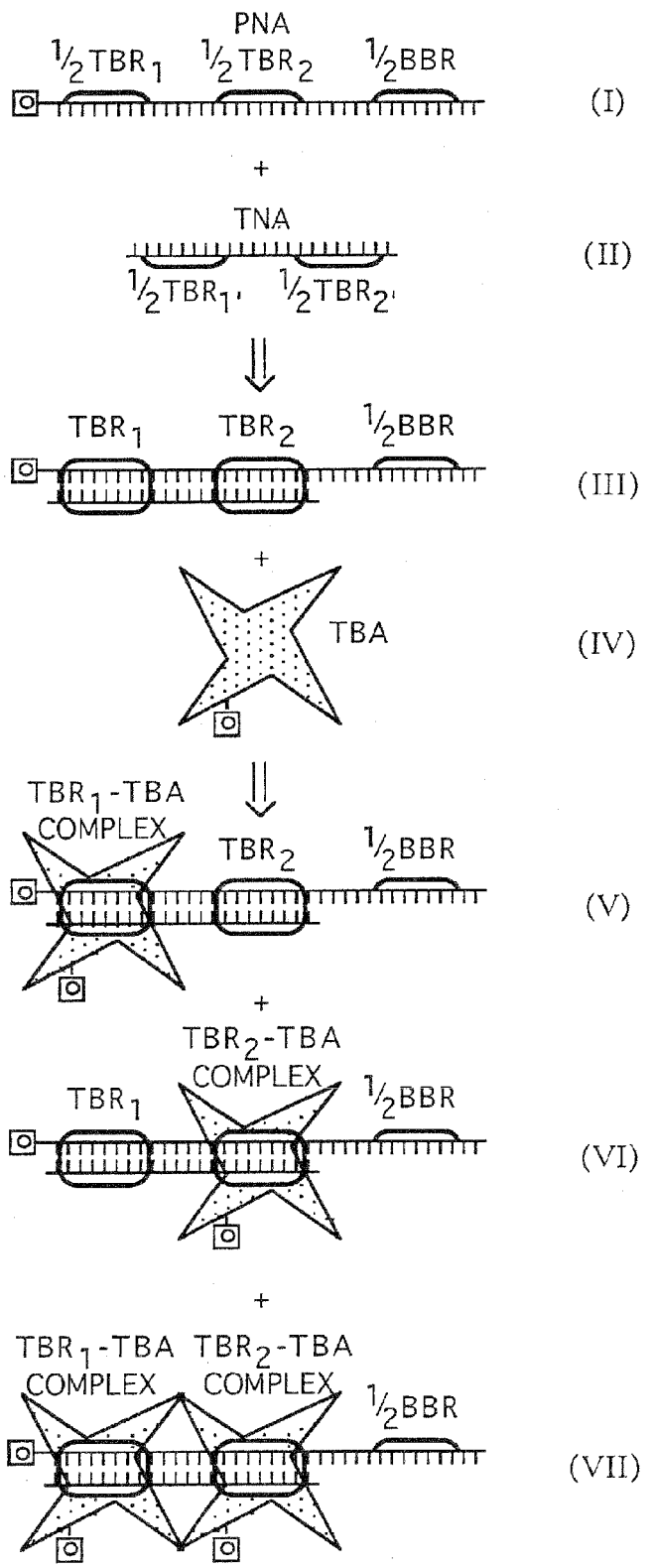

FIG. 6a is a diagram exemplifying a particular TNA having two 1/2 TBRs which, upon binding an appropriate PNA, forms two closely associated TBRs capable of binding two TBAs. A 1/2 BBR is also provided for amplification.

Figure 6B:
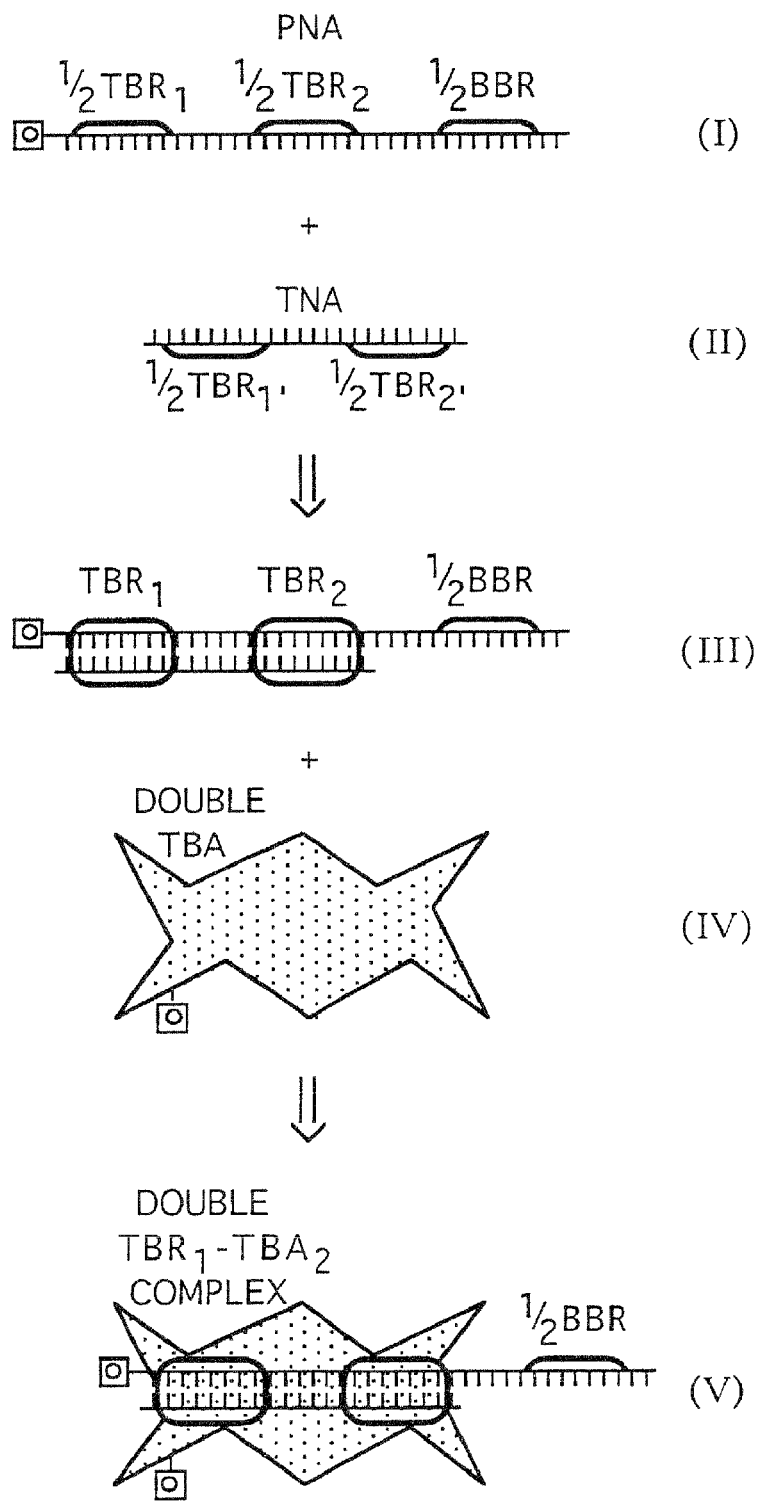

FIG. 6b is a diagram showing the same events as in FIG. 6a except here, a double TBA is used so that discrimination between single TBRs that occur in normal cellular samples may be discriminated from abnormal, double TBRs.

Figure 6C:
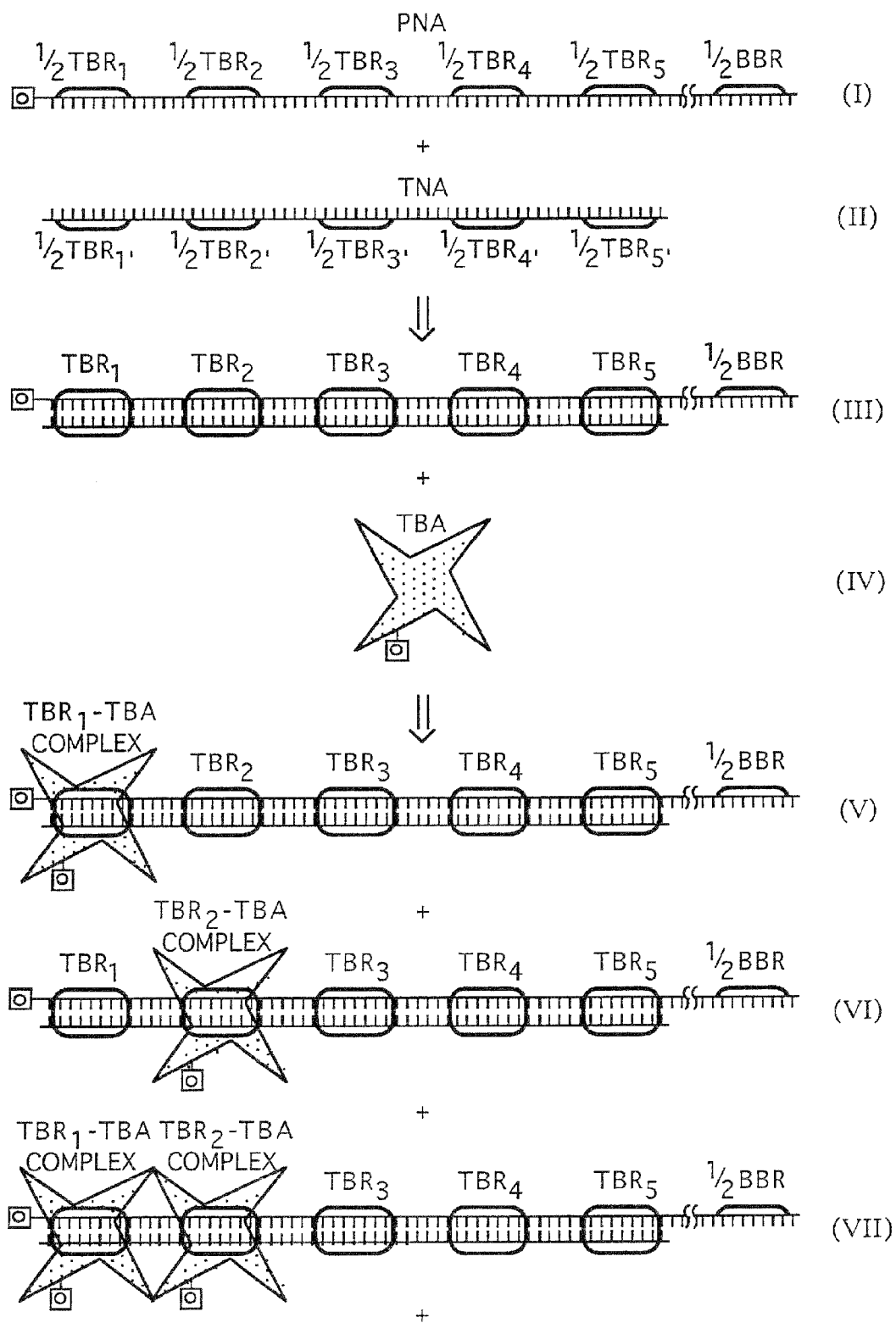

FIG. 6c is a diagram showing the same scenario as in FIG. 6a except that here, five TBRs are identified in the TNA. Each TBR may be bound to a TBA same or different, and each TBA may be differentially labeled, allowing for confirmation that all five sites are present in the TNA.

Figure 6D:
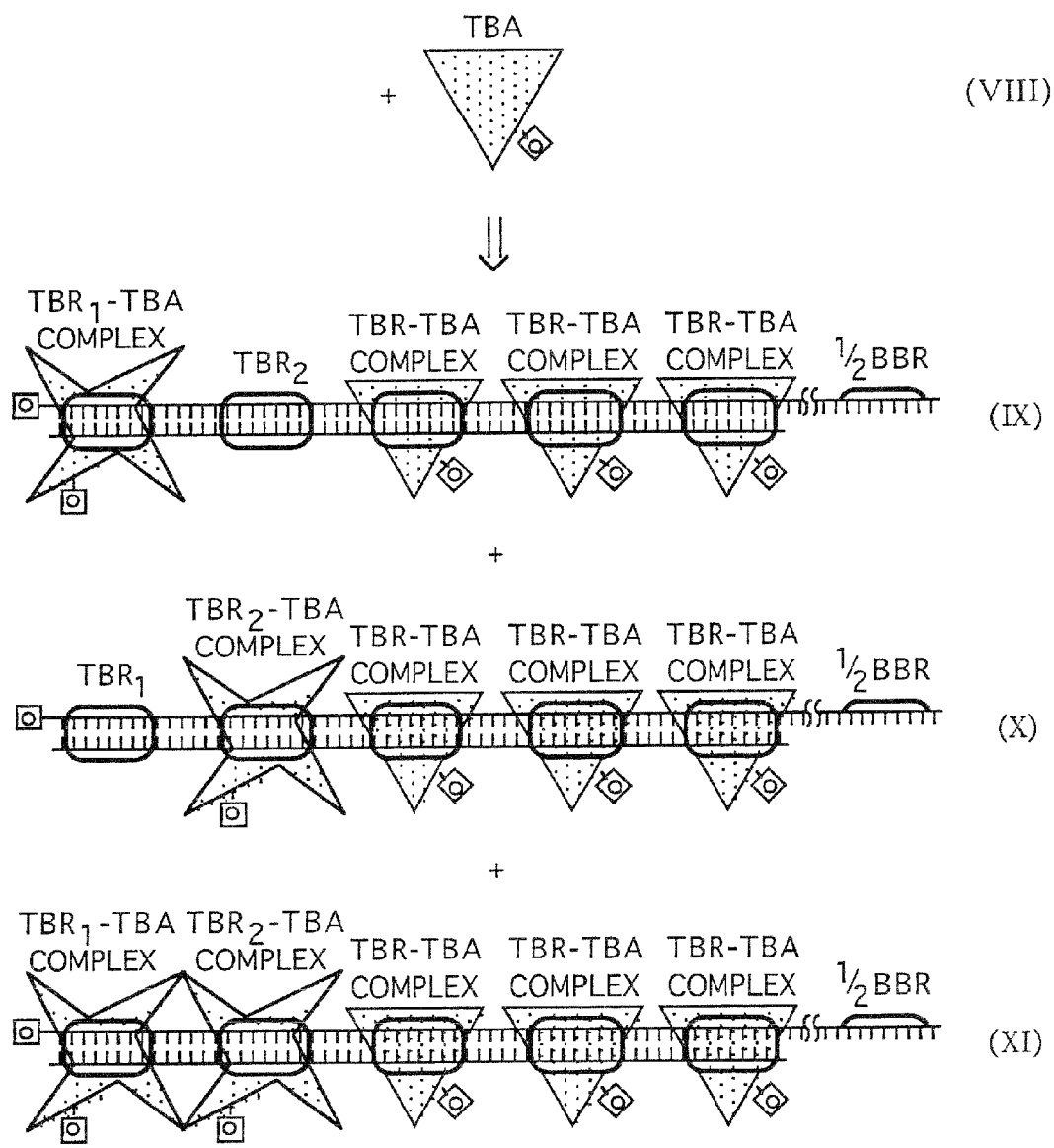

FIG. 6d is a diagram of the same events as in FIG. 6c except here, a double TBA is shown, extending what is shown in FIG. 6b to the use of the double TBA. An example of the TNA shown in item II in FIGS. 6a, 6b, 6c and 6d is HIV single stranded DNA or RNA.

Figure 6E:
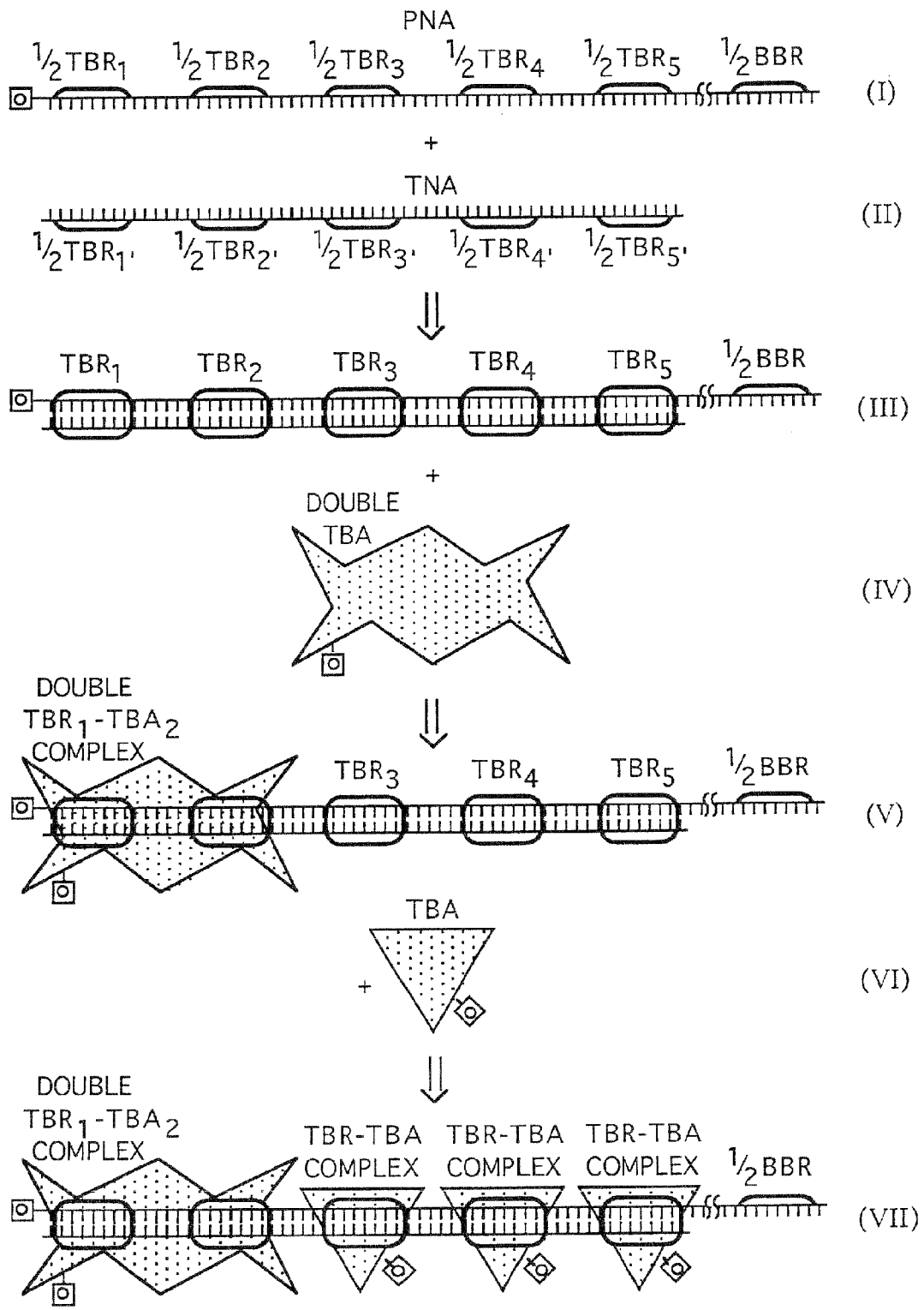

FIG. 6e is a diagram of the same events as in FIG. 6c except here, a double TBA is shown, extending what is shown in FIG. 6b to the use of the double TBA. An example of the TNA shown in item II in FIGS. 6a, 6b, 6c, and 6d is HIV single stranded DNA or RNA.

FIG. 7 shows the HIV LTR as a TNA, and two PNAs, and a strategy for detection of the TNA using the PNAs.

Figure 8A:
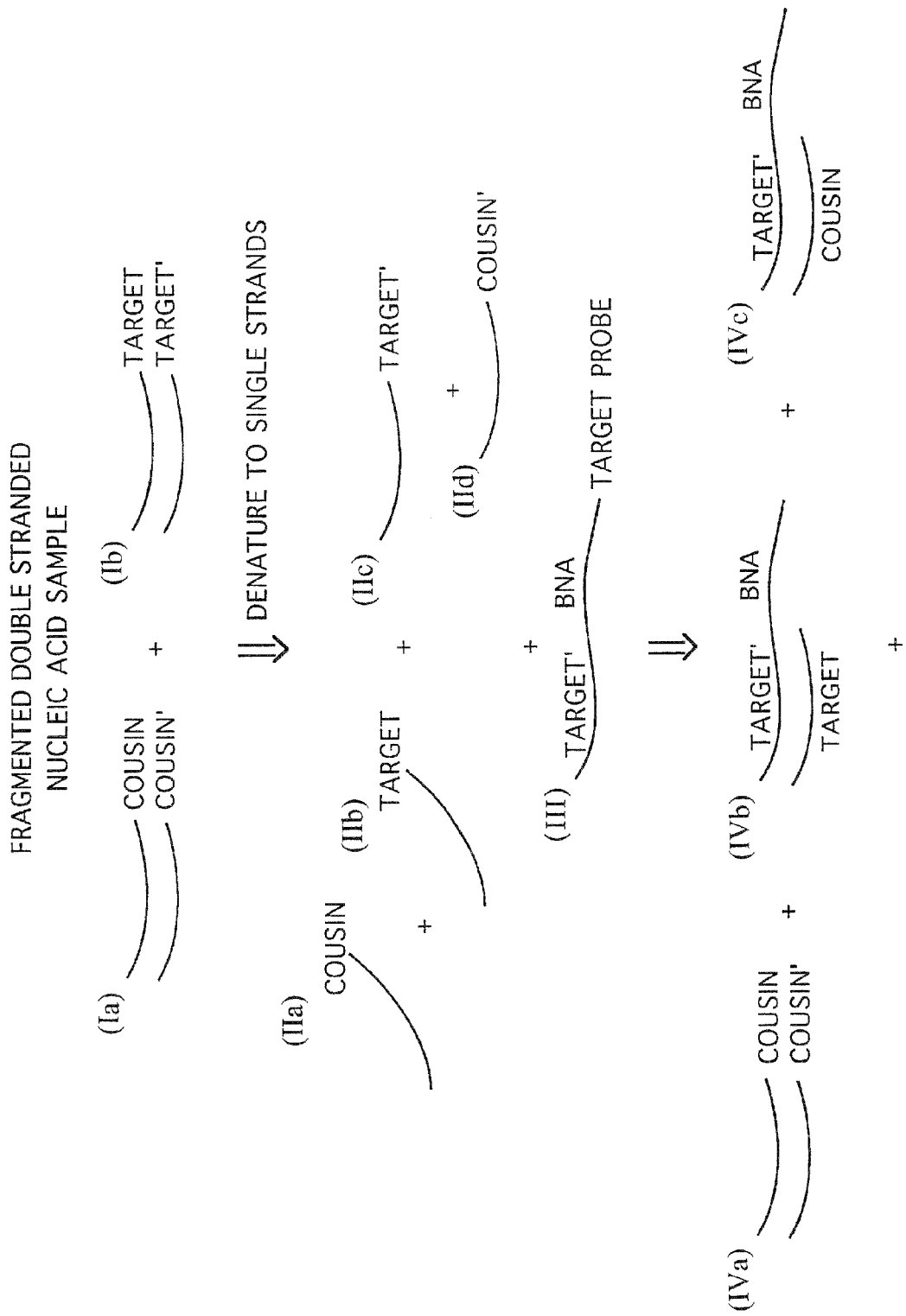
Figure 8B:
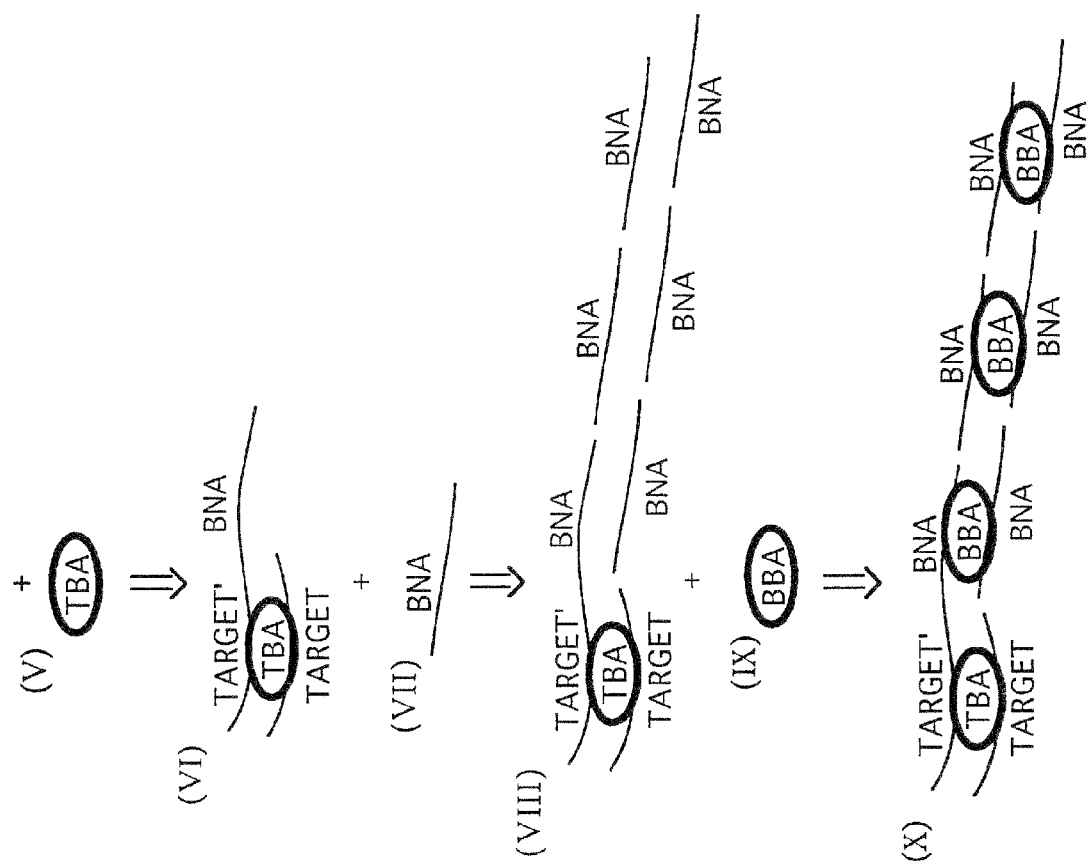

FIGS. 8a and 8b are a schematic of one embodiment of the invention wherein a target binding assembly is used to bind a hybrid TNA-PNA, and booster binding assemblies are used to bind polymerized BNAs.

Figure 9:
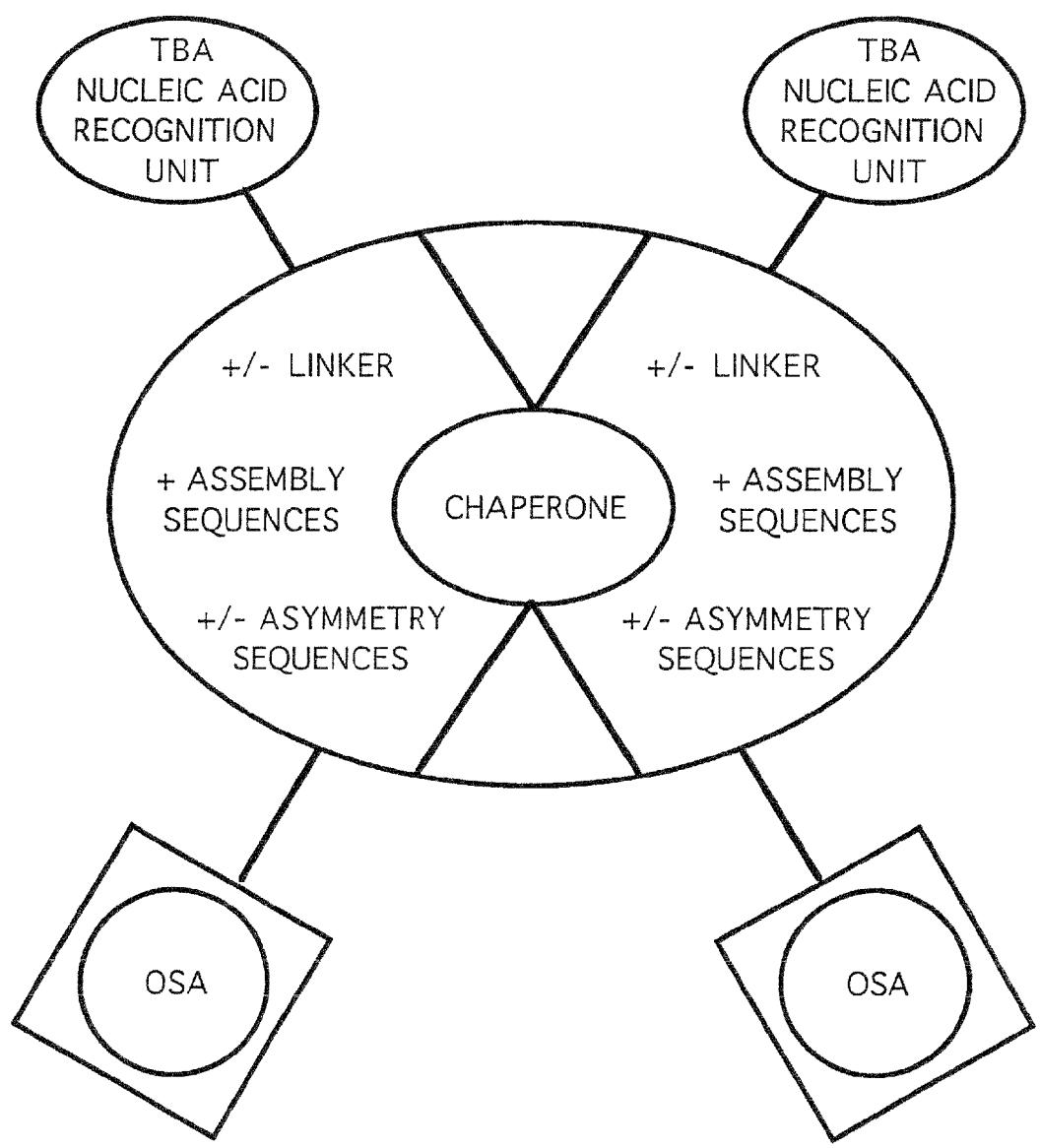

FIG. 9 is a schematic of a modular TBA in which assembly sequences, linker sequences, and asymmetry sequences are used to chaperone desired nucleic acid recognition units together to form a TBA.

FIG. 10 shows modular TBAs useful in detection of HIV-specific sequences.

FIG. 11 shows modular TBAs useful in the detection of human papillomavirus sequences. Each unit of E2 is actually a dimer of the DNA binding portion of E2.

Figure 12A:
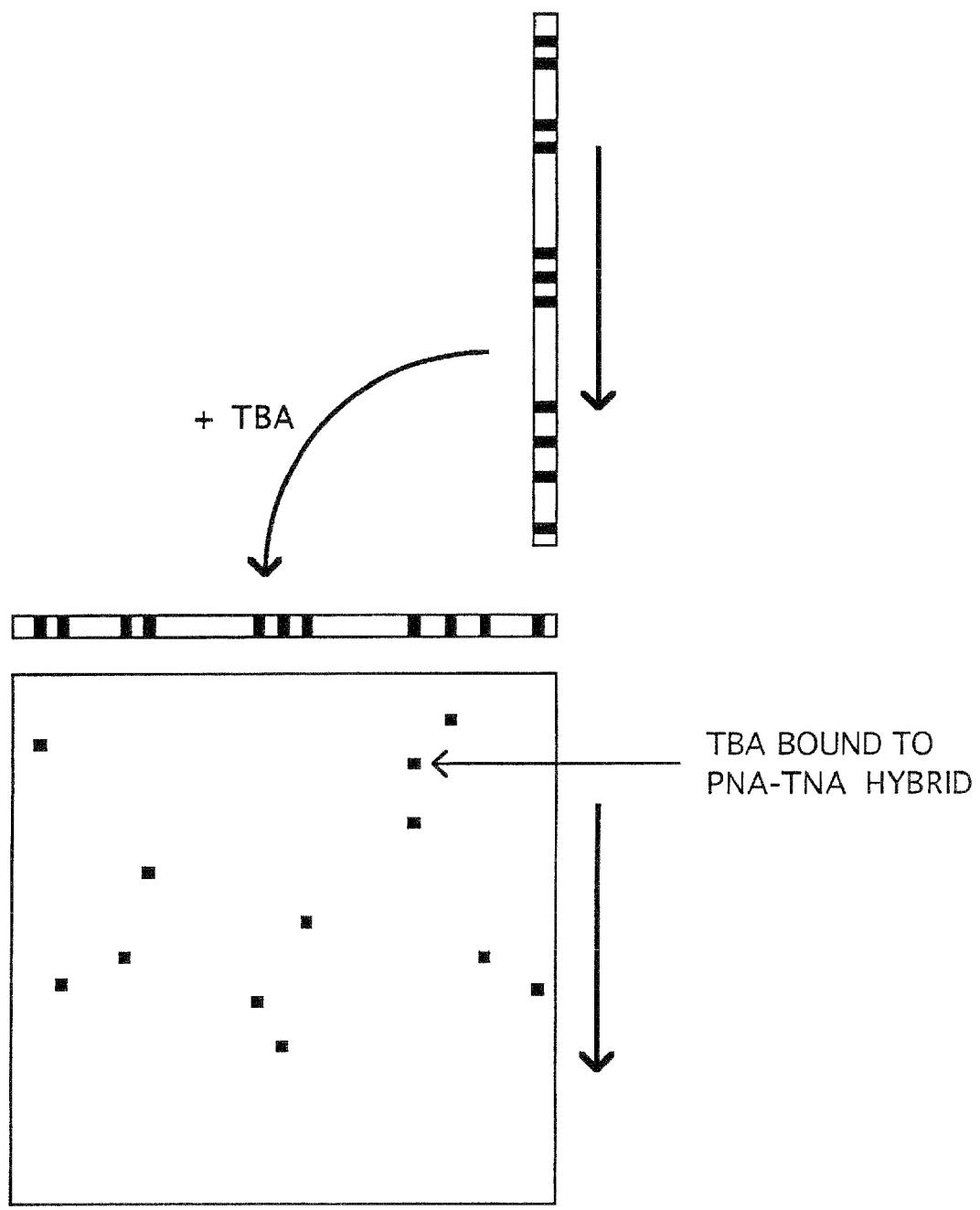

FIG. 12a is a schematic of TNA fractionation and shift in mobility due to binding of a TBA.

Figure 12B:
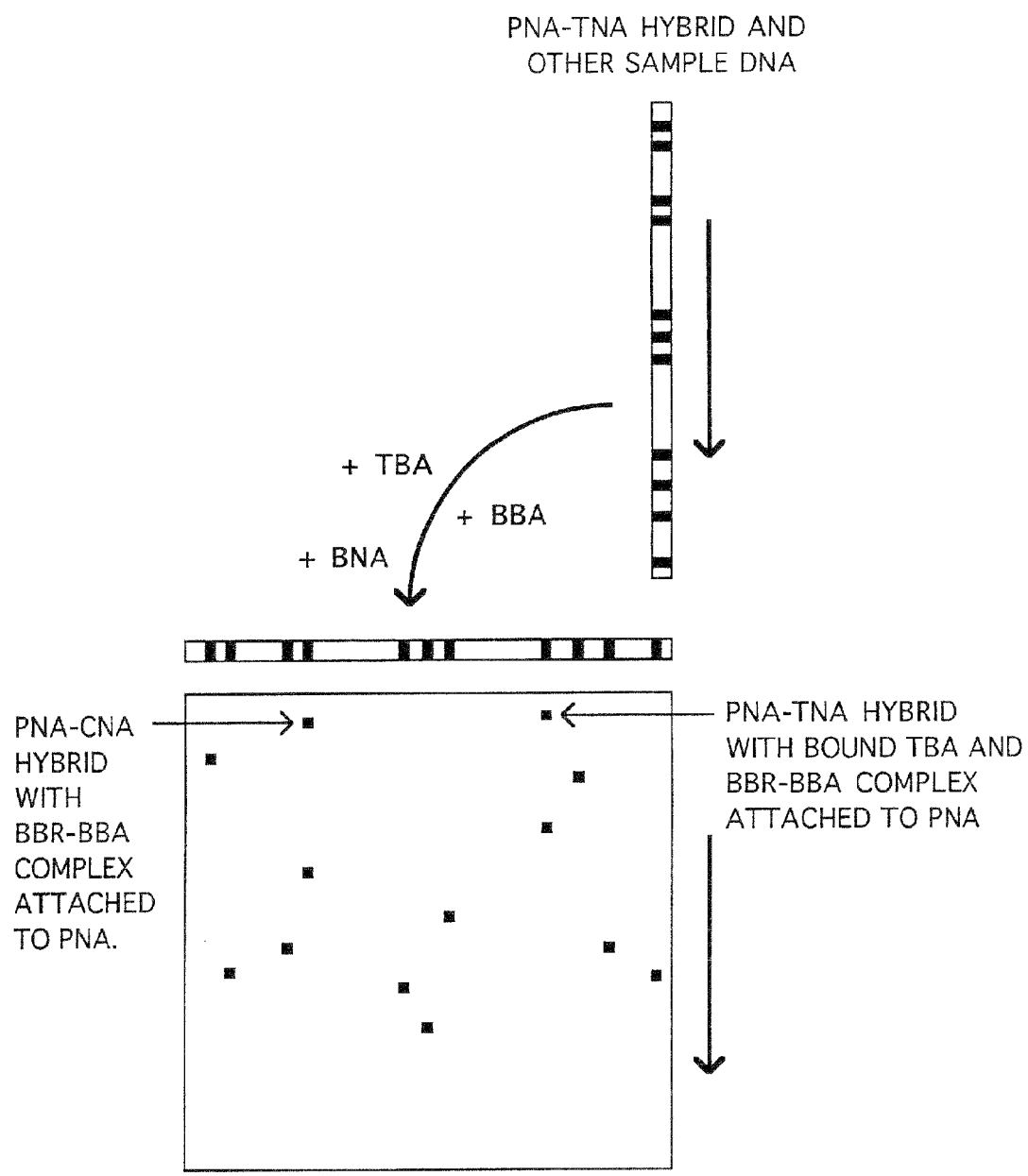

FIG. 12b is a schematic of TNA fractionation and enhanced shift in mobility due to binding of BBAs in addition to TBAs.

Figure 13:
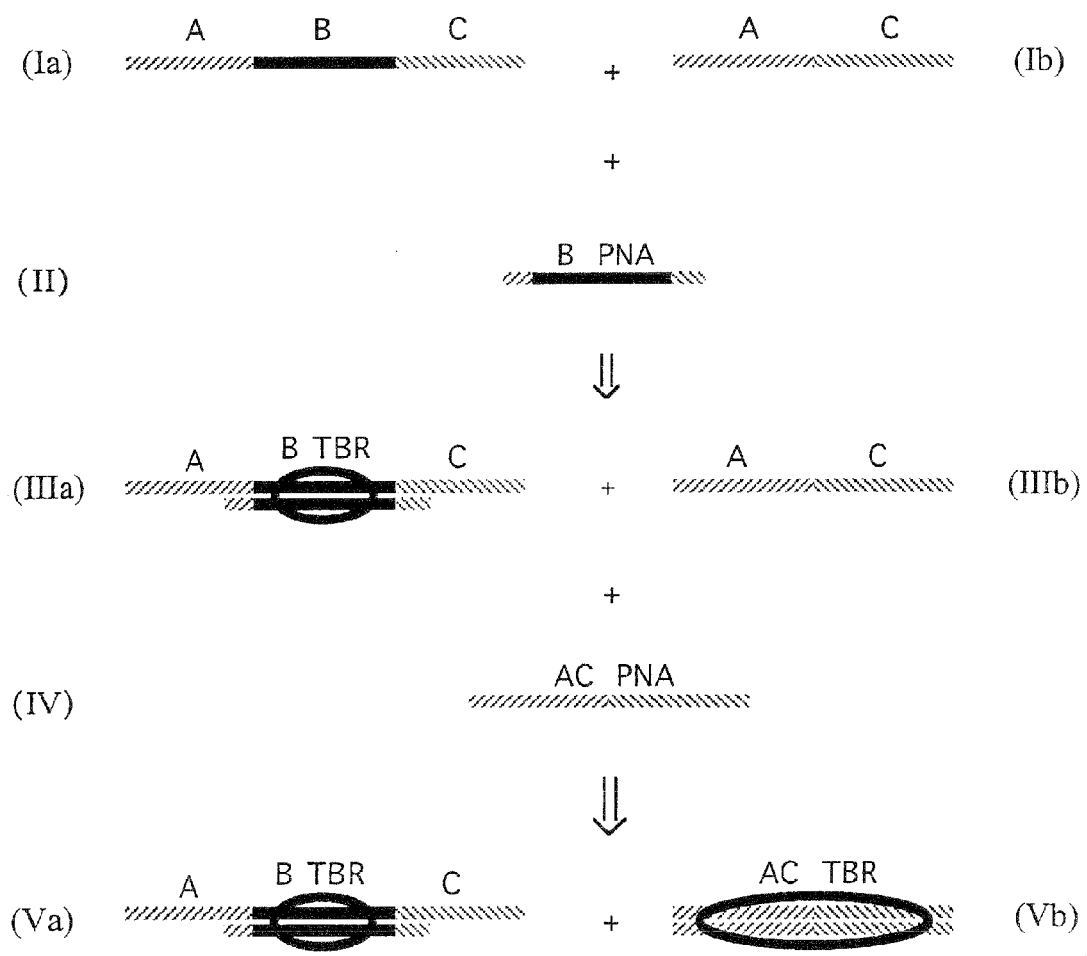

FIG. 13 shows a detection strategy for deletion sequences; an example of use of this strategy is for a human papillomavirus integration assay.

Figure 14:
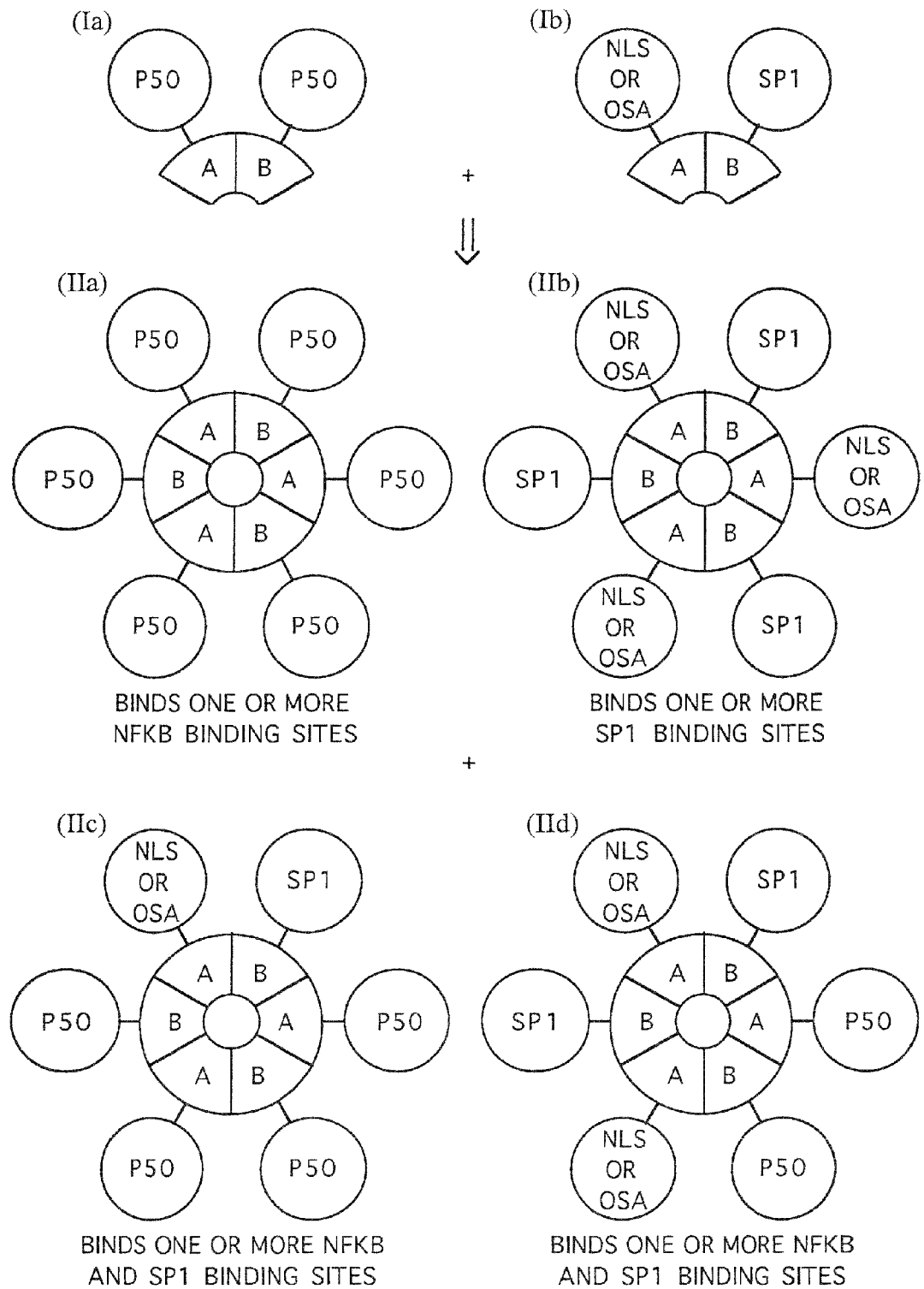

FIG. 14 shows assembly of higher order TBAs through use of nucleic acid recognition units, linker, assembly, and asymmetry sequences such that various Target Binding Assemblies specific to binding sites in the HIV LTR are formed.

Figure 15:
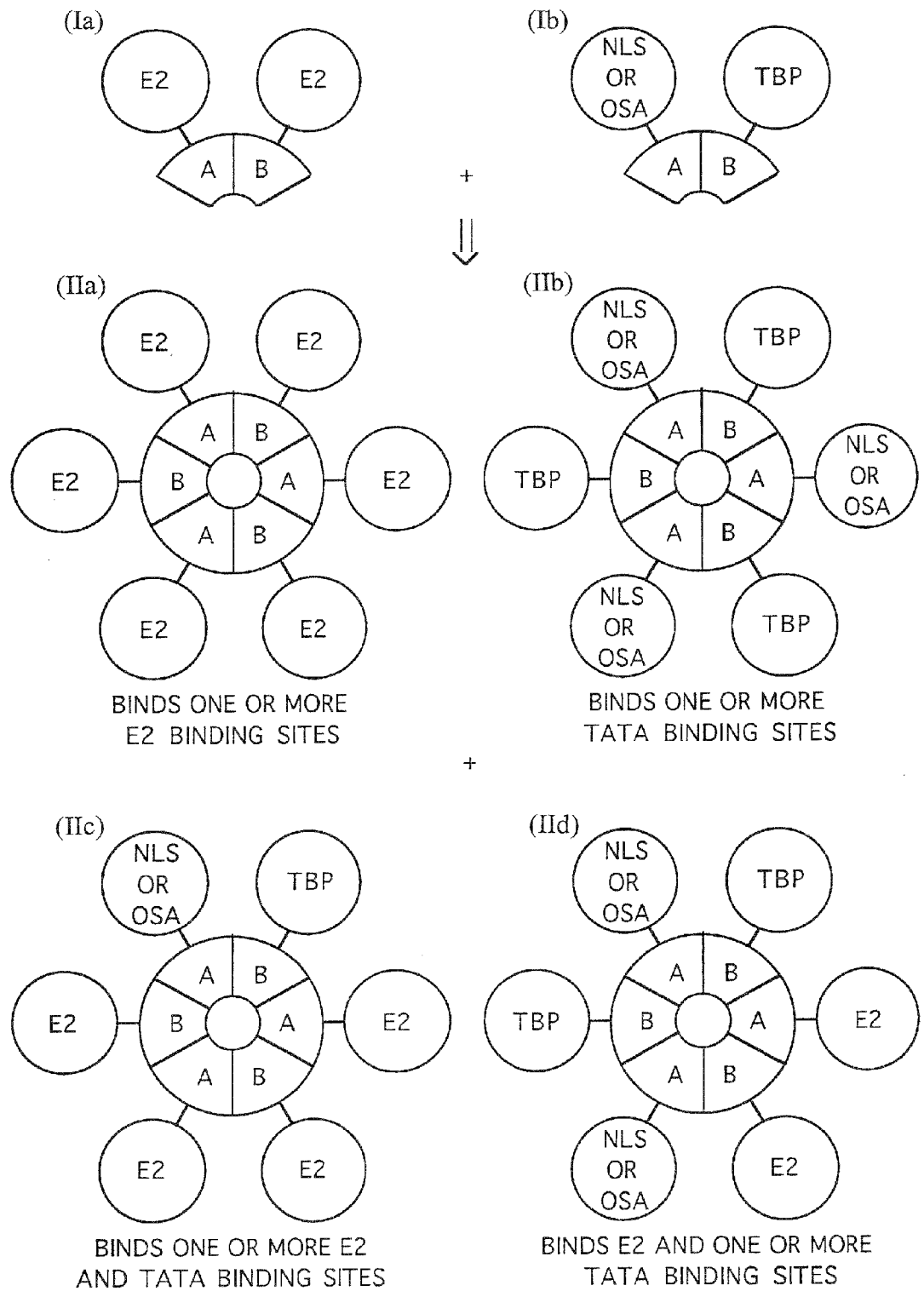

FIG. 15 shows assembly of higher order TBAs through use of DNA recognition units, linker, assembly, and asymmetry sequences such that various Target Binding Assemblies specific to binding sites in the HPV genome are formed.

Figure 16:
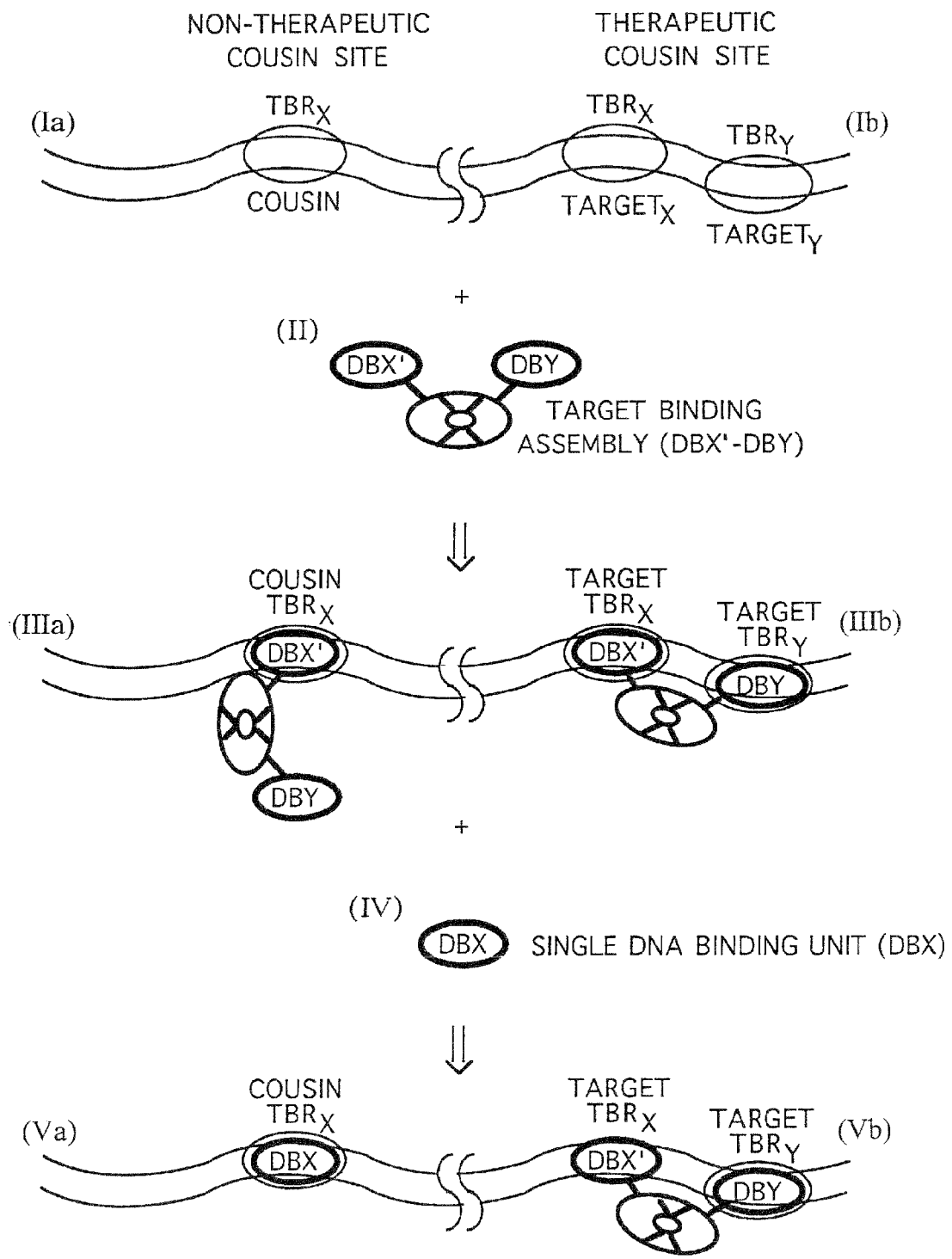

FIG. 16 shows the discrimination achieved by using a complex TBA and the ability of endogenous competitor target binding molecules to eliminate binding of the TBA to a cousin nucleic acid but not from the TNA which contains the appropriate orientation of more than one site recognized by the TBA.

Figure 17:
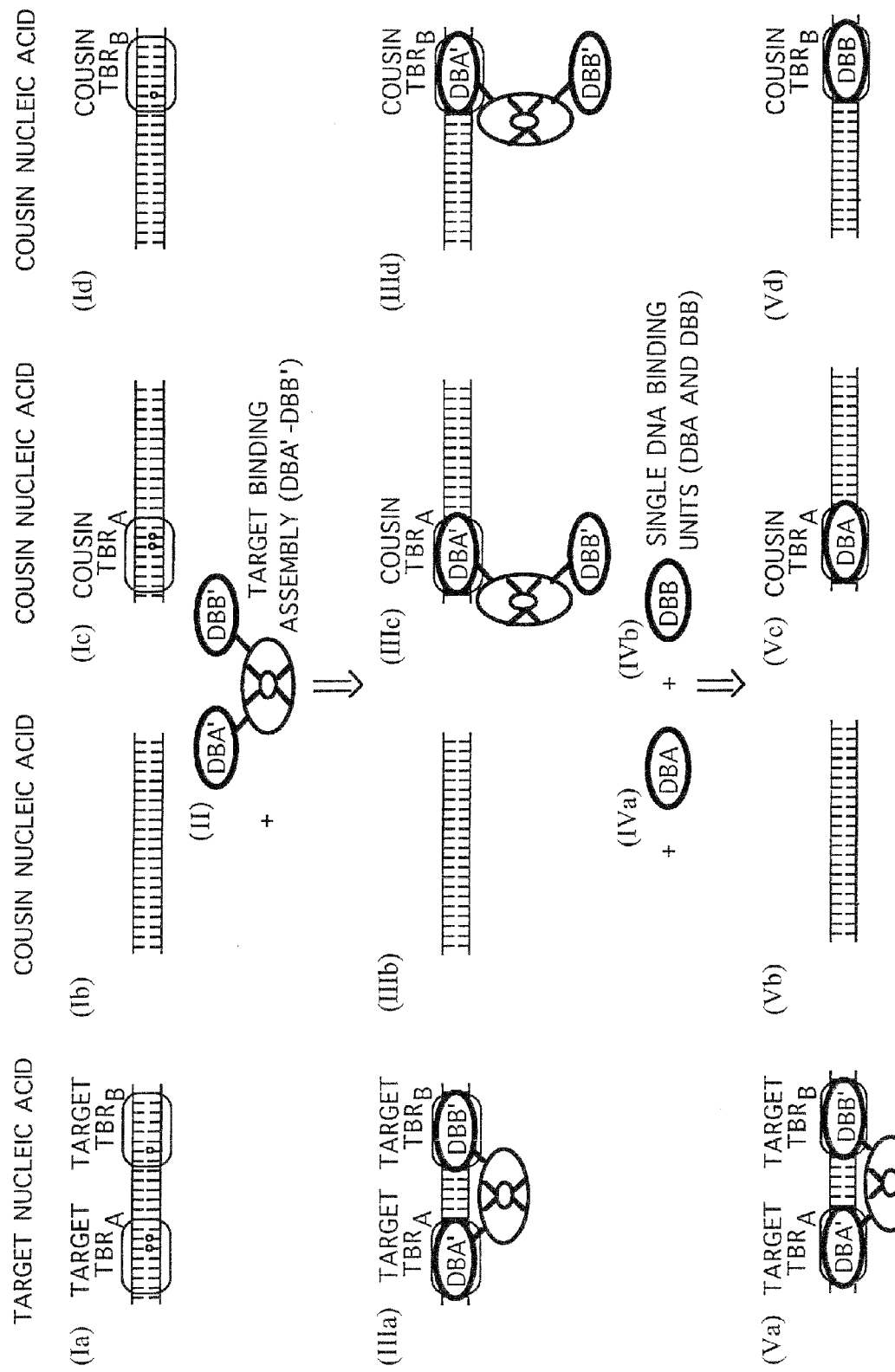

FIG. 17 shows the ability of a TBA to specifically be targeted to bind to sites of sequence mismatch and to preferentially bind those sites over cousin sites which do not contain all of the targeted mismatches.

BRIEF DESCRIPTION OF THE SEQUENCES

SEQ ID NO. 1 corresponds to FIG. 5-Ia-1 and shows the class I MHC NF-kB binding site.

SEQ ID NO. 2 corresponds to FIG. 5 (Ia) and shows the B2-microglobulin NF-kB binding site.

SEQ ID NO. 3 corresponds to FIG. 5 (Ia) and shows the kappa immunoglobulin NF-kB binding site.

SEQ ID NO. 4 corresponds to FIG. 5 (Ia) and shows one of the HIV NF-kB binding sites.

SEQ ID NO. 5 corresponds to FIG. 5 (Ia) and shows one of the HIV NF-kB binding sites.

SEQ ID NO. 6 corresponds to FIG. 5 (Ia) and shows the c-myc NF-kB binding site.

SEQ ID NO. 7 corresponds to FIG. 5 (Ia) and shows a double HIV NF-kB binding site.

SEQ ID NO. 8 corresponds to FIG. 5 (IIa) and shows a double I HIV NF-kB binding site.

SEQ ID NOS. 9-16 correspond to FIG. 5 (IIa) and show a double binding site with one site being an HIV NF-kB binding site, and the other site being an HIV SP1 binding site.

SEQ ID NOS. 17-18 correspond to FIG. 5 (IIa) and show a double HIV SP1 binding site.

SEQ ID NOS. 19-31 correspond to FIG. 5 (IIIa) and show a double HIV NF-kB binding site and an HIV SP1 binding site.

SEQ ID NOS. 32-33 correspond to FIG. 5 (IVa) and show a quadruple binding site where two sites are HIV NF-kB binding sites and two sites are HIV SP1 binding sites.

SEQ ID NO. 34 corresponds to FIG. 5 VIa) and shows a quintuple binding site where two sites are HIV NF-kB binding sites and three sites are HIV SP1 binding sites.

SEQ ID NO. 35 is an example of a 1/2 BBR, in this case the OL1, OL2 and OL3 elements of the bacteriophage lambda left operator, including intervening sequences.

SEQ ID NO. 36 is an example of a 1/2 BBR, in this case the OR3, OR2 and OR1 elements of the bacteriophage lambda right operator, including intervening sequences.

SEQ ID NO. 37 is the HIV LTR.

SEQ ID NO. 38 is a PNA complementary to PNA of the HIV LTR.

SEQ ID NO. 39 is a PNA complementary to a different PNA of the HIV LTR than SEQ ID NO. 38.

SEQ ID NO. 40 is a PNA complementary to part of the HIV LTR and it also contains a 1/2 BBR and an overhang sequence for polymerizing BNAs onto the PNA.

SEQ ID NO. 41 is a BNA complementary to the SEQ ID NO. 40 1/2 BBR.

SEQ ID NO. 42 is a BNA that will polymerize onto the SEQ ID NO. 41 BNA and which, with SEQ ID NOS. 40 and 41, creates a PstI recognition site.

SEQ ID NO. 43 is a BNA that is complementary to the SEQ ID NO. 42 BNA and which completes a BamHI recognition site.

SEQ ID NO. 44 is an HNA which has a BamHI recognition site that will hybridize with the BamHI recognition site created by SEQ ID NOS. 42 and 43 to the growing polymer.

SEQ ID NO. 45 is a second PNA which, like SEQ ID NO. 40, is complementary to part of the HIV LTR, but not to the same sequence as SEQ ID NO. 40. SEQ ID NO. 45 also encodes a 1/2 BBR and an overhang which will allow polymerization of BNAs starting with a Sph1 recognition site.

SEQ ID NOS. 46-62 are human papillomavirus (HPV) specific PNAs which, upon hybridization with HPV sequences, form TBRs which bind HPV DNA binding proteins.

SEQ ID NOS. 63-71 are NF-kB DNA recognition units for incorporation into TBAs.

SEQ ID NO. 72 is a nuclear localization sequence.

SEQ ID NO. 73 is a SP1 sequence recognition unit.

SEQ ID NO. 74 is a TATA binding protein recognition unit.

SEQ ID NOS. 75-84 are papillomavirus E2 DNA recognition units.

SEQ ID NOS. 85-92 are asymmetry sequences.

SEQ ID NO. 93 is an arabidopsis TATA binding protein recognition unit.

SEQ ID NO. 94 is an HPV-16-E2-1 DNA binding protein recognition unit.

SEQ ID NO. 95 is an HPV-16-E2-2 DNA binding protein recognition unit.

SEQ ID NO. 96 is an HPV-18-E2 DNA binding protein recognition unit.

SEQ ID NO. 97 is an HPV-33-E2 DNA binding protein recognition unit.

SEQ ID NO. 98 is a bovine papillomavirus E2 DNA binding protein recognition unit.

SEQ ID NOS. 99-102 are exemplary linker sequences.

SEQ ID NO. 103 is an exemplary nuclear localization signal sequence (NLS).

SEQ ID NOS. 104-108 are exemplary chaperone sequences.

SEQ ID NOS. 109-116 are exemplary assembled TBA sequences.

SEQ ID NO. 117 is a consensus NF-kB binding site.

SEQ ID NO. 118 an HIV Tat amino acid sequence.

Abbreviations

Abbreviations

 single stranded nucleic acid

 double-stranded nucleic acid

 binding region on nucleic acid

| | |
|---|---|
| | no support or indicators, or solid support, or other means of localization, including, but not limited to, attachment to beads, polymers, and surfaces, or indicators = OSA |
| BA | booster binding assembly |
| BBR | booster binding region |
| BNA | booster nucleic acid |
| CNA | cousin nucleic acid |
| 1/2 BBR | single-stranded region which, when hybridized to the complementary sequence from an HNA or a BNA, can bind a BBA |
| 1/2 TBR | single-stranded region of the PNA which, when hybridized to the complementary sequence from a TNA, can bind a TBA |
| OSA | optional support or attachment, circle with box |
| PNA | probe nucleic acid |
| TBA | target binding assembly |
| TBR | target binding region |
| TNA | target nucleic acid |
| HNA | Hairpin Nucleic Acid |

Definitions

It should also be understood from the disclosure which follows that when mention is made of such terms as target binding assemblies (TBAs), booster binding assemblies (BBAs), DNA binding proteins, nucleic acid binding proteins or RNA binding proteins, what is intended are compositions comprised of molecules which bind to DNA or RNA target nucleic acid sequences (TNAs) irrespective of the specificity of the category of binding molecules from which they are derived. Thus, for example, a TBA adapted to bind to human immunodeficiency virus sequences may be most similar to an NF-KB transcriptional factor which typically binds DNA sequences. However, as used herein, it will be understood that the TBA may be adapted for optimal use to bind to RNA sequences of a particular sequence composition or conformation.

The fidelity of the detection method disclosed herein depends in large measure on the selective binding of TBAs and BBAs to particular nucleic acid motifs. It should be understood throughout this disclosure that the basis of TBA and BBA discrimination of TNAs from related sequences (cousin nucleic acids or CNAs) may be the formation of precise probe nucleic acid (PNA)-target nucleic acid (TNA) hybrid segments (PNA-TNA hybrids). However, the basis of discrimination may just as well be the formation of a particular conformation, and may not require the complete absence of mismatched-base pairing in the TNA-PNA hybrid. Accordingly, the basis of TBA or BBA operation should be understood throughout to depend on discrimination of any property unique to the TNA-PNA hybrid as opposed to any properties displayed by any PNA-CNA hybrids that may be formed in a test sample contacted with a given PNA.

DETAILED DISCLOSURE OF THE INVENTION

The present invention provides a method for specifically identifying a target nucleic acid (TNA) in a sample through the use of target binding assemblies (TBAs) which incorporate specific nucleic acid binding proteins. By using probe nucleic acids (PNAs) specific to a given TNA sequence, and a TBA which is specific to the duplex target binding region (TBR) formed upon formation of hybrid TNA-PNA sequences, a stable TBA-TNA-PNA complex is formed. By additionally providing specific amplifiable sequences in the PNA, in addition to sequences which specifically contribute to the formation of the TBR recognized by the TBA, the binding of the PNA to the TNA is detected and the detection amplified. For this purpose, any of a number of nucleic acid amplification systems, including polymerase chain reaction, or the use of branched DNA, each branch of which contains a detectable label, may be used. In particular, a novel method of amplification is described herein where the amplifiable portion of the PNA contains sequences onto which booster nucleic acids (BNA s) may be polymerized. Upon formation of each BNA-PNA hybrid, a booster binding region (BBR) is formed to which a booster binding assembly (BBA) binds specifically. If detectably labeled, the BBAs or BNAs provide essentially unlimited amplification of the original TNA-PNA binding event.

According to this invention, the TNA will be understood to include specific nucleic acid sequences. The TBA will be understood to be any molecular assembly which can specifically and tightly bind to a formed TNA-PNA hybrid. The TBA will contain one or more molecules whose sequences are sufficient to bind to the TBR. Nucleic acid binding domains which are known can either be used directly as components of the TBA or modified according to the teachings provided herein. The most readily available molecules with such sequences are the DNA-binding domains of DNA-binding proteins. Specifically, many DNA or RNA binding proteins are known which can either be used directly as the known, unmodified protein, or the TBA may be a nucleic acid binding protein, modified according to the specific teachings provided herein. In the latter case, specific modifications that are desirable would include optimization of binding affinities, removal of unwanted activities (such as nuclease activity and reorganization of the TBA in the presence of other molecules with an affinity for components of the TBA), optimization of selectivity of a target sequence over closely related sequences, and optimization of stability.

Examples of DNA binding proteins which could be used according to this invention are the DNA-binding portions of the transcription factor NF-kB (p50 and p65), NF-IL6, NF-AT, rel, TBP, the papilloma virus' E2 protein, sp1, the repressors cro and CI from bacteriophage lambda, and like proteins are well known proteins whose DNA binding portion has been isolated, cloned, sequenced, and characterized. In addition, any other DNA-binding protein or portion of a protein that is necessary and sufficient to bind to a TBR hybrid or a BBR is included. This includes proteins or portions of wild-type proteins with altered DNA binding activity as well as protein created with altered DNA-binding specificity, such as the exchange of a DNA-binding recognition helix from one protein to another. In addition, proteins which exhibit nucleic acid binding and other nucleic acid functions, such as restriction endonucleases, could be used as the nucleic acid binding function. Proteins which bind to target regions in DNA-RNA hybrids as well as RNA-RNA hybrids are included. (See, for example, Shi 1995, DeStefano 1993, Zhu 1995, Gonzales 1994, Salazar 1993, Jaishree 1993, Wang 1992, Roberts 1992, Kainz 1992, Salazar 1993(b)). The binding assemblies may be constructed with the use of a molecule which chaperones portions of the binding assembly so that specific component combinations and geometries can be achieved. This molecule is designated here as a PILOT. Pilots can be comprised of proteins or any combination of organic and inorganic materials which achieve the combinatorial selection and/or to induce specific geometries between members of the TBA or BBAs. A chaperone is a stable scaffold upon which a TBA or BBA may be constructed such that the correct conformation of the TBA or BBA is provided while at the same time eliminating undesirable properties of a naturally occurring nucleic acid binding protein. As a specific example of this embodiment, a modified version of the pleiotropic transcription factor, NF-kB, is provided using a modified bacteriophage lambda cro protein as the chaperone. Each NF-kB binding dimer retains the picomolar binding affinity for the NF-kB binding site while at the same time the binding assembly presents several advantageous manufacturing, stability, and specificity characteristics.

In view of the foregoing, the various aspects and embodiments of this invention are described below in detail.

1. The Probe Nucleic Acids (PNAs) and their preparation. The PNAs of the present invention comprise at least three principal parts joined together. With reference to FIG. 1(I) of the drawings, the first part of the PNA is one or more sequences of bases, designated "1/2 TBR." With reference to FIG. 1(I and IIa) of the drawings, the 1/2 TBR in the PNA is complementary to a sequence of interest in a sample, the TNA containing a 1/2 TBR. With reference to FIG. 1(IIIa) of the drawings, the TNA, when added to the PNA under hybridizing conditions, forms a PNA-TNA hybrid containing a TBR. With reference to FIG. 1(I) of the drawings, the second part of the PNA is a sequence of bases, designated "1/2 BBR." With reference to FIG. 1(I, IIb, IIc, and IVa) of the drawings, the 1/2 BBR in the PNA is complementary to a 1/2 BBR contained in a BNA or a HNA. With reference to FIG. 1(IIIb, IIIc, and Va) of the drawings, the BNA or HNA, when added to the PNA under hybridizing conditions, forms a PNA-BNA hybrid or PNA-HNA hybrid, respectively, containing a BBR. With reference to FIG. 1(I) of the drawings, the third part of the PNA is the OSA, designated by a circle with a box around it. The OSA is no support and/or an indicator, or solid support, or other means of localization, including but not limited to, attachment to beads, polymers, and surfaces and/or indicators which is/are covalently attached to, or non-covalently, but specifically, associated with the PNA. The OSA may be an atom or molecule which aids in the separation and/or localization such as a solid support binding group or label which can be detected by various physical means including, but not limited to, adsorption or imaging of emitted particles or light. Methods for attaching indicators to oligonucleotides or for immobilizing oligonucleotides to solid supports are well known in the art (see Keller and Manak, supra, herein incorporated by reference).

The PNA of the present invention can be prepared by any suitable method. Such methods, in general, will include oligonucleotide synthesis and cloning in a replicable vector. Methods for nucleic acid synthesis are well-known in the art. When cloned or synthesized, strand purification and separation may be necessary to use the product as a pure PNA. Methods of preparing RNA probes are well known (see for example Blais 1993, Blais 1994, which uses in vitro transcription from a PCR reaction incorporating a T7 RNA polymerase promoter).

The length and specific sequence of the PNA will be understood by those skilled in the art to depend on the length and sequence to be detected in a TNA, and the strictures for achieving tight and specific binding of the particular TBA to be used (see discussion on TBAs below). In general, PNAs of sequence lengths between about 10 and about 300 nucleotides in length are adequate, with lengths of about 15-100 nucleotides being desirable for many of the embodiments specifically exemplified herein.

It should also be understood that the PNA may be constructed so as to contain more than one 1/2 TBR and to produce more than one TBR for one or more TBAs, same or different, as well as complex TBRs recognized by novel duplex and multiplex TBAs (see description below regarding these novel TBAs) upon hybridization of the PNAs and TNAs. FIG. 5 illustrates specific PNAs which contain one or more 1/2 TBRs. Specific sequences which correspond to the 1/2 TBR sequences illustrated in FIG. 5 (Ia, IIa, IIIa, IVa, and Va) are SEQ ID NOS. 1-34 (see Description of Sequences above).

As shown in FIGS. 2a and 2b, the PNA, containing a 1/2 TBR, may be hybridized with one or more BNAs (see description below) and the chain of BNAs polymerized to any desired potential length for amplification of the TNA-PNA hybridization event. Preferably, between about 0 and about 10 1/2 BBRs will be present in the PNA.

As shown in FIGS. 6a, 6b, 6c, 6d and 6e, the PNA may contain several 1/2 TBRs, same or different, which can hybridize with several 1/2 TBRs in a TNA. Each time a 1/2 TBR in the PNA matches a 1/2 TBR in a TNA, a Target Binding Region, TBR, is formed which can bind a TBA. Furthermore, it is not essential that all of the TBRs be on a single, contiguous PNA. Thus, in one embodiment of the invention, two different PNAs are used to detect sequences on a particular TNA. As an illustration of this aspect of the invention, FIG. 7 shows one representation of the human immunodeficiency virus (HIV) long terminal repeat (LTR). As is known in the art, the HIV LTR comprises two NF-kB binding sites and three SP1 binding sites, in close proximity, wherein NF-kB and SP1 are known DNA binding proteins. FIG. 7 provides two PNAs, PNA1 (SEQ ID NO. 38) and PNA2 (SEQ ID NO. 39), each of which is complementary to the opposite strand shown as a TNA (SEQ ID NO. 37), which shows the two NF-kB binding sites and the three SP1 binding sites of the HIV LTR. According to this aspect of the invention, PNA1 specifically hybridizes with that section of the TNA shown in FIG. 7 with bases underscored with a "+" symbol, while PNA2 specifically hybridizes with that section of the TNA shown in FIG. 7 with bases underscored with an "=" symbol. Each of PNA1 or PNA2 may also contain sequences (indicated by the symbols "#" or "*") which will hybridize with a BNA's 1/2 BBR sequences (see below). In addition, each of PNA1 and PNA2 may be differentially tagged with an OSA, such as a fluorophore such as a fluorescein or a rhodamine label, which would allow confirmation that both probes have become bound to the TNA. If only one label or neither label is detected, it is concluded that the TNA is not present in the sample being tested.

In a further aspect of the embodiment shown in FIG. 7, a method for altering the specificity of the instant assay method is shown. By changing the length of the gap between PNA1 and PNA2, such that the region of TNA remaining unhybridized is altered, one practicing this invention is able to alter the discrimination of the assay.

In order to more clearly exemplify this aspect of the invention, it is necessary to emphasize that the TBR may have a helical structure. Thus, while PNA1 creates TBRs on one "face" of the helix, PNA2 creates a TBR on either the same or a different face of the helix, depending on the distance between the middle of each TBR (underlined in FIG. 7). If the middle of each binding site is an integral product of 10.5 bases apart, the TBRs will be on the same side of the helix, while non-integer products of 10.5 bases apart would place the TBRs on opposite sides of the helix. In this fashion, any cooperativity in binding by the TBA recognizing the PNA1 TBR and the TBA recognizing the PNA2 TBR can be manipulated (see Hochschild, A., M. Ptashne [1986] *Cell* 44:681-687, showing this effect for the binding of bacteriophage lambda repressor to two different operator sites located at different distances from each other in a DNA helix). As described by Perkins et al. ([1993] *EMBO J.* 12:3551-3558), cooperativity between NF-kB and the SP1 sites is required to achieve activation of the HIV LTR. However, for the purpose of the instant invention, the double NF-kB-triple SP1 binding site motif in the HIV LTR may be taken advantage of by providing a single, novel binding protein capable of binding both sites simultaneously, but only if the spacing between the sites is geometrically feasible. This is controlled both by the structure of the selected TBA and by the PNAs used. Thus, in the embodiment exemplified in FIG. 7, the two probes may be used with a large enough interprobe region of single-stranded DNA remaining such that, even if the NF-kB and SP1 binding sites are on opposite sides of the helix, the single-stranded region between the probes provides a sufficiently flexible "hinge" so that the DNA can both bend and twist to accommodate the geometry of the TBA. Alternatively, a more stringent assay may be designed by narrowing the interprobe distance such that the DNA may only bend, but not twist. Finally, the probes may be so closely spaced, or a single PNA used, such that the DNA can only bend but not twist. Thus, this figure exemplifies and enables the production of detection systems with any given desired degree of discrimination between target nucleic acids having similar sequences, but different juxtapositions of these sequences.

In terms of a diagnostic or forensic kit for HIV, those skilled in the art would understand that the aforementioned aspects of this invention allow for the tailoring of the components of the diagnostic or forensic kit to match what is known at any given time about the prevalent strains of HIV or another pathogen or disease condition. It will also be appreciated by those skilled in the art that, while detection of HIV infection is not the only utility of the instant invention, due to the mutability of the HIV genome, it is probably one of the most complex test environments for such a diagnostic. It is precisely in such a mutable environment, however, where the flexibility of the instant method, coupled with its ability to discriminate between very closely related sequences, may be most clearly appreciated. In less mutable environments, some of the sophistication to which this invention is amenable need not be utilized. Thus, in a diagnostic kit for papillomavirus infection, all of the discrimination characteristics of the TBA-TBR interaction are available, along with the ability to amplify the signal using the BNAs and BBAs, but a single, simple PNA, such as any one of SEQ ID NOS. 46-62, may be used which identifies unique papillomavirus sequences, which also are known to bind to a TBA such as the papillomavirus E2 protein or truncated DNA binding portions thereof (see Hegde et al. [1992] *Nature* 359:505-512; Monini et al. [1991] *J. Viral.* 65:2124-2130).

In applying the instant method to the detection of a particular TNA for the purposes of assessing whether certain nucleic acids are present which are associated with the progression of melanoma, hepatoma, breast, cervical, lung, colon, prostate, pancreatic or ovarian cancers, the TNA may be obtained from biopsy materials taken from organs and fluids suspected of containing the cancerous cells. For the detection of genetic deficiencies, the TNA may be obtained from patient samples containing the affected cells. For detection of fermentation contaminants and products in the manufacture of food, chemical or biotechnology products or in the bioremediation of wastes, the TNA may be obtained from samples taken at various stages in the fermentation or treatment process. For detection of food or drug pathogens or contaminants, the TNA sample may be obtained from the food or drug, swabs of food or surfaces in contact with the food, fluids in contact with the food, processing materials, fluids and the like associated with the manufacture of or in contact with the food, drug, or biological samples taken from those in contact with the food or drug or the like.

2. The Booster Nucleic Acids (BNAs), Booster Binding Regions (BBRs) and their preparation. The BNAs of the present invention are comprised of at least one or more 1/2 BBRs coupled to an OSA. The 1/2 BBRs can hybridize to complementary 1/2 BBRs contained in the PNA, other BNAs or an HNA.

With reference to FIG. 1(I, IIb and IIIb) of the drawings, the simplest BNA is comprised of two parts. With reference to FIG. 1(IIb) of the drawings, the first part of the simplest BNA is a sequence of bases which is complementary to the sequence in the PNA which is designated "1/2 BBR." With reference to FIG. 1(IIb) of the drawings, the second part of the simplest BNA is the OSA, designated by a circle with a box around it. The OSA is no support and/or indicator, or solid support, or other means of localization, including but not limited to, attachment to beads, polymers, and surfaces and/or indicators which are covalently attached to, or non-covalently, but specifically, associated with the BNA.

With reference to FIGS. 2a and 2b (II and III) of the drawings, the BNA may contain more than one 1/2 BBR sequence. The BNA illustrated in FIG. 3a(II) contains a sequence which is complementary to the PNA illustrated in FIG. 3a(I) and two other 1/2 BBR sequences. The BNA illustrated in FIG. 3a(III) contains two 1/2 BBR sequences which are complementary to two of the 1/2 BBR sequences in the BNA illustrated in FIG. 3a (II), plus up to "n" additional 1/2 BBRs for polymerization of additional BNAs.

Under hybridizing conditions, the BNA illustrated in FIG. 3a(II), when combined with the PNA illustrated in FIG. 3a (I), creates the PNA-BNA hybrid illustrated in FIG. 3(IVa) containing a BBR and an unhybridized extension with two additional 1/2 BBR sequences or "booster" sequences. The BBRs created by said hybridization can be identical, similar or dissimilar in sequence. The BBRs created by said hybridization can bind identical, similar or dissimilar BBAs (see below). The BNAs may have prepared analogously to the PNAs.

Under hybridizing conditions, the BNA-BNA hybrid illustrated in FIG. 3a(IVb), when combined with the PNA illustrated in FIG. 3a(Vb), creates the PNA-BNA hybrid illustrated in FIG. 3b(VI) containing a BBR, two additional BNA-BNA hybrids containing BBRs, and an unhybridized extension with an additional 1/2 BBR sequence, a "booster" sequence. The BBRs created by said hybridization can be identical, similar or dissimilar in sequence. The BBRs created by said hybridization can bind identical, similar or dissimilar BBAs (see below). The BNAs may be prepared in a fashion analogous to preparation of the PNAs.

3. The Target Nucleic Acids (TNAs) and their preparation. The first step in detecting and amplifying signals produced through detection of a particular TNA according to the present method is the hybridization of such target with the PNA in a suitable mixture. Such hybridization is achieved under suitable conditions well known in the art.

The sample suspected or known to contain the intended TNA may be obtained from a variety of sources. It can be a biological sample, a food or agricultural sample, an environmental sample and so forth. In applying the instant method to the detection of a particular TNA for the purposes of medical diagnostics or forensics, the TNA may be obtained from a biopsy sample, a body fluid or exudate such as urine, blood, milk, cerebrospinal fluid, sputum, saliva, stool, lung aspirates, throat or genital swabs and the like. In addition, detection may be in situ (see for example Embretson 1993; Patterson 1993; Adams 1994).

Accordingly, PNAs specific to vertebrates (including mammals and including humans) or to any or all of the following microorganisms of interest may be envisioned and used according to the instant method:

Corynebacteria
    *Corynebacterium diphtheria*
Bacillus
    *Bacillus thuringiensis*
Pneumococci
    *Diplococcus pneumoniae*
Streptococci
    *Streptococcus pyogenes*
    *Streptococcus salivarius*
Staphylococcus
    *Staphylococcus aureus*
    *Staphylococcus albus*
Pseudomonas
    *Pseudomonas stutzen*
Neisseria
    *Neisseria meningitidis*
    *Neisseria gonorrhea*
Enterobacteriaceae
    *Escherichia coli*
    *Aerobacteria aerogenes*
    *Klebsiella pneumoniae* The coliform bacteria
    *Salmonella typhosa*
    *Salmonella choleraesuis* The Salmonellae
    *Salmonella typhimurium*
    *Shigellae dysenteriae*
    *Shigellae schmitzii*
    *Shigellae arabinotarda*
    *Shigellae flexneri* The Shigellae
    *Shigellae boydii*
    *Shigellae sonnei*
Other enteric bacilli
    *Proteus vulgaris*
    *Proteus mirabilis Proteus* species
    *Proteus morgani*
    *Pseudomonas aeruginosa*
    *Alcaligenes faecalis*
    *Vibrio cholerae*
Hemophilus-Bordetella group
    *Hemophilus influenza, H. ducryi*
    *Hemophilus hemophilus*
    *Hemophilus aegypticus*
    *Hemophilus parainfluenzae*
    *Bordetella pertussis*
Pasteurellae
    *Pasteurella pestis*
    *Pasteurella tulareusis* Brucellae
    *Brucella melitensis*
    *Brucella abortus*
    *Brucella suis*
Aerobic Spore-Forming Bacilli
    *Bacillus anthracis*
    *Bacillus subtilis*
    *Bacillus megaterium*
    *Bacillus cereus*
Anaerobic Spore-Forming Bacilli
    *Clostridium botulinum*
    *Clostridium tetani*
    *Clostridium perfringens*
    *Clostridium novyi*
    *Clostridium septicum*
    *Clostridium histolyticum*
    *Clostridium tertiurn*
    *Clostridium bifermentans*
    *Clostridium sporogenes*

Mycobacteria
  *Mycobacterium tuberculosis hominis*
  *Mycobacterium bovis*
  *Mycobacterium avium*
  *Mycobacterium leprae*
  *Mycobacterium paratuberculosis*
*Actinomycetes* (fungus-like bacteria)
  *Actinomyces isaeli*
  *Actinomyces Bovis*
  *Actinomyces naeslundii*
  *Nocardia asteroides*
  *Nocardia brasiliensis*
The Spirochetes
  *Treponema pallidum*
  *Treponema pertenue*
  *Treponema carateum*
  *Spirillum minus*
  *Streptobacillus moniliformis*
  *Borrelia recurrens*
  *Leptospira icterohemorrhagiae*
  *Leptospira canicola*
Trypanasomes
*Mycoplasmas*
  *Mycoplasma pneumoniae*
Other pathogens
  *Listeria monocytogenes*
  *Erysipelothrix rhusiopathiae*
  *Streptobacillus moniliformis*
  *Donvania granulomatis*
  *Bartonella bacillformis*
Rickettsiae (bacteria-like parasites)
  *Rickettsia prowazekii*
  *Rickettsia mooseri*
  *Rickettsia rickettsii*
  *Rickettsia conori*
  *Rickettsia australis*
  *Rickettsia sibiricus*
  *Rickettsia akari*
  *Rickettsia tsutsugamushi*
  *Rickettsia burnetti*
  *Rickettsia quintana*
Chlamydia (unclassifiable parasites bacterial/viral)
  Chlamydia agents (naming uncertain)
Fungi
  *Cryptococcus neoformans*
  *Blastomyces dermatidis*
  *Histoplasma capsulatum*
  *Coccidioides immitis*
  *Paracoccidioides brasiliensis*
  *Candida albicans*
  *Aspergillus fumigatus*
  *Mucor corymbifera* (*Absidia corymbifera*)
  *Rhizopus oryzae*
  *Rhizopus arrhizus* Phycomycetes
  *Rhizopus nigricans*
  *Sporotrichum schenkii*
  *Flonsecaea pedrosoi*
  *Fonsecaea compact*
  *Fonsecacae dermatidis*
  *Cladosporium carrioni*
  *Phialophora verrucosa*
  *Aspergillus nidulans*
  *Madurella mycetomi*
  *Madurella grisea*
  *Allescheria boydii*
  *Phialophora jeanselmei*
  *Microsporum gypsum*
  *Trichophyton mentagrophytes*
  *Keratinomyces ajelloi*
  *Microsporum canis*
  *Trichophyton rubrum*
  *Microsporum adouini*
Viruses
  Adenoviruses
  Herpes Viruses
    Herpes simplex
    Varicella (Chicken pox)
    Herpes zoster (Shingles)
    Virus B
    Cytomegalovirus
  Pox Viruses
    Variola (smallpox)
    Vaccinia
    Poxvirus bovis
    Paravaccinia
    Molluscum contagiosum
  Picornaviruses
    Poliovirus
    Coxsackievirus
    Echoviruses
    Rhinoviruses
  Myxoviruses
    Influenza (A, B, and C)
    Parainfluenza (1-4)
    Mumps virus
    Newcastle disease virus
    Measles virus
    Rinderpest virus
    Canine distemper virus
    Respiratory syncytial virus
    Rubella virus
  Arboviruses
    Eastern equine encephalitis virus
    Western equine encephalitis virus
    Sindbis virus
    Chikugunya virus
    Semliki forest virus
    Mayora virus
    St. Louis encephalitis virus
    California encephalitis virus
    Colorado tick fever virus
    Yellow fever virus
    Dengue virus
  Reoviruses
    Reovirus types 1-3
  Retroviruses
    Human immunodeficiency viruses (HIV)
    Human T-cell lymphotrophic virus I & II (HTLV)
  Hepatitis
    Hepatitis A virus
    Hepatitis B virus
    Hepatitis nonA-nonB virus
    Hepatitis, C, D, E
  Tumor viruses
    Rauscher leukemia virus
    Gross virus
    Maloney leukemia virus
    Human papilloma viruses It would be understood by one of skill in the art that it is generally required to treat samples suspected of containing a particular TNA in such a fashion as to produce fragments that can easily hybridize with the PNA. It may be necessary to treat the test sample to effect release of or to extract the TNA for hybridization, such as by exposing blood or other cells to a hypotonic environment, or otherwise disrupting the sample using more vigorous means. When the TNA is thought to be present in double stranded form, it would naturally be desirable to separate the strands to render the TNA hybridizable in single stranded form by methods well known in the art, including but not limited to heating or limited exposure to alkaline conditions which may be neutralized upon addition of the single stranded PNA to allow hybridization to occur. Methods for preparing RNA targets are well known (see Waterhouse 1993, Mitchell 1992).

Fragmentation of nucleic acid samples containing TNAs is usually required to decrease the sample viscosity and to increase the accessibility of the TNAs to the PNAs. Such fragmentation is accomplished by random or specific means known in the art. Thus, for example, specific nucleases known to cut with a particular frequency in the particular genome being analyzed, may be used to produce fragments of a known average molecular size. In addition, other nucleases, phosphodiesterases, exonucleases and endonucleases, physical shear and sonication are all methods amenable for this purpose. These processes are well known in the art. The use of restriction enzymes for the purpose of DNA fragmentation is generally preferred. However, DNA can also be fragmented by a variety of chemical means such as the use of the following types of reagents: EDTA-Fe(II) (according to Stroebel et al. [1988] *J. Am. Chem. Soc.* 110:7927; Dervan [1986] *Science* 232:464); Cu(II)-phenanthroline (according to Chen and Sigman [1987] *Science* 237:1197); class IIS restriction enzyme (according to Kim et al. [1988] *Science* 240:504); hybrid DNAse (according to Corey et al. [1989] *Biochem.* 28:8277); bleomycin (according to Umezawa et al. [1986] *J. Antibiot.* (Tokyo) Ser. A, 19:200); neocarzinostatin (Goldberg et al. [1981] *Second Annual Bristol-Myers Symposium in Cancer Research*, Academic Press, New York, p. 163); and methidiumpropyl-EDTA-Fe(II) (according to Hertzberg et al. [1982] *J. Am. Chem. Soc.* 104:313). Removal of proteins, as by treatment with a protease, is also generally desirable and methods for effecting protein removal from nucleic acid samples, without appreciable loss of nucleic acid, are well known in the art.

The TNAs of the present invention should be long enough so that there is a sufficient amount of double-stranded hybrid flanking the TBR so that a TBA can bind unperturbed by the unligated fragment ends. Typically, fragments in the range of about 10 nucleotides to about 100,000 nucleotides, and preferably in the range of about 20 nucleotides to about 1,000 nucleotides are used as the average size for TNA fragments. Examples of specific TNA sequences that could be detected are sequences complementary to the PNA sequences described herein for detection of normal cellular, abnormal cellular (as in activated oncogenes, integrated foreign genes, genetically defective genes), and pathogen-specific nucleic acid sequences, for which specific nucleic acid binding proteins are known, or which can be produced according to methods described in this disclosure. With reference to FIG. 7, a specific HIV-related TNA is shown as SEQ ID NO. 37.

4. Extensions to the PNA using BNAs, their preparation, and signal amplification. Under hybridizing conditions, BNAs can be added that hybridize to the PNAs, PNA-BNA hybrids, BNAs and/or BNA-BNA hybrids. The aforementioned additions can be made in a non-vectorial polymeric fashion or in a vectorial fashion, with a known order of BNAs.

With reference to FIG. 2a, a simple booster is presented. A booster polymer is produced by adding two BNAs, illustrated in FIG. 2a(Ib and Ic), which when combined under hybridizing conditions with the PNA, form PNA-BNA-BNA hybrids, comprised of the PNA and "booster" extensions", illustrated in FIG. 2a(IIa,IIb,IIc and IId) leaving at least one unpaired 1/2 BBR sequence. Each unpaired 1/2 BBR sequence, illustrated in FIG. 2a(IIa, IIb, IIc, IId) can hybridize with additional BNAs to form additional "booster" extensions. Each unpaired 1/2 BBR sequence, illustrated in FIG. 2a(IIa,IIb,IIc and IId) can hybridize with added HNAs, illustrated in FIG. 2a(IIIa and IIIb). The hybridization of the HNAs, which cannot hybridize additional BNAs, acts to "cap" the addition of the BNAs onto the PNA, as illustrated in FIG. 2a(IVa, IVb, IVc and IVd).

With reference to FIG. 2b, it is possible to control and specify the order and components of extensions to the PNA. If a single BBR is required, a HNA containing the complementary sequence to the 1/2 BBR in the PNA is added to the PNA to produce a single BBR and to "cap" any "booster" extensions to the PNA. If additional BBRs are to be added to the PNA, a controlled extension of the PNA can be accomplished.

With reference to FIG. 2b, a simple booster is presented. Vectorial polymer extension is accomplished by adding a BNA which is specific for the PNA, as illustrated in FIG. 2b(Ia and IIa), which when combined under hybridizing conditions with the PNA, form PNA-BNA-BNA hybrids, comprised of the PNA and "booster" extensions. These extensions, if labeled with an OSA, provide a method for greatly amplifying any signal produced upon binding of a PNA to a TNA in the sample. Furthermore, by binding labeled BBAs to the BBRs in the polymer, additional amplification is achieved.

Any of a number of methods may be used to prepare the BNAs, including, e.g., synthesis via known chemistry or via recombinant DNA production methods. In the latter method, an essentially unlimited number of BNAs may be produced simply and inexpensively, for example, by production in prokaryotes (*E. coli* for example) of a plasmid DNA having multiple repeats of the specific BNA sequences flanked by restriction sites having overhanging ends. In this fashion, for example, the bacteriophage lambda left or right operator sites, or any other DNA or other nucleic acid sequence known to specifically and tightly bind a particular BBA, such as a DNA or RNA binding protein, may be produced in an essentially unlimited number of copies, with each copy flanked by an EcoRI, PstI, BamHI or any of a number of other common restriction nuclease sites. Alternatively, a polymer at repeated sites may be excised by unique restriction sites not present within the polymer. Large quantities of pBR322, pUC plasmid or other plasmid having multiple copies of these sequences are produced by methods well known in the art, the plasmid cut with the restriction enzyme flanking the polymerized site, and the liberated multiple copies of the operators isolated either by chromatography or any other convenient means known in the art. The BNA, prior to use, is then strand separated and is then amenable for polymerization onto a PNA encoding a single stranded complementary copy of the operator as a 1/2 BBR. The BNAs may be polymerized vectorially onto the PNA by using different restriction enzymes to flank each repeat of the polymer in the plasmid used to produce multiple copies of the BNA. Alternatively, the BNA polymer may be hybridized to the PNA via overhangs at one or both ends of the BNA polymer, without the need to strand separate and anneal each BNA segment. Examples of specific BNA sequences are provided above in the section entitled Description of Sequences, as SEQ ID NOS. 35-36. To stabilize the BNA polymer, DNA ligase may be used to covalently link the hybridized BNAs.

5. The Hairpin Nucleic Acids (HNAs) and their preparation. The HNAs of the present invention comprise at least two principal parts joined together: A single-stranded sequence, which is complementary to a 1/2 BBR, and a double-stranded nucleic acid region formed, under hybridizing conditions, by the self-association of self-complementary sequences within the HNA. With reference to FIG. 1(IIc) of the drawings, the 1/2 BBR in the HNA may be constructed so as to be complementary to the 1/2 BBR sequence in the PNA. With reference to FIG. 1(I, IIc and IIIc) of the drawings, the aforementioned HNA, when added to the PNA under hybridizing conditions, forms a PNA-HNA hybrid containing a BBR. With reference to FIG. 1(IIIc, IVc and Vc) of the drawings, a PNA-HNA hybrid, under hybridizing conditions, upon addition of the TNA, can form a TNA-PNA-HNA hybrid containing a TBR and a BBR.

With reference to FIGS. 2a, 2b, 2c, and 2d, the HNAs can be used to "cap" or terminate the addition of BNA extensions to the PNA. The two BNAs in FIG. 2a(Ib and Ic) can associate to form the hybrid shown in FIG. 3a (IVb) or can hybridize directly and individually to the PNA as illustrated in FIG. 2a(Ia-c, IIa-d). The two HNAs (shown in FIG. 2c(IIIa and IIIb)) can terminate the hybridization of the BNA to other BNAs which extend from the PNA, as illustrated in FIG. 2c and 2d (IVa-d). The HNA in FIG. 2c (IIIa) can terminate the PNA-BNA hybrids shown in FIG. 2a(IIb and IId) and any PNA-BNA hybrid with a single stranded 1/2 BBR which is complementary to the 1/2 BBR in the HNA illustrated in FIG. 2c(IIIa). Similarly, the HNA in FIG. 2c(IIIb) can terminate the PNA-BNA hybrids shown in FIG. 2a(IIa and IIc) and any PNA-BNA hybrid with two single stranded 1/2 BBRs which are complementary to the 1/2 BBRs in the HNA illustrated in FIG. 2c(IIIb).

HNAs are constructed that will terminate PNA-BNA hybrids which are constructed from the sequential addition of BNAs to the PNA as illustrated in FIG. 2b). The single stranded 1/2 BBR sequences illustrated in FIGS. 2c and 2d(Ia, IIIa, Va, and VIIa) are specifically complementary to the single stranded 1/2 BBR sequences also illustrated in FIGS. 2c and 2d (Ib,IIIb,Vb and VIIb) and produce the unique capped PNA-BNA-HNA hybrids also illustrated in FIGS. 2c and 2d(Ic, IIIc,Vc and VIIc).

The self-complementary sequences in the HNA and the loop sequence which links the self-complementary hairpin sequences can be of any composition and length, as long as they do not substantially impede or inhibit the presentation of the single-stranded 1/2 BBR that comprises part of the HNA by the HNA or selectively bind the BBA or the TBA. The loop sequences should be selected so that formation of the loop does not impede formation of the hairpin. An example of an HNA useful in this application is provided as SEQ ID NO. 44 (see Description of Sequences above).

6. The Target Binding Assemblies (TBAs) and their preparation. A TBA may be any substance which binds a particular TBR formed by hybridization of particular TNAs and PNAs, provided that the TBA must have at least the following attributes:

(a) The TBA must bind the TBR(s) in a fashion that is highly specific to the TBR(s) of interest. That is, the TBA must discriminate between TBRs present in the TNA-PNA hybrid and similar duplex sequences formed by PNA-CNA hybrids. The TBA must bind the PNA-CNA hybrid with a sufficiently low avidity that upon washing the TBA-TNA-PNA complex, the PNA-CNA hybrid is displaced and the PNA-TNA hybrid is not displaced;

(b) The TBA must avidly bind the TBR(s) created by the hybridization of the TNA with the PNA. Binding affinities in the range of $10^{-5}$ to about $10^{-12}$ or higher are generally considered sufficient. As noted below, in some instances, it might be desirable to utilize a particular TBA which has a very low avidity for a particular TBR, but which has a greatly increased affinity when a particular configuration of multiple TBRs is provided so that the square of the affinity of the TBA for each TBR becomes the affinity of relevance to that particular TBA.

Examples of the DNA binding components useful in the formation of TBAs include, but are not limited to NF-kB, papillomavirus E2 protein, transcription factor SP1, inactive restriction enzymes, antibodies, etc. Each of these proteins has been recognized in the art to contain sequences which bind to particular nucleic acid sequences and the affinities of these interactions are known. Naturally, the method of the instant invention is not limited to the use of these known DNA binding proteins or fragments thereof. From the instant disclosure, it would be apparent to one of ordinary skill that the instant method could easily be applied to the use of novel TBAs exhibiting at least the required attributes noted above. Thus, for example, in WO 92/20698, a sequence specific DNA binding molecule comprising an oligonucleotide conjugate formed by the covalent attachment of a DNA binding drug to a triplex forming oligonucleotide was described. The method of that disclosure could be used to produce novel TBAs for use according to the instant disclosure, provided that the TBAs thus formed meet the criteria described above. In addition, the methods of U.S. Pat. Nos. 5,096,815, 5,198, 346, and WO88/06601, herein incorporated by reference, may be used to generate novel TBAs for use according to the method of this invention. Specific antibodies or portions thereof could be used (see for example Blais 1994).

Where the TBA is a protein, or a complex of proteins, it will be recognized that any of a number of methods routine in the art may be used to produce the TBA. The TBA may be isolated from its naturally occurring environment in nature, or if this is impractical, produced by the standard techniques of molecular biology. Thus, using NF-kB as an example, using the DNA binding portions of p50 or p65 subunits, this binding assembly could be produced according to recombinant methods known in the art (see for example Ghosh [1990] Cell 62:1019-1029, describing the cloning of the p50 DNA binding subunit of NF-kB and the homology of that protein to rel and dorsal).

Many DNA and other nucleic acid binding proteins are known which can be used as or in TBAs according to this invention. Once the amino acid sequence of any DNA, RNA: DNA, RNA or other nucleic acid binding protein is known, an appropriate DNA sequence encoding the protein can either be prepared by synthetic means, or a cDNA copy of the mRNA encoding the protein from an appropriate tissue source can be used. Furthermore, genomic copies encoding the protein may be obtained and introns spliced out according to methods known in the art. Furthermore, the TBAs may be chemically synthesized.

Once an appropriate coding sequence has been obtained, site-directed mutagenesis may be used to alter the amino acid sequence encoded to produce mutant nucleic acid binding proteins exhibiting more desirable binding characteristics than those of the original nucleic acid binding protein. As an example of this process, the amino acid sequence of the DNA binding portions of NF-kB can be altered so as to produce an NF-kB' molecule which more tightly binds the NF-kB binding site (see examples below HIV-Detect and HIV-Lock).

To provide further insight into this aspect of the invention, the following considerations are to he noted. Using NF-kB as an example, a TBA may be prepared using the naturally occurring NF-kB molecule. However, because this molecule is present in vanishingly small quantities in cells, and because the subunits of this DNA binding protein have been cloned, it would be more reasonable to prepare large quantities of the complex via recombinant DNA means as has already been accomplished for this protein (see for example Ghosh [1990] *Cell* 62:1019-1029).

NF-kB is a pleiotropic inducer of genes involved in immune, inflammatory and growth regulatory responses to primary pathogenic (viral, bacterial or stress) challenges or secondary pathogenic (inflammatory cytokine) challenges. NF-kB is a dimeric DNA binding protein comprising a p50 and a p65 subunit, both of which contact and bind to specific DNA sequences. In an inactivated state, NF-kB resides in the cellular cytoplasm, complexed with a specific inhibitor, I-kB, to form a cytoplasmic heterotrimer. Upon activation, the inhibitor is decomplexed, and the p50-p65 dimer relocates via a specific nuclear localization signal (NLS) to the cell's nucleus where it can bind DNA and effect its role as a transcriptional activator of numerous genes (see Grimm and. Baeuerle [1993] *Biochem. J.* 290:297-308, for a review of the state of the art regarding NF-kB).

The p50-p65 dimer binds with picomolar affinity to sequences matching the consensus GGGAMTNYCC (SEQ ID NO. 117), with slightly different affinities depending on the exact sequence. It is worth noting that homodimers of p50 and p65 have also been observed to occur. These homodimers display different biochemical properties as well as slightly different affinities of binding sequences within and similar to the above consensus. Thus, depending on the desired binding characteristics of the TBA, a p50-p65 heterodimer, a p50-p50 homodimer, or a p65-p65 homodimer or fragments of the aforementioned dimers may be used.

One way in which various novel TBAs may be produced for use according to this invention is shown schematically in FIG. 9. The nucleic acid recognition units of the TBA may be assembled and associated with similar or dissimilar TBA nucleic acid recognition units via a "chaperone." The chaperone is a structure on which the various TBA recognition elements are built and which confers desirable properties on the nucleic acid recognition units. The chaperone is comprised of any sequence which provides assembly sequences such that same or different nucleic acid recognition units are brought into close and stable association with each other. Thus, for example, in the case of a TBA designed to tightly bind NF-kB TBRs, a TBA is assembled by providing lambda cro sequences as assembly sequences, linked to the nucleic acid binding sequences for either NF-kB p50 or p65. The p50 or p65 nucleic acid binding sequences are linked to the cro sequences at either the carboxy or amino terminus of cro and either the carboxy or amino terminus of the nucleic acid recognition unit of the p50 or p65. Linking sequences are optionally provided to allow appropriate spacing of the nucleic acid recognition units for optimal TBR binding.

The assembly sequences, exemplified above by cro and CI sequences (SEQ ID NOS. 104-108), comprise any stable oligopeptides which naturally and strongly bond to like sequences. Thus, in the case of cry, it is well known that a dimer of cro binds to the bacteriophage lambda operator sites (Anderson et al. [1981] *Nature* 290:754-758; Harrison and Aggarwal [1990] *Ann. Rev. Biochem.* 59:933-969). The monomer units of era tightly and specifically associate with each other. Thus, by linking DNA recognition unit sequences to the cro sequences, close and tight association is achieved.

The optional linker sequences comprise any amino acid sequence which does not interfere with TBA assembly or nucleic acid binding, and which is not labile so as to liberate the nucleic acid recognition unit from the complete TBA. It is desirable but not necessary that the linker sequences be covalently linked to other binding assembly components. The association should be specific so as to aid in the assembly and manufacture of the binding assemblies. Examples of such sequences include, but are not limited to, such well known sequences as are found linking various domains in structural proteins. Thus, for example, in the lambda repressor protein, there is a linking sequence between the DNA binding domain and the dimerization domain which is useful for this purpose. Many other such sequences are known and the precise sequence thereof is not critical to this invention, provided that routine experimentation is conducted to ensure stability and non-interference with target nucleic acid binding. Examples of such sequences are provided herein as Met Ser and SEQ IN NOS. 99-102. Insertion of specific, known proteolysis sites into these linkers is also an integral part of this invention. The presence of such sites in the linker sequences would provide manufacturing advantages, allowing different molecules to be assembled on the chaperone scaffold. En addition to the nucleic acid recognition units, optional linking sequences, and assembly sequences, the novel TBAs of this invention optionally have asymmetry or PILOT TNA sequences and one or more OSA units. The asymmetry sequences are provided to encourage or prevent certain desirable or undesirable associations. For example, in the event that a TBA having homodimeric p50 DNA recognition units is desired, the asymmetry sequences are provided to disrupt the naturally stronger association of NF-kB p50 subunits and p65 subunits, while not disrupting the assembly sequences from bringing together p50 subunits. Examples of such sequences are provided herein as SEQ ID NOS. 85-92 and SEQ ID NOS. 105 and 106.

In a different configuration, NF-kB p50 subunit sequences are brought into close association with transcription factor SP1 DNA recognition unit sequences. This is desirable in the event that an NF-kB/SP1 binding motif is of significance, as in the HIV LTR where a motif of at least six DNA binding protein recognition sites, two NF-kB, three SP1, and a TATA site are known to exist. Since it is also known that the second N F-kB and first SP1 site are significant to regulation of HIV transcription (Perkins et al. [1993] *Embo J.* 12:3551-3558), this particular configuration of TBA is useful not only in the detection of HIV, but as a therapeutic or prophylactic against HIV infection (see below). In a similar fashion, the long control region (LCR) of human papillomavirus may be used as a key control region for probing according to this method.

In view of the different elements that can be associated, cassette fashion, according to this method of TBA formation, an essentially unlimited variety of TBAs are produced. In FIG. 10, a series of different molecules, referred to as "HIV-detect I-IV" are exemplified wherein "CHAP" denotes the chaperone, "nfkb" denotes NF-kB subunits, "sp1" denotes the nucleic acid recognition unit of the SP1 transcription factor, and "TATA" denotes a dimer of the DNA recognition unit of a TATA sequence DNA binding protein (TBP), also known as a TATA binding protein, or TBP. These configurations are further exemplified below and are all integral parts of the instant invention.

In yet another configuration, the modular structure shown in FIG. 9 is adapted to detection and or treatment or prophylaxis of a completely different pathogen. In FIG. 11, in a similar fashion to the above described "HIV-detect I-IV" molecules, a series of "HPV-Detect I-IV" molecules is produced. In this embodiment, advantage is taken of the DNA binding properties of the E2 protein of human papillomavirus (HPV). In addition, the roles of SP1 and TBP are taken advantage of by providing specific DNA recognition units adapted to bind to these sequences in the HPV genome. In the formation of the E2-specific TBAs for use in detecting HPV infection, it may be desirable to use any of SEQ ID NOS. 75-84 or 93-98 as the E2 DNA recognition units. A TBA containing a bovine E2 dimer and a human. E2 dimer DNA binding domain may be particularly useful, The various sequences described above may either be chemically linked using pure oligopeptide starting materials, or they may be linked through provision of recombinant nucleic acids encoding, via the well known genetic code, the various subelements. In the event of recombinant production, linking cro coding sequences to sequences of nucleic acid recognition units to form TBAs is advantageous because not only does cro act as assembly sequences in the chaperone, it also acts to direct the proper folding of the nucleic acid recognition elements. Exemplary sequences for chaperones are provided herein as SEQ ID NOS. 104-108. Furthermore, in the event that higher order structures comprising multiple binding sites is desired, as in a pentameric NF-kB/NF-kB/SP1/SP1/SP1 TBA, proper design of the asymmetry sequences allows such structures to be made.

In the foregoing fashion, TBAs are prepared which bind to their cognate binding sites with high affinity. For example, the NF-kB DNA binding components of the TBAs of FIG. 10 are expected to bind to the HIV-LTR with an affinity of between about $10^{-8}$ and $10^{-12}$ molar. Sequences useful as the DNA recognition units are provided as SEQ ID NOS. 63-71, 73-84, 93-98, and 104-108 and exemplified further below.

In view of the foregoing description of directed assembly of nucleic acid binding proteins using assembly and asymmetry (or piloting) sequences, those skilled in the art will recognize that a generally applicable method for assembling protein structures is provided by this invention. The generality of this method is demonstrated further by consideration, by way of further example, of the use of an antibody-epitope interaction in the assembly of desired structures. By way of specificity, a DNA binding protein structure may be assembled by linking an NF-kB p50 subunit to an antigen, such as a circularized (through disulfide bonds) melanocyte stimulating hormone (MSH). This pro-MSH molecule may then be bound by an anti-MSH antibody to provide a novel nucleic acid binding assembly, with the antigen and antibody acting as assembly sequences.

The modular structure provided by FIG. 9 reveals that a great variety of TBAs may be assembled using different combinations of components. Thus, representative embodiments of this general structure are provided as SEQ ID NOS. 109-116.

7. The Booster Binding Assemblies (BBAs) and their preparation. (See FIGS. 4*a*-4*c*) A BBA may be any substance which binds a particular BBR formed by hybridization of particular PNAs and BNAs, including when multiple BNAs (up to and including "n" BNAs, i.e., $BNA_n$, wherein "n" is theoretically 0-∞, but practically is between about 0 and 100) are polymerized onto the PNA for signal amplification, provided that the BBA must have at least the following attributes:

(a) The BBA must bind the BBRs in a fashion that is highly specific to the BBR of interest. That is, the BBA must discriminate between BBRs present in the PNA-BNA hybrid and similar duplex sequences in BNA-CNA hybrids or other CNAs. Thus, where even a single base mismatch or conformational differences with or without base mismatches occur in the production of the PNA-$BNA_n$ or PNA-$BNA_n$-HNA hybrid, the BBA must bind the hybrid with a sufficiently low avidity that upon washing the TBA-TNA-PNA-$BNA_n$ complex, the BBA is displaced from the CNA sequences but not the BBR sequences.

(b) The BBA must avidly bind the BBR(s). Binding affinities in the range of $10^{-5}$ to about $10^{-9}$ or higher are generally considered sufficient.

Examples of BBAs include, but are not limited to cro, and the bacteriophage lambda repressor protein, CI. In addition, see U.S. Pat. No. 4,556,643, herein incorporated by reference, which suggests other DNA sequences and specific binding proteins such as repressors, histones, DNA modifying enzymes, and catabolite gene activator protein. See also EP 0 453 301, herein incorporated by reference, which suggests a multitude of nucleotide sequence specific binding proteins (NSSBPs) such as the tetracycline repressor, the lac repressor, and the tryptophan repressor. Each of these BBAs has been recognized in the art to bind to particular, known nucleic acid sequences and the affinities of these interactions arc known. Naturally, the method of the instant invention is not limited to the use of these known BBAs. From the instant disclosure, one of ordinary skill could easily apply the use of novel BBAs exhibiting at least the required attributes noted above to the instant method.

Examples of novel BBAs useful according to this aspect of the invention include novel proteins based on the motif of a known DNA or RNA or DNA:RNA binding protein such as cro or the λ CI repressor protein. Preferably, such modifications are made to improve the handling of these components of the invention. Thus, it may be desirable to add a high concentration of cro to an assay. One of the negative qualities of cro is that at high concentrations, the binding of cro to its DNA target comes into competition with cro-cro interactions. Thus, for example, a chaperoned or mutated cro may be produced which does not have this shortcoming. Examples of such altered chaperones are SEQ ID NOS. 105-106 and 108. Methods known in the art, such as production of novel target binding proteins using variegated populations of nucleic acids and selection of bacteriophage binding to particular, pre-selected targets (i.e., so-called phage-display technology, see discussion above for production of novel TBAs) may be used to produce such novel BBAs as well as the aforementioned novel TBAs.

Where the BBA is a protein, or a complex of proteins, it will be recognized that any of a number of methods routine in the art may be used to produce the BBA. The BBA may be isolated from its naturally occurring environment in nature, or if this is impractical, produced by the standard techniques of molecular biology. Thus, for example, the sequence of the cm protein is known and any molecular clone of bacteriophage lambda may be used to obtain appropriate nucleic acids encoding cro for recombinant production thereof. In addition, the TBAs described herein may be used as BBAs, provided that different TBAs are used to bind TBRs and BBRs.

8. The use of BBAs and BBRs to localize and amplify the localization of the PNA-TNA-TBA complexes (see FIGS. 8*a* and 8*b*). In one embodiment of this invention, the highly specific and extremely tight binding of TBAs comprised of nucleic acid binding components is used to produce an amplifiable nucleic acid sandwich assay. According to one aspect of this embodiment, a solid support is coated with a first TBA creating an immobilized TBA. In solution, a PNA and TNA are contacted under hybridizing conditions and then contacted with the immobilized TBA. Only those PNA-TNA interactions which form the specific TBR recognized by the immobilized TBA are retained upon wash-out of the solid surface which binds the TBA-TBR complex.

Detection of the bound TBR is accomplished through binding of Booster Nucleic Acids, BNAs, to the 1/2 BBRs present on the PNAs under hybridizing conditions. In this manner, even if only a single TBA-TBR complex is bound to the immobilized TBA, a large, amplified signal may be produced by polymerizing multiple BNAs to the immobilized TNA. Each BNA which binds to the TNA forms a BBR which can be bound by BBAs which, like the TBAs immobilized on the solid surface, may be chosen for their very tight and specific binding to particular nucleic acid structures. Thus, according to this embodiment, the immobilized TBA may contain the DNA binding portion of NF-kB, which very specifically and tightly binds to NF-kB binding sites formed upon hybridization of the TNA and PNA to form such a site.

Because it is well known that there are NF-kB binding sites both in the normal human genome and in the long terminal repeats of human immunodeficiency virus (HIV), this invention provides a method of discriminating between the "normal" human sites and the sites present in cells due to HIV infection. Therefore, in a test designed to determine the presence or absence of HIV DNA in a sample of human DNA, the HIV NF-kB binding sites may be viewed as the TNA, and the normal human NF-kB binding sites may be viewed as CNAs. According to the method of this invention, discrimination between these TNAs and CNAs is accomplished by taking advantage of the fact that in the HIV LTR, there are two NF-kB binding sites, followed by three SP1 sites (see, for example, Koken et al. [1992] *Virology* 191:968-972), while cellular NF-kB binding sites with the same sequences are not found in tandem.

In cases where the TNA contains more than one 1/2 TBR and it is desirable to pursue the therapeutic and prophylactic applications of the TBAs, it may be desirable to use more than one TBA, each with the capacity to bind a TBR in the TNA-PNA complex. In this case, it may be advantageous to select, as components of the TBAs, DNA-binding or RNA-binding domains with lesser affinity for its TBR than the wild-type DNA-binding or RNA-binding domain. Given that the TBAs which are involved in the binding to the multiple TBRs can either assemble together before binding to their TBRs or assemble together after binding to their TBRs, the individual TBAs will not block the corresponding TBRs in the other genomes than the target genome unless the TBRs are spatially capable of binding the assembled TBA complex. One feature of the multimeric assembly of TBAs which is specifically claimed here as part of this invention is that such a multimeric assembly is expected to have a much reduced affinity for a single site within the TNA. However, since the binding is dramatically increased relative to any one TBA, the TBA complex would be expected to not compete for the binding of any single TBR with the corresponding native proteins in situ but bind tightly to sequences in the PNA-TNA hybrid containing the TBRs for each of the nucleic acid-binding components assembled in the TBA. The TBA complex should be assembled and linkers adjusted in the individual TBAs so as to allow the nucleic acid-binding regions contained in the TBA complex to simultaneously reach and bind to these targets.

Once the TNA-PNA hybrids have formed and been contacted with the immobilized TBA, unbound nucleic acid is washed from the immobilized surface and the immobilized hybrids detected. This is accomplished in any one of several ways. In one aspect of this invention, the PNA is labeled with an OSA, such as a radionuclide, colored beads, or an enzyme capable of forming a colored reaction product. Furthermore, in addition to having one or more 1/2 TBRs, the PNA also may contain at least one 1/2 BBR. The 1/2 BBR sequences are chosen so as to be complementary to unique 1/2 BBR sequences in BNAs. In the embodiment described above, for example, where the TBA is NF-kB and the TBR formed upon TNA-PNA hybridization is one or more NF-kB binding sites, the 1/2 BBRs may provide hybridizable (that is, single-stranded, complementary) sequences of the left or right bacteriophage lambda operators (see, for example, Ptashne [1982] *Scientific American* 247:128-140, and references cited therein for sequences of these operators). These may be polymerized onto the PNA 1/2 BBRs in a vectorial fashion (see FIGS. 2 and 3) providing up to "n" BBRs, and each BBR forms a cro binding site. Enzymatically, radioactively, or otherwise labeled cro, is contacted with the TBA-TNA-PNA-(BNA)$_n$ complex. In this fashion, a highly selective and amplified signal is produced. Signal produced using a PNA having a single 1/2 TBR indicates success of the assay in achieving TBA-TBR binding and polymerization of the BNAs to produce signal from cellular sites (i.e. from CNAs). Absence of signal when a dimerized TBA is used indicates that in the TNA, there were no HIV LTRs as no double NF-kB binding sites were present. On the other hand, presence of signal using the dimer NF-kB indicates HIV infection. As a specific example of the foregoing description of this embodiment of the invention, see Example 6 describing an HIV test kit.

Naturally, those skilled in the art will recognize that the foregoing description is subject to several modifications in the choice of PNAs, TNAs, TBAs, BNAs, and BBAs. Furthermore, in systems other than HIV, those skilled in the art will recognize that the general method described above could be likewise applied. However, these other applications may be simpler than the above described method as the TBAs used may not recognize any normal cellular sites and therefore resort to dimerization or other methods of discriminating between TNAs and CNAs may be less critical. In designing probes and binding assemblies for these other systems, the skilled artisan will be guided by the following principles and considerations.

In the above-described embodiment, the appeal of using the DNA-binding portions of NF-kB protein as the TBA and the NF-kB recognition binding elements as the TBRs is that these elements form an important "control point" for the replication of HIV. That is, it is known that HIV is required to use NF-kB as a critical feature in its replicative life cycle. Similar control points for other pathogens are chosen and used as a basis for detection according to the methods described herein.

From the foregoing description of general features of this invention and the mode of its operation, one skilled in the art will recognize that there are a multiplicity of specific modes for practicing this invention. By way of example, the method of this invention is adaptable to a method and devices using chromatographic test kits described in U.S. Pat. Nos. 4,690,691 and 5,310,650 (the '691 and '650 patents). In those patents, a porous medium was used to immobilize either a TNA or a capture probe, and a solvent was used to transport a mobile phase containing either a labeled PNA, if the TNA was immobilized, or the TNA, if a capture probe was immobilized, into the "capture zone." Once the TNA was bound in the capture zone, either by directly immobilizing it or through capture, a labeled PNA was chromatographed through the capture zone and any bound label was detected.

Adapting the instant invention to such a system provides the improvement of using a Target Binding Assembly in the capture zone and therefore, the capture of only perfectly matched TBR sequences or other TBRs representing nucleic acid confirmations specifically bound by the TBA within the TNA-PNA duplexes by virtue of the previously described sensitive discrimination by the TBA between TNAs and CNAs.

Once the TNA-PNA hybrids become bound to the immobilized TBA, the signal is amplified by adding BNAs or chromatographing BNAs through the capture zone. Finally, the signal may be further amplified by adding BBAs or chromatographing labeled BBAs through the capture zone. In this fashion, the ease of performing the analysis steps described in the '691 and '650 patents is improved upon herein by providing the additional ability to increase the specificity and, through amplification, the sensitivity of the method described in those patents. The disclosure of the '691 and '650 patents is herein incorporated by reference for the purpose of showing the details of that method and for the teachings provided therein of specific operating conditions to which the compositions and methods of the instant invention are adaptable.

Those skilled in the art will also recognize that the method of the instant invention is amenable to being run in microtiter plates or to automation. The use of machines incorporating the method of this invention therefore naturally falls within the scope of the instant disclosure and the claims appended hereto. Thus, for example, this invention is adaptable for use in such instruments as Abbott Laboratories' (Abbott Park, Ill.) IMx tabletop analyzer. The IMx is currently designed to run both fluorescent polarization immunoassay (FPZA, see Kier [1983] *KCLA* 3:13-15) and microparticle enzyme immunoassay (MEZA, see *Laboratory Medicine*, Vol. 20, No. 1, January 1989, pp. 47-49). The MEZA method is easily transformed into a nucleic acid detection method using the instant invention by using a TBA as a capture molecule coated onto a submicron (<0.5 μm on average) sized microparticle suspended in solution. The microparticles coated with TBA are pipetted into a reaction cell. The IMx then pipettes sample (hybridized PNA-TNA) into the reaction cell, forming a complex with the TBA. After an appropriate incubation period, the solution is transferred to an inert glass fiber matrix for which the particles have a strong affinity and to which the microparticles adhere. Either prior to or after filtering the reaction mixture through the glass fiber matrix, BNAs and BBAs are added, or another signal amplification and detection means is used which depends on specific formation of TNA-PNA hybrids. The immobilized complex is washed and the unbound material flows through the glass fiber matrix.

The bound complexes are detected by means of alkaline phosphatase labeled BBAs or otherwise (radioactively, enzymatically, fluorescently) labeled BBAs. In the case of alkaline phosphatase labeled BBAs, the fluorescent substrate 4-methyl umbelliferyl phosphate or like reagent may be added. Alternatively, the enzyme may be bypassed by directly labeling BBAs with this or a like reagent. In any event, fluorescence or other signal is proportional to the amount of PNA-TNA hybrids present.

The fluorescence is detected on the surface of the matrix by means of a front surface fluorometer as described by the manufacturer of the IMx. With minor adjustments that can be made through routine experimentation to optimize an instrument such as the IMx for nucleic acid hybridization and nucleic acid-TBA interactions, the instant invention is completely adaptable to automated analyses of TNA samples.

9. Other diagnostic applications of this invention. While the foregoing description enables the use of the instant invention in a number of different modes, many additional utilities of this invention are readily appreciated, for example, in a mobility retardation system.

In this embodiment of the invention, an improvement of the well known electrophoretic mobility shift assay (EMSA) is conducted as follows (See FIGS. 12a and 12b):

A sample of DNA is fragmented, either through random cleavage or through specific restriction endonuclease treatment. The DNA in the sample is then split into two equal aliquots and a specific TNA is added to the first aliquot but not to the second. The first and second aliquot are then electrophoresed in an acrylamide or agarose gel, and the pattern of DNA bands (either visualized through ethidium bromide binding or through being radioactively labeled prior to electrophoresis is then compared for the two aliquots. Fragments of DNA having binding sites to which the TBA is specific are retarded in their migration through the electrophoretic medium. By using an appropriate TBA, any number of DNA or other nucleic acid sequences may be tracked in this fashion.

In a modification of the EMSA described above, fragmented TNA is hybridized with a PNA and fractionated in a first dimension. The fractionated DNA is then reacted with an appropriate TBA and the change in mobility of the DNA fragments is noted. Enhancement of the retardation is possible by adding BBAs as described above. (See, for example, Vijg and references cited therein for known techniques of two (2) dimensional nulceic acid electrophoresis, to which the instant method may be applied).

10. Therapeutic applications. Because of the very tight and selective nucleic acid binding characteristics of the novel TBAs described herein, therapeutic utilities are contemplated in addition to the diagnostic utilities of these compounds. Thus, a TBA comprising tight and specific binding for the HIV-LTR, by virtue of having an NF-kB p50 and an SP1 DNA recognition unit in close association (see FIG. 10, HIV-Detect II) is useful to bind up the HIV-LTR and thereby prevent transcription from this key element of the HIV genome. The unique features of the assembly sequences of the TBA allow recombinant vectors to introduce DNA encoding such a TBA into a cell and the proper folding of the expressed sequences. Once inside the cell, the nuclear localization signals of the p50 subunit directs the transport of the TBA to the nucleus where it binds tightly to the LTR of any integrated HIV, effectively shutting the pathogen down. In a prophylactic mode, one that is concerned about potential HIV exposure is administered a sufficient dose of a TBA or a recombinant vector able to express the TBA, so as to lock up any HIV that might have entered the person. In this mode, the use of the TBA is analogous to passive protection with a specific immune globulin. In the therapeutic or prophylactic mode, NLS sequences are used in place of the OSAs used in the diagnostic mode. Exemplary NLS sequences are provided as SEQ ID NOS. 72 and 103 (see also Heinzinger 1994 and Bukinsky 1993, describing NLS sequences of the HIV Vpr and gag proteins respectively). In any event, the TBA is administered in a pharmaceutically-acceptable carrier, known in the art such as a sterile salt solution or associated with a liposome or in the form of a recombinant vector, preferably one which directs expression of the TBA in a chosen cell type, or by a protein delivery system.

II. Embodiments of the Invention

In view of the foregoing description and the examples which follow, those skilled in the art will appreciate that this disclosure describes and enables various embodiments of this invention, including:

1. A probe nucleic acid (PNA) comprising:
   (a) a single-stranded sequence, 1/2 TBR, which is capable of forming, under hybridizing conditions, a hybrid, TBR, with a 1/2 TBR present in a target nucleic acid (TNA);
   (b) zero, one or more, and preferably one to ten single stranded sequences, 1/2 BBR, which is capable of forming, under hybridizing conditions, a hybrid BBR, with a 1/2 BBR present in a booster nucleic acid (BNA); and
(c) an OSA, which is no attached support and/or indicator, or an attached support or other means of localization, including, but not limited to, attachment to beads, polymers, and surfaces, and/or indicators;

wherein said TBR is capable of binding with high affinity to a TBA, said TBA being a substance capable of discriminating between a paired TBR and a TBR having unpaired nucleotides, and further, wherein said BBR is capable of binding with high affinity to a BBA, said BBA being a substance capable of discriminating between a paired BBR and a BBR having unpaired nucleotides. This embodiment includes TBRs which are nucleic acid binding protein recognition sites, such as the HIV LTR, and other nucleic acid binding protein recognition sites in other pathogens, some of which are noted above. The PNA of this embodiment of the invention may produce a TBR which is a nucleic acid binding protein recognition site present in the genome of a pathogen or is a binding site associated with a pathogenic condition in the human genome or a contaminant in a fermentation process.

2. A booster nucleic acid (BNA) comprising:
(a) a 1/2 BBR which has a sequence which is complementary to a 1/2 BBR sequence in a PNA or another BNA already hybridized to the PNA and which is capable of forming, under hybridizing conditions, a hybrid, BBR, with the PNA;
(b) an OSA attached support or other means of localization, including, but not limited to, attachment to beads, polymers, and surfaces, and/or indicators; and
(c) additional hybridization sites, 1/2 BBRs, for hybridization with additional BNAs;

wherein said BBR is capable of binding with high affinity to a BBA, said BBA being a substance capable of discriminating between a paired BBR and a BBR having unpaired nucleotides.

3. A Hairpin Nucleic Acid (HNA) comprising a single-stranded sequence, 1/2 BBR, which under hybridizing conditions is capable of forming a hairpin while at the same time binding to a BNA to form a BBR capable of binding a BBA, wherein said BBR is capable of binding with high affinity to a BBA, said BBA being a substance capable of discriminating between a paired BBR and a BBR having unpaired nucleotides.

4. A method for detecting a specific TNA sequence, comprising the steps of:
(a) hybridizing said TNA with a PNA as described above;
(b) hybridizing said PNA with a BNA containing a 1/2 BBR whose sequence is complementary to a 1/2 BBR sequence in the PNA;
(c) adding the products of steps (a) and (b) containing a TBR and a BBR, to a surface, liquid or other medium containing a TBA;
(d) adding BBAs to the mixture in step (c) wherein said BBA comprises:
(i) a molecule or a portion of a molecule which is capable of selectively binding to a BBR; and
(ii) a detectible indicator; and
(e) detecting signal produced by the indicator attached to the BBA. This method includes the use of a protein indicator, including enzymes capable of catalyzing reactions leading to production of colored reaction products. It also includes indicators such as a radionuclide or colored beads.

5. A method for detecting the presence in a sample of a specific Target Nucleic Acid, TNA, which comprises:
(a) contacting said sample with a Probe Nucleic Acid, PNA, which, upon hybridization with said TNA if present in said sample, forms a Target Binding Region, TBR, which is capable of binding a Target Binding Assembly, TBA;
(b) contacting said sample, already in contact with said PNA, with a TBA capable of binding to any TBRs formed by the hybridization of said PNA and said TNA in the sample.

6. A method for detecting or localizing specific nucleic acid sequences with a high degree of sensitivity and specificity which comprises:
(a) adding PNAs containing a 1/2 BBR and a 1/2 TBR to a sample containing or suspected of containing TNAs containing 1/2 TBR sequences, to form a complex having target binding regions, TBRs, formed by the hybridization of complementary 1/2 TBRs present in the PNAs and TNAs respectively;
(b) binding the TBRs formed in step (a) to an immobilized TBA to form a TBA-TNA-PNA complex;
(c) adding Booster Nucleic Acids, BNAs, containing booster binding regions, 1/2 BBRs, to the complex formed in step (b) such that the 1/2 BBRs in the BNAs hybridize with the 1/2 BBR sequences present in the PNAs or to 1/2 BBRs present in BNAs already bound to the PNA, to form BBRs, such that TBA-TNA-PNA-(BNA)$_n$ complexes are formed;
(d) adding Hairpin Nucleic Acids, HNAs, containing 1/2 BBR sequences, to the complex formed in step (c) such that the 1/2 BBRs in the HNAs hybridize with any available 1/2 BBR sequences present in the BNAs of the complex of step (c), thereby capping the extension of the BNAs onto the TBA-TNA-PNA-(BNA)$_n$ complexes of step (c) to form TBA-TNA-PNA-(BNA)$_n$-HNA complexes;
(e) adding Booster Binding Assemblies, BBAs, linked to indicator moieties, to the TBA-TNA-PNA-(BNA)$_n$-HNA complexes formed in step (d) to form TBA-TNA-PNA-(BNA-BBA)$_n$-HNA complexes; and
(f) detecting the signals produced by the indicator moieties linked to the TBAs, PNAs, BNAs, BBAs or HNAs in the TBA-TNA-PNA-(BNA-BBA)$_n$-HNA complexes of step (e);

wherein:
the TNA comprises:
(i) one or more specific 1/2 TBR nucleic acid sequences, the presence or absence of which in a particular sample is to be confirmed;
the PNA comprises:
(i) a single-stranded sequence, 1/2 TBR, which is capable of forming, under hybridizing conditions, a hybrid, TBR, with a 1/2 TBR present in a target nucleic acid (TNA);
(ii) a single stranded sequence, 1/2 BBR, which is capable of forming, under hybridizing conditions, a hybrid BBR with a 1/2 BBR present in a booster nucleic acid (BNA); and
(iii) an OSA, which is no attached support and/or indicator, or an attached support or other means of localization, including, but not limited to, attachment to beads, polymers, and surfaces, and/or indicators;
the BNA comprises:
(i) a 1/2 BBR, as shown in FIG. 1(IIb), which has a sequence which is complementary to a 1/2 BBR sequence in a PNA and which is capable of forming, under hybridizing conditions, a hybrid, BBR, with the PNA;

(ii) an OSA attached support or other means of localization, including, but not limited to, attachment to beads, polymers, and surfaces, and/or indicators;

(iii) additional hybridization sites, 1/2 BBRs, for other BNAs; and (iv) sequences, 1/2 BBRs, which can hybridize to BNAs already hybridized to the PNA;

the BBA comprises:

(i) a molecule or a portion of a molecule which is capable of selectively binding to a BBR; and (ii) no attached support and/or indicator, or an attached support or other means of localization, including, but not limited to, attachment to beads, polymers, and surfaces, and/or indicators;

and the TBA comprises:

(i) a molecule or a portion of a molecule which is capable of selectively binding to a TBR; and (ii) no attached support and/or indicator, or an attached support or other means of localization, including, but not limited to, attachment to beads, polymers, and surfaces, and/or indicators.

7. An improvement to a solid phase hybridization method for detecting the presence of a target polynucleotide involving: immobilizing a target polynucleotide, if present in a test sample, directly or via an intermediate capture structure, on a solid phase at a capture site; before, during or after said immobilization, attaching a detectable label to said target polynucleotide, if present; and detecting said label, if any, at said capture site; the improvement comprising:

(a) using a Target Binding Assembly, TBA, as the means for achieving immobilization of said target polynucleotide, wherein said TBA binds only to a perfect hybrid formed between a specific Probe Nucleic Acid, PNA, and said target nucleic acid such that a perfect Target Binding Region, TBR, recognizable by said TBA is formed; and (b) including in the PNA a single stranded sequence, 1/2 BBR, capable of binding a Booster Nucleic Acid, BNA, containing a single stranded complementary 1/2 BBR which, upon hybridization with the 1/2 BBR in the PNA, forms a BBR capable of binding labeled Booster Binding Assemblies, BBAs.

8. A target binding assembly, TBA, comprising one or more nucleic acid recognition units, linker sequence(s), assembly sequence(s), asymmetry sequence(s), nuclear localization signal sequence(s) (NLS) and OSA(s). The nucleic acid recognition unit may be an NF-kB binding unit, an SP1 binding unit, a TATA binding unit, a human papillomavirus binding unit, an HIV LTR binding unit, or a binding unit for any other fragment of specific sequence the detection of which is desirable and which can be achieved through specific association with the TBA. Such recognition units include, but are not limited to those exemplified herein as SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, and SEQ ID NO. 73. Linker sequences such as oligopeptides which do not interfere with the nucleic acid recognition function of the nucleic acid recognition unit and which provide stability and control over the spacing of the nucleic acid recognition unit from the remainder of the TBA. Examples of such linker sequences are well known in the art and include, but are not limited to oligopeptide sequences from the interdomain primary sequence of a structural protein. Assembly sequences include oligopeptide sequences which direct the folding and association of nucleic acid recognition units. A preferred example of such sequences are oligopeptides derived from the bacteriophage lambda cro protein. The asymmetry sequence directs the association of nucleic acid recognition and assembly sequences in a predetermined order. Such asymmetry sequences are exemplified by sequences derived from insulin, relaxin, gonadotropic hormone, FSH, HCG, LH, ACTH, including but not limited to SEQ ID NOS. 85-92. With reference to FIGS. 14 and 15, SEQ ID NO. 85 is an "A" and SEQ ID NO. 86 is a "B" sequence; SEQ ID NO. 87 is an "A" and SEQ ID NO. 88 is a "B" sequence' SEQ ID NO. 89 is a human relaxin "A" and SEQ ID NO. 90 is a human relaxin "B" sequence; SEQ ID NO. 91 is a skate relaxin "A" and SEQ ID NO. 92 is a skate relaxin "B" sequence. In addition, the TBA may contain nuclear localization signal sequences, NLS, which direct the migration and uptake of a protein or complex associated with said NLS into the nucleus of a cell. Examples of such NLS sequences are provided as SEQ ID NOS. 72 and 103. Preferred embodiments of the TBA include but are not limited to HIV Detect I-IV or HPV Detect I-IV, and SEQ ID NOS. 109-116.

9. Methods of using the novel TBAs of this invention include, but are not limited to a method of using the TBA to bind a particular nucleic acid sequence in a target nucleic acid sample which comprises:

(a) fragmenting the nucleic acid in the target nucleic acid sample;

(b) contacting, under hybridizing conditions, the fragmented nucleic acid with a probe nucleic acid complementary to the particular nucleic acid sequence of interest, wherein said probe nucleic acid, upon hybridization with said particular nucleic acid sequence of interest forms a target binding region to which said TBA specifically binds.

In this method, the probe nucleic acid, in addition to sequences complementary to said particular nucleic acid sequence of interest, also may have additional sequences to which a booster nucleic acid can bind to form a booster binding site to which a labeled booster binding assembly can hind to provide a signal showing and amplifying the binding of the probe nucleic acid to the target nucleic acid sequence of interest.

An additional aspect of this invention not requiring fragmentation of Target Nucleic Acid, involves administration of the TBA to a patient in need of such treatment of a therapeutically or prophylactically effective amount of said TBA, which comprises administering the TBA, either in the form of a purified protein complex or in the form of a recombinant vector which, upon entry into the patient is able to express the TBA, such that the TBA binds the particular nucleic acid sequence to achieve the desired prophylactic or therapeutic result. This may include providing a dosage which can be determined by routine experimentation to be sufficient to prevent establishment of an active infection by a pathogen. Dosages of purified TBAs may be in the range of about 0.001 to 100 mg/kg. When provided as a recombinant expression vector which will direct the in vivo expression and folding of the TBA, dosages of the recombinant nucleic acid may be substantially lower, particularly if provided in the form of non-pathogenic viral vector. The methods of using the TBAs also include monitoring the shift in mobility of nucleic acids in target nucleic acid samples as a function of the size such that binding of the TBA to a particular fragment in the sample modifies the mobility of the fragment. This aspect of the method provides a useful method of analyzing nucleic acid fragments for particular aberrations, such as might be found associated with metastases.

10. Diagnostic or forensic kits useful in determining the presence of an infection, the susceptibility to a disease, or the origin of a particular nucleic acid containing sample.

11. A method of assembling multimeric TBAs in vivo which comprises introducing nucleic acids encoding component TBAs into a cell. The component TBAs should each contain a nucleic acid recognition unit, assembly sequences, asymmetry sequences, and nuclear localization signal sequences. Linker sequences, optionally included if TBA footprinting experiments indicate the need for such linkers to attain optimal geometry of the multimeric TBA. Upon in vivo expression of each component TBA and proximal binding, via the nucleic acid recognition unit of each component TBA to nucleic acid sequences encountered in the nucleus or elsewhere in the cell, component expressed TBAs are directed to assemble via the included assembly and asymmetry sequences into multimeric TBAs. As described above, such multimeric TBAs will have the advantage of binding specifically with high affinity to TBRs in a specific target sequence, but not at all or with very low affinity to cousin nucleic acids.

The foregoing description of the invention will be appreciated by those skilled in the art to enable preferred embodiments as well as the best mode of this invention. Without limiting the subject matter to the specifics of the examples provided hereinafter, the following examples are provided to further guide those skilled in the art on methods of practicing this invention. Standard recombinant DNA techniques as disclosed in Sambrook, Fritsch, and Maniatis (1989) *Molecular Cloning: A Laboratory Manual*, 2nd Ed., Cold Spring Harbor Laboratory Press, Cold Spring Harbor, N.Y., and more recent texts are not disclosed as these are now well within the skill of the ordinary artisan.

EXAMPLE 1

Preparation of PNAs and Labeling of PNAs

Probe nucleic acids, PNAs, may be prepared by means well known in the art. Thus, single stranded polynucleotide PNAs of defined sequence may be prepared via solid phase chemical synthesis according to Merrifield. PNAs may be prepared by automated synthesis using commercially available technology, such as resins and machines produced or marketed by Applied Biosystems, ABI, or other manufacturers. Alternatively, through known recombinant DNA methods, particular PNA sequences are synthesized in vivo, for example by cloning a duplex PNA into a vector which can replicate in *E. coli*, large quantities of the duplex PNA may be prepared. Multimers of the PNA may be cloned into the vector such that for each mole of vector, several moles of PNA is liberated upon digestion of the vector with a restriction fragment flanking the PNA sequence. Subsequent to synthesis or recombinant production, the PNAs are purified by methods well known in the art such as by gel electrophoresis or high pressure liquid chromatography (HPLC). If the PNA is produced as a duplex, prior to use in a hybridization assay for detection of target nucleic acid sequences, the strands of the PNA are separated by heating or other methods known in the art.

The specific sequence of bases in the PNA is chosen to reflect the sequence to be detected in a TNA, with the proviso that, according to this invention, the PNA contains a 1/2 TBR sequence, which is one that upon hybridization of the PNA and TNA, a TBR is formed. As there are an essentially unlimited number of such sequences known in the art, the choice of the PNA sequence is amenable to selection by the skilled researcher for any given application. The sequence of the HIV LTR is one such sequence, which upon hybridization of a PNA encoding portions of the LTR with TNAs encoding the HIV LTR, TBRs capable of binding the NF-kB or SP1 DNA binding proteins are formed.

In addition to sequences which will form a TBR upon hybridization, the PNA also may contain a 1/2 BBR. This sequence is one which, upon hybridization with a booster nucleic acid, BNA, forms a BBR which is capable of binding a BBA. The BBA is preferably a DNA binding protein having high affinity for the BBR sequence.

In this particular example, hybridization between a PNA having as a 1/2 TBR, SEQ ID NO. 4 and, at the 3' end of that sequence, a 1/2 BBR sequence shown as SEQ ID NO. 35. The PNA encoding these sequences is either used without labeling or is labeled with a radioactive isotope such as $P^{32}$, $S^{35}$, or a similar isotope, according to methods known in the art. Alternatively, the PNA is bound to a bead of between 0.01 to 10 µm, which may be colored for easy visual detection. This label forms the OSA as described in the specification. This probe hybridizes with HIV LTR sequences to form a TBR that binds NF-kB. In addition, the PNA hybridizes with BNAs having a complementary 1/2 BBR to form a bacteriophage lambda left operator that binds either cro or lambda repressor proteins.

In a manner similar to that described above, PNAs are used wherein the 1/2 TBR is any one of SEQ ID NO. 5 or SEQ ID NOS. 7-34, and a 1/2 BBR, such as SEQ ID NO. 35 or SEQ ID NO. 36 is either at the 3' end or 5' end of the 1/2 TBR.

EXAMPLE 2

Preparation and Labeling of BNAs

Similar to the methods described in Example 1 for preparation and labeling of PNAs, BNAs are prepared and labeled according to methods known in the art. As described in U.S. Pat. No. 4,556,643, herein incorporated by reference (see particularly Example 1), nucleic acid sequences encoding particular nucleic acid binding sequences may be mass produced by cloning into a replicable vector. Furthermore, similar to that disclosure, the 1/2 TBR and 1/2 BBR sequences may be co-linearly produced in this fashion, with the distinction, however, that according to the instant invention, the 1/2 TBR sequence itself forms a nucleic acid binding component recognition site and the 1/2 BBR, while forming a nucleic acid binding component recognition site, also provides a means of amplifying the signal produced upon binding of the 1/2 TBR to complementary sequences in the TNA by providing for polymerization of BNAs onto the TNA bound PNA. To enable this, a sequence such as SEQ ID NO. 35, which encodes the left operator of bacteriophage lambda, is provided with additional sequences such that an overhang sequence is created on one or both ends of the BNA upon hybridization with the PNA.

As a specific example, vectorial polymerization of BNAs onto a TNA is provided by SEQ ID NOS. 40-43. In this example, SEQ ID NO. 40 encodes two 1/2 TBRs which will hybridize with two 1/2 TBRs in a TNA to form two NF-kB binding sites, while at the same time providing a bacteriophage lambda left operator 1/2 BBR, which additionally is terminated at the 3' end with the recognition site for the restriction enzyme PstI. Addition of the BNA, SEQ ID NO. 41, with the 1/2 BBR complementary to the 1/2 BBR on the PNA, SEQ ID NO. 40, completes the BBR while at the same time completing the PstI recognition site, leaving a four base overhang for hybridization with additional BNAs. Accordingly, SEQ ID NO. 42 is added which has a four base pair sequence at the 3' end which is complementary to the four-base overhang remaining from the hybridization of SEQ ID NOS. 40 and 41. In addition, SEQ ID NO. 42 is provided with a five base sequence at its 5' end which forms part of a BamHI recognition site. The growing polymer of BNAs is extended further by addition of the BNA SEQ ID NO. 43, which is complementary to SEQ ID NO. 42, completing the BBR while at the same time completing the BamHI recognition site and leaving a four base overhang which may be further hybridized with BNAs having complementary sequences. In this fashion, the BNAs may he hybridized extensively so as to greatly amplify the signal of a single PNA-TNA hybridization event.

As with the PNAs described in Example 1, the BNAs may be used in an unlabeled form or may be labeled according to methods known in the art and described in Example 1. It will also be appreciated that, rather than produce the BNA polymer by sequential addition of BNAs to the PNA-TNA complex, the BNA polymer may be preformed and added directly to the PNA-TNA complex. One simple method for preforming such a BNA polymer includes the recombinant production of a vector in which multimers of the BNA are provided with a unique restriction site at either end of the polymer. This polymer of BNAs containing multiple BBRs is cut out of the vector and hybridizes to a single stranded 1/2 BBR remaining in the PNA upon hybridization of the PNA and the TNA. This is accomplished by providing a single stranded sequence in the PNA complementary to an overhang produced in the BNA polymer when it is excised from the production vector.

EXAMPLE 3

Production of HNAs and Their Use for Capping BNA Polymers

The HNAs of this invention are produced according to methods known in the art for polynucleotide production as described in Examples 1 and 2 for PNAs and BNAs. In the production of the HNAs, however, the sequence of the HNA is specifically designed so that a substantial portion of the HNA forms a self-complementary palindrome to form a hairpin, while at the same time, leaving, in single stranded form enough bases to be able to hybridize with single stranded sequences in the growing chain of BNAs described in Example 2.

In this Example, a HNA of SEQ ID NO. 44 is provided to cap the extension of BNAs onto the PNA in Example 2 after the addition of the BNA, SEQ ID NO. 43. This is accomplished because SEQ ID NO. 44, while having a palindromic sequence that forms a stable hairpin, also has a sequence at the 5' end of the HNA which completes the BamHI sequence formed by the hybridization of SEQ ID NO. 42 and SEQ ID NO. 43. Naturally, termination of the polymer after addition of only 3 BNAs is for the purpose of simplicity in demonstrating the invention. As described above, this polymerization may he continued essentially indefinitely to amplify the signal of the PNA-TNA hybridization event. Once the HNA hybridizes to the growing chain of BNAs, the polymer is capped and no further extension of the polymer is possible.

EXAMPLE 4

Preparation of TBAs and BBAs, Labeling, and Immobilization Thereof

The TBAs and BBAs which may be used according to the instant invention include any substance which can specifically bind to the TBRs and BBRs formed by hybridization of the PNAs, TNAs and BNAs. Use of DNA binding proteins forms one example of such substances. For this example, the TBA is the dimer of the DNA binding portion of p50, and the BBA is the lambda cro protein. These proteins may be produced according to methods known in the art. The genes for both of these proteins have been cloned. Thus, these proteins are recombinantly produced and purified according to methods known in the art. Furthermore, these proteins are labeled, either with a radioisotope, such as radioactive iodine, or with an enzyme, such as beta-galactosidase or horseradish peroxidase, or with a fluorescent dye such as fluorescein or rhodamine, according to methods well known in the art. In addition, either or both of the TBA and BBA may be immobilized on a solid surface such as the surface of a microtiter plate or the surface of a bead, such as a colored bead of diameter anywhere from 0.01 to 10 μm. The labels on the TBAs and BBAs may be the same or different.

In this example, the TBA containing the dimeric p50 DNA binding domain is labeled with rhodamine, while the BBA, cro, is labeled with fluorescein. Accordingly, upon hybridization of the PNAs, TNAs, BNAs and HNAs as described in this patent disclosure and the foregoing and following examples, the nucleic acid hybrids, if formed, are contacted with excess labeled TBA and cro. The fluorescence of these labels is measured according to known methods and, detection of both signals is indicative of the presence of 1/2 TBR sequences in the TNA. The differential signal produced by the fluorescence of the NF-kB and cro is a measure of the degree to which the polymerization of BNAs onto the PNA-TBA hybrid has resulted in amplification of the signal. Amplification from one to over a thousand fold is contemplated according to the method of this invention.

EXAMPLE 5

Hybridization of two PNAs with a TNA and Discrimination Between a TNA and a CNA

The PNAs, PNA1, SEQ ID NO. 40 and PNA2, SEQ ID NO. 45, are used in about ten-fold molar excess over the concentration of TNAs in a test sample. For this example, an isolated duplex HIV LTR, wherein one strand of which has the sequence SEQ ID NO. 37, shown in FIG. 7, and the other strand of which is complementary to the sequence shown in FIG. 7, is used as the TNA. A duplex isolated CNA is also used in this example, one strand of which has the same sequence as SEQ ID NO. 37, except that, in the first NF-kB binding site shown in FIG. 7, at the center of the binding site, position 1 in FIG. 7, instead of a "T," there is an "A," the complementary strand of which therefore mismatches with the SEQ ID NO. 40 PNA at that location.

SEQ ID NO. 40 and SEQ ID NO. 45 are both added to separate reactions, the first containing the above described TNA and the second containing the above described CNA. The samples are solubilized in an appropriate hybridization buffer, such as 10 mM Tris (pH 7.5), 1 mM EDTA. The samples are heated to about 90° C. for about five minutes to strand separate the duplex TNAs and CNAs in the samples, and then the samples are allowed to cool to allow strands of PNAs, TNAs and CNAs to anneal.

Once the hybridization has gone to completion, which can be determined according to known methods such as by calculating the t1/2 based on base compositions and annealing temperature according to known methods, the SEQ ID NO. 40 PNA is polymerized by addition of BNAs as in Example 2 and the SEQ ID NO. 45 PNA2 probe is polymerized with BNAs starting with Sph1 recognition site overhang. Following addition of the BNAs and a brief hybridization period, the separate samples are added to beads coated with covalently immobilized NF-kB, and the NF-kB is allowed to bind to any TBRs formed in the TNA and CNA samples. After about 15 minutes of binding, the samples are washed twice with about three volumes of an appropriate washing buffer, such as 10 mM Tris, pH 7.5, 100 mM NaCl, or another buffer predetermined not to interfere with NF-kB, or bacteriophage lambda CI repressor protein binding activity. After each wash, the beads are allowed to settle under gravity or by brief centrifugation. This removes any nucleic acids which do not have a perfect NF-kB binding site formed by hybridization of the PNA1 and TNA sequences.

After the final wash, bacteriophage lambda CI repressor protein labeled with a radioactive isotope, such as with radioactive iodine, or labeled with an enzyme, such as horseradish peroxidase, with colored beads, or with a fluorescent label is added to each sample. The samples are then washed several times (about 3) with several volumes (about 2) of an appropriate washing buffer such as 10 mM Tris, pH 7.5, 100 mM NaCl, or another buffer pre-determined not to interfere with NF-kB, or bacteriophage lambda CI repressor protein binding activity. After each wash, the beads are allowed to settle under gravity or by brief centrifugation. Following the last settling or centrifugation, the bound label is quantitated by detecting the bound radioactivity, liberated color in an enzymatic assay, color of bound beads, or fluorescence detection. Alternatively, an anti-CI antibody can be added and a standard sandwich enzyme linked immunoassay or radioimmunoassay performed to detect bound repressor. In addition, as a negative control (background), all of the foregoing manipulations are carried out in tandem with a sample in which beads are used having no immobilized NF-kB.

As a result of the foregoing assay, the control and CNA containing samples have similarly low signals while the TNA containing sample has a signal well above background.

EXAMPLE 6

A Test Kit for the Detection of HIV

A. Kit contents:
1. Microtiter plate.
2. 1 mg/mL solution of recombinantly produced NF-kB in tris-buffered saline.
3. Tube containing single stranded HIV PNAs (a mixture of pre-mixed oligonucleotides encoding two NF-kB 1/2 binding sites, i.e. a mixture of SEQ. ID. Nos. 7 and 8).
4. Tube containing single stranded human genomic PNA, SEQ ID NO. 1.
5. Tube of nuclease (PstI).
6. Tube of protease.
7. Tube containing pre-polymerized BNA's, 100 repeat units of bacteriophage lambda $O_R$, capped with an HNA but with free 1/2 BBRs available for binding to PNA-TNA hybrids.
8. Tube of horseradish peroxidase (hrp) conjugated cro.
9. Tube of hrp colored substrate.
10. Tris buffered saline, 100 mL.
11. Lancet.
12. Reaction tubes A, B, C, each containing 250 μL of distilled water.
13. Medicine dropper.

B. Assay method:
(a) The microtiter plate (item 1) is coated with the solution of recombinantly produced NE-kB (item 2) at a concentration of 1 mg/mL in tris buffered saline overnight at 4° C., with rocking.
(b) Three drops of blood of the test taker is obtained by pricking a finger with the lancet (reagent 11), and a drop of blood is dispensed into each of reaction tubes A, B, and C (reagent 12).
(c) Into each tube is dispensed one drop of protease solution (reagent 6) with the medicine dropper (item 12) and the tube agitated and allowed to sit for 5 minutes.
(d) One drop of nuclease (item 5) is added to each of tubes A-C using the medicine dropper and the tubes agitated and allowed to sit for 10 minutes.
(e) One drop of item 3 is added to tube A (test sample); one drop of item 4 is added to tube B (positive control); and one drop of saline (item 12) is added to tube C as a negative control. The tubes are heated to 50° C. in hot water and allowed to cool to room temperature over one hour.
(f) While the hybridization is allowed to occur in step (d), the excess protein is drained from the surface and the microtiter plate, from step (a), and the plate is rinsed with tris buffered saline (tube 10).
(g) The contents of tubes A-C from step (e) are transferred to three wells of the microtiter plate and allowed to stand for 1 hour with rocking.
(h) The microtiter wells containing the contents of tubes A-C are rinsed with tris buffered saline and emptied.
(i) One drop of item 7 is added to each well and allowed to hybridize with any 1/2 BBR sites bound to the plate, over one hour, followed by three rinses with tris buffered saline.
(j) One drop of item 8 is added to each well and cro is allowed to bind to any bound BNA's over 10 minutes, followed by five, one mL washes with tris-buffered
(k) One drop of hrp substrate is added to each well and color allowed to develop.

C. Results:
If wells A and B both show color development, and well C does not, the test is valid and the subject has been infected with HIV. If only well A shows color development, or if well C shows color development, the test has been performed incorrectly, and is invalid. If wells A and C show no color development but well B does, the test is valid and the individual has not been infected with HIV.

EXAMPLE 7

Production of Various Novel TBAs

Novel TBAs for use according to the instant invention are prepared as follows:

(a) NFkB/NF-kB (HIV-Detect I). A nucleic acid encoding any one of SEQ ID NOS. 63-71 or a like NF-kB DNA binding protein, is fused, in frame, to a nucleotide sequence encoding an assembly sequence, such as cro, such that the NF-kB DNA recognition sequence is encoded at amino or carboxy terminus of the cro sequence. Optionally, a linker sequence is provided between the NF-kB sequence and the cro sequence. At the other terminus of cro, a nuclear localization signal sequence, such as SEQ ID NO. 72, is optionally provided. Further, asymmetry sequences are optionally provided at the cro terminus unused by the NF-kB recognition sequence. Examples of complete TBAs are shown below.

(b) NF-kB/SP1 (HIV-Detect II). In a similar fashion to that described in (a) above, a recombinant coding sequence encoding an NF-kB recognition domain is prepared. In a separate construct, instead of SEQ ID NOS. 63-72, the coding sequence for the DNA recognition portion of SP1 is included. Such a sequence should encode all or a functional part of SEQ ID NO. 73, which is that portion of the SP1 transcription factor exhibiting DNA binding (see Kadonaga et al. [1987] *Cell* 51:1079-1090). The NF-kB-encoding vector and the SP1-encoding vector are then co-transfected into an appropriate expression system such as is well known in the art. A monomeric NF-kB recognition unit is added to complete the NF-kB recognition dimer after the assembly of the SP1 and NF-kB recognition units by the chaperone. The asymmetry sequences prevent the formation of NF-kB or SP1 dimers and direct, instead, the formation of NFkB-SP1 heterodimers (i.e., HIV-Detect II), which are then isolated from the expression system (mammalian or bacterial cells) by known methods.

(c) SP1/SP1 TBAs (HIV-Detect III). As described in (b) above, an SP1-encoding TBA construct is prepared. However, only this construct is transfected into the expression system, and asymmetry sequences allowing the formation of SP1-SP1 dimers are included.

(d) SP1-TATA (HIV-Detect IV). As described in (b) above, an SP1-encoding TBA recombinant is produced. In addition, a recombinant encoding a TBA having the binding sequence, SEQ ID NO. 74, or like sequence encoding a TATA recognition unit is prepared with asymmetry sequences complementary to those included in the SP1 TBA-encoding construct. These constructs are co-transfected and the heterodimers isolated by standard methods, including affinity purification on a DNA column having the appropriate SP1-TATA target binding regions.

(e) SP1-E2 (HPV-Detect I). An SP1-encoding construct is prepared as in (b) above. An E2 TBA-encoding construct is prepared by using a sequence encoding any one of SEQ ID NOS. 75-84 and 94-98 which are papillomavirus E2 DNA recognition units (see Hegde et al. [1992] *Nature* 359:505-512) or like recognition units, is prepared and co-transformed or co-transfected with the SP1 TBA-encoding construct. Monomeric E2 recognition unit is added to the complete E2 recognition dimer after the assembly of the E2-SP1 recognition unit by the chaperone. The heterodimer HPV-DetectI is isolated according to known methods.

(f) E2-E2 (HPV-Detect II). As described above in (e), an E2 TBA-encoding construct is prepared, except that asymmetry sequences are included which permit the formation of E2 dimers. The expressed dimers are then isolated by known methods including affinity for a dimeric E2 binding site on a DNA affinity column.

(g) E2-TATA (HPV-Detect III). As described above in (e) and (d), E2 and TATA binding TBAs are prepared (respectively), except that asymmetry sequences are included which enhance the formation of heterodimers rather than homodimers. These constructs are then co-expressed and the heterodimers are isolated.

(h) TATA-TATA (HPV-Detect IV). As described above in (a) and (d), a TATA binding TBA-encoding construct is prepared using asymmetry sequences that encourage this homodimer formation and the homodimer is isolated.

(i) Other TBAs. As described above for HIV and HPV TBAs, TBAs for any given pathogen or disease state may he produced by identifying specific DNA binding proteins and forming an expression construct using appropriate linker, assembly, and asymmetry sequences.

EXAMPLE 8

In a similar fashion to the assay described in Example 5, a more stringent assay is produced by using the duplex NF-kB-SP1 binding protein prepared according to Example 6. Accordingly, the probes shown in FIG. 7 and used in Example 5 may be lengthened to reduce the interprobe distance and thereby reduce the flexibility of the DNA in the TNA.

EXAMPLE 9

Production of "High-Order" TBAs

By the appropriate use of asymmetry sequences, TBAs are produced which are dimers, trimers, tetrameres, pentamers, or hexamers of particular DNA recognition units. In this fashion, a hexameric TBA is produced by making a first NF-kB p50 dimeric TBA using asymmetry sequences which enable dimer formation. In addition, the asymmetry sequences enable the tetramerization of the p50 dimer with an SP1-SP1 dimer. Finally, additional asymmetry sequences direct the hexamerization with a dimer exhibiting nuclear localization sequences. This is accomplished by incorporating, for example, asymmetry sequences from insulin, which in nature forms hexamers. This hexamer formation is directed by the sequences, SEQ ID NOS. 85 (A) and 86 (B), 87 (A) and 88 (B), 89 (A) and 90 (B), and 91 (A) and 92 (B) (see FIGS. 13 and 14).

Because of the extremely high affinity for the HIV-LTR that can be generated using a multimeric TBA, the compounds having this structure and which can be used for this purpose are referred to herein as "HIV-Lock."

An optimal HIV-Lock is defined by footprinting (according to methods well known in the art) TBAs bound to TBRs in the HIV LTR to confirm that the binding affinity of each DNA binding protein contributing to the formation of the multimeric TBA complex is downshifted relative to the affinity for any natural target sequence (i.e. CNAs) from which the DNA binding recognition unit of the TBA is derived. Any concomitant loss in binding affinity for the HIV TBRs is more than compensated for upon formation of the multimer as described below.

There may be competition between the binding of each component TBA for its TBR and assembly, via asymmetry sequences to form the multimer. This is obviated by adjusting the linkers between the chaperone and asymmetry sequences in each TBA component such that these competing events are uncoupled. The resultant reduction in the dimensionality of diffusion (effective concentration increase) for the TBA asymmetry and assembly components results in efficient formation of the multimeric complex.

On the basis of the footprinting, the length and composition of linkers is adjusted to achieve optimal discrimination between target HIV sequences and natural sequences. In this fashion, although each component TBA will have a low affinity for CNA and TBR sequences, the multimeric complex will have an extremely high affinity for the now expanded TBR recognized by the multimeric complex (the square of the affinity of each TBR recognized by each component TBA of the multimeric TBA), while still having a low affinity for CNAs. In the same fashion, other multimeric TBA complexes, aside from HIV-Lock, are prepared.

TBAs which can be formed in this fashion include the following sequences, which are assembled by linking either the protein subunits or nucleic acid sequences encoding these subunits, as follows:

| Set | Link Sequences from Groups |
|---|---|
| A | I + II + III |
| B | IV + V + III |
| C | IV + III | wherein groups I-V consist of sequences selected from:

| Group | Selected from Sequences |
|---|---|
| I | Any of SEQ ID NOS. 85-92 |
| II | Met Ser, linked to any of SEQ ID NOS 104-106, each of which is linked to SEQ ID NO. 99. |
| III | SEQ ID NO. 100 linked to any of SEQ ID NOS. 75-84 or 94-98; SEQ ID NO. 101 linked to either SEQ ID NO. 74 or SEQ ID NO. 93; or SEQ ID NO. 102 linked to SEQ ID NO. 74 or SEQ ID NO. 93; or any of SEQ ID NO. 72, 103, 73, or 63-71. |
| IV | Any of SEQ ID NOS. 104-106. |
| V | SEQ ID NO. 99. |

Specific examples of such TBAs are SEQ ID NOS. 109-116, assembled as follows:

| Set | SEQ ID NO. | Link SEQ IDS |
|---|---|---|
| A | 109 | 85 + Met Ser + 104 + 99 + 100 + 94 |
| A | 110 | 85 + Met Ser + 104 + 99 + 72 |
| A | 111 | 86 + Met Ser + 105 + 99 + 102 + 74 |
| A | 112 | 86 + Met Ser + 106 + 99 + 73 |
| A | 113 | 89 + Met Ser + 106 + 99 + 63 |
| C | 114 | 106 + 64 |
| C | 115 | 105 + 64 |
| B | 116 | 106 + 99 + 73 |

In this fashion, choosing between appropriate asymmetry sequences, assembly sequences, and DNA recognition units, many different TBAs may be formed. Furthermore, sets of these, such as SEQ ID NOS. 114 and 115, will associate with each other but dimers of SEQ ID NO. 114 or 115 will not form due to charge repulsion in the mutated assembly sequences (SEQ ID NO. 104 is cro; SEQ ID NO. 105 is a novel mutated, negatively charged cro, and SEQ ID NO. 106 is a novel mutated, positively charged cro).

Naturally, given the amino acid sequence of these TBAs, one of ordinary skill could produce recombinant nucleic acid clones encoding these, and such recombinant clones naturally form an integral part of this invention.

EXAMPLE 10

HIV Test Using "HIV-LOCK"

In much the same method as used in Example 6, the "HIV-LOCK" produced according to Example 9 is used as the TBA, reagent 2, with similar results.

EXAMPLE 11

HIV Test Using "HIV-LOCK" When Testing Blood for Donation

When the quantity of blood to be tested is not limiting, as when samples of blood for donation are to be tested for HIV contamination, tests similar to Example 6 are run, but for each of tubes A-C, about 5 mL of blood is pelleted in a tabletop centrifuge. Other reagents are scaled up as necessary to handle the larger quantity of TNA present in the sample.

EXAMPLE 12

"HIV-LOCK" as an Anti-HIV Therapeutic Agent

"HIV-LOCK" produced according to Example 9 is formulated as a 1 mg/mL solution in liposomes and injected intravenously into a subject who has been tested and confirmed to be infected with HIV. A dose of about 0.1 mg to 100 mg of "HIV-LOCK"/kilogram body mass is infused over a twenty-four hour period and the concentration of HIV p24 in the patient's serum monitored. The treatment is repeated as often as necessary, such as when elevations in the serum p24 occur.

EXAMPLE 13

Use of an HIV-TBA Construct as a Therapeutic

A recombinant retroviral or like vector is used to deliver a construct encoding an HIV-LTR binding TBA to an infected patient. The vector encodes a chaperone, such as cro, and sequences DNA for binding portions of p50. The same vector also encodes a chaperone on which an SP1 TBA folds. Asymmetry sequences are provided such that upon co-expression of the p50-TBA and the SP1-TBA in a single HIV infected cell in vivo, an immediate association occurs between these TBAs, while at the same time preventing any association between the DNA binding portion of p50 and endogenous p50 or p65 monomers. NLS sequences are also provided in the TBAs so that, upon dimer formation, the TBA immediately relocates to the nucleus of the cell and binds specifically to integrated HIV sequences, thus preventing any transcription from that locus.

For this purpose, it is desirable to select sequences encoding DNA binding domains such that the expressed monomers are assembled into a TBA which does not bind to natural human sequences. Thus, it is only upon binding of the TBA components to their target sequences that association between all components of the TBA occurs to form a complex which tightly and specifically binds the HIV LTR.

EXAMPLE 14

Diagnostic Test Kit for Human Papillomavirus

This diagnostic for human papillomavirus takes advantage of the known differential between benign and carcinogenic HPV to provide a test which indicates the susceptibility to malignancy in a patient. The papillomaviruses are a group of small DNA viruses associated with benign squamous epithelial cell tumors in higher vertebrates. At least 27 distinct human types of papillomaviruses (HPVs) have been found; many of these have been associated with specific clinical lesions. Four of these, HPV-6, HPV-11, HPV-16, HPV-18, and HPV-33 have been associated with human genital tract lesions. In general, HPV-6 and HPV-11 DNAs have been found associated with benign lesions of the genital tract. HPV-16, HPV-18, and HPV-33 have also been found associated with premalignant and malignant lesions and are transcribed in most cell lines established from cervical carcinomas. HPV-16, HPV-18, and HPV-33 are likely to be only two members of a large set of HPV DNAs associated with malignant human cervical carcinomas.

Animal models have shown that benign papillomavirus lesions can progress to malignant lesions in the presence of a co-carcinogen. HPV DNA has been found in metastases of cervical carcinomas. In malignant cervical lesions, HPV DNA is usually integrated into the human genome, but there may also be extrachromosomal HPV DNA present. Integration of HPV to form the provirus usually results in the disruption of the viral E2 open reading frame (ORF). Despite disruption of the E2 ORF, and examination of cell lines from several cervical carcinomas has shown transcriptionally active and integrated HPV-16 and HPV-18. When HPV-16 genomes which are present in the human cervical carcinoma cell lines SiHa and CaSki have been examined, there are differences found in the integration of HPV-16. In the SiHa line, the single HPV-16 genome integration occurred at bases 3132 and 3384, disrupting the E1 and E2 ORFs with a deletion of 0.3 kb. An additional 50-basepair deletion of HPV-16 DNA resulted in the E2 and E4 OFRs being fused. The 5' portion of the HPV-16 DNA, consisting of the disrupted E2 ORE, is ligated to continuous human right flanking sequences. In addition, a single additional guanine is detected at nucleotide 1138 in the middle of the E1 ORF. This basepair addition results in the fusion of the E1a and E1b ORFs to a single E1 ORF.

The complete genome of HPV-16 is available on GenBank as accession number K02718; the complete genome of HPV-33 is available on GenBank as accession number M12732; the complete genome of HPV-18 is available on GenBank as accession number X05015.

As a preliminary screen, the fact of an HPV infection is established for a given cervical biopsy sample by a simple "yes/no" type of analysis using, for example, any or all of the PNAs SEQ ID NOS. 46-53 and an E2 TBA as described above (i.e., fragment DNA, binding the PNA, immobilize with the TBA, and detect signal with BNAs and BBAs).

Once a biopsy sample is found to be positive for HPV, additional information is obtained as to the malignancy potential of the HPV by analyzing the integration status of the virus in the human genome.

1. Fragment the DNA in the cervical biopsy sample and hybridize to a blocking probe having the sequence, SEQ ID NO. 60. This probe will bind to all the fragments in the DNA which have not spliced out the 0.3 kb fragment.
2. Expose the DNA in the biopsy sample to a PNA having the sequence, SEQ ID NO. 61. This probe will only bind to fragments which have deleted the 0.3 kb fragment (the blocking probe will prevent the looping out of the large deletion segments if present).
3. A PNA having SEQ ID NO. 62 is hybridized with SEQ ID NO. 41 to form a BBR which will bind to cro or λ CI repressor as a BBA, leaving a single-stranded portion capable of hybridizing with the TATA site on SEQ ID NO. 61. This added to form a TBR on the 5' end of the large deletion.
4. The TBR is immobilized by a TBA having a TATA binding protein DNA recognition unit.
5. The bound fragments are detected by adding BNAs and BBAs as described above.

Detection of signal in this assay indicates that the large fragment is deleted in HPV present in the TNA. Since this deletion is correlated with malignancy, this assay provides insight into the malignancy potential of the HPV infection. This conclusion can be confirmed by performing an analogous assay based on the deletion of the 52-basepair fragment which is also correlated with HPV-induced malignancy.

The TBP recognition unit used in the TBA for this assay may be chosen, for example, from a sequence such as SEQ ID NO. 70 or SEQ ID NO. 93.

EXAMPLE 15

Recombinant HIV-LOCK™ Production

Phase One—Preparation of DNA to Produce the HIV-Lock™. In vitro mutagenesis of the coding regions of the naturally occurring, cloned components of the HIV-Lock™ which need to be modified is performed with a MutaGene Phagemid kit. The modified protocol includes the use of a Blue-script plasmid containing each of the binding components of HIV-Lock™. These are transformed into competent cells and uracil-containing phagemids are grown. Single stranded DNA is extracted and used as a template for the mutagenic strand. Oligonucleotides containing the desired mutations, including the incorporation of a novel restriction site, are synthesized and treated with polynucleotide kinase and ATP. The kinase treated oligonucleotides are annealed to the single-stranded template, and a mutagenic strand is synthesized and ligated according to the MutaGene protocol, with the exception that Sequenase 2.0 provides the polymerase. Libraries are screened using both $g$-$^{32}$P end-labeled nucleotides containing sequences complementary to the introduced mutations and by isolating the plasmid DNA and identifying the mutants by the presence of the introduced restriction site. The mutations are also confirmed by sequencing with a Sequenase kit. The HIV-Lock™ DNA is cloned into the baculovirus expression system with a polyhedron promotor.

Phase Two—Production of HIV-Lock™ Proteins Using Baculovirus. Sf-9 cells are cultured to a pre-determined density (about $1 \times 10^6$ cells/ml, log phase), infected with the baculovirus containing the HIV-Lock™ instructions and harvested to recover the recombinant proteins comprising the HIV-Lock™. In the scale-up process, cultures are expanded from flasks to spinners and subsequently to bioreactors. Following infection the cells are harvested at 12, 24, 36 and 48 hours for the protein. Indices of viability are monitored throughout the entire process.

Phase Three—Purification of the HIV-Lock™ Proteins The harvested proteins are first separated from particulates by flow-through ultracentrifugation to facilitate downstream purification. The centrifuged product is then sterile filtered. Extracts are then centrifuged at 40,000 rpm at 4' C. for 30 minutes and aliquots are immunoprecipitated with polyclonal rabbit antibody against one of the HIV-Lock™ components. Immunoprecipitated proteins are run on an SDS-10% PAGE gel.

Phase Four—Test of HIV-Lock™ Proteins Against HIV DNA, Mobility shift assays are carried out using an oligonucleotide probe comprising elements of the HIV long terminal repeat and fragments containing NFKB binding DNA associated with kappa light chain and microglobulin regulation. The oligonucleotide is annealed to its complimentary strand and end-labeled with $g$-$^{32}$P ATP.

Footprinting is accomplished by combining small ($10^{-15}$ M) of radiolabeled HIV LTR DNA with a slightly larger amount of HIV-Lock™ in a buffer at room temperature for 10 minutes. Dithiothreitol is added prior to the addition of protein. Iron (II), EDTA, hydrogen peroxide and sodium ascorbate are added and the reaction mixture is incubated. A quenching agent is added and the products are analyzed suing denaturing gel electrophoresis. This is done for different concentrations of protein. The resulting gel is imaged using a phosphoimager scanner and the resulting high resolution image file is analyzed to abstract the binding affinity of HIV-Lock™ for the HIV DNA relative to cellular DNA.

Multiple design and testing iterations may be used in order to refind binding of HIV-Lock™ and other TBAs for HIV and other organisms. This process makes it possible to design binding assemblies such that the binding assembly is not competitive with the wild type proteins for single binding sites in the genome samples. The development of TBAs for other organisms and TNAs for sequences within these organisms can be made using the aforementioned method. This method is valid when producing binding assemblies for all nucleic acid TBRs including DNA-DNA, DNA-RNA and RNA-RNA hybrids and combinations of these hybrids.

EXAMPLE 16

Method for Identifying Nucleic Acid Binding Molecules for Production of TBAs and BBAs of the Invention:

In the method of this invention, target binding assemblies and booster binding assemblies are assembled by identifying nucleic acid binding molecules, and linking the nucleic acid binding portions of the molecules in such a fashion as to achieve TBAs which discriminate between particular target sequences and even closely related sequences. One method for identifying the nucleic acid binding molecules involves the following steps:
1. Obtaining a biological sample containing the target nucleic acid. This could be, for example, an organism or a tissue extract infected with a pathogen.
2. Fragmenting the sample so as to expose the nucleic acids and to reduce the size complexity of the nucleic acids contained in the sample.
3. Contacting a first aliquot of the fragmented nucleic acids with a control buffer medium and contacting a second aliquot of the fragmented nucleic acids with the control buffer medium containing a known profile of nucleic acid binding molecules.
4. Analyzing the two aliquots to identify fragments which have altered behavior in the aliquot contacted with the target binding molecules as opposed to the control aliquot. This is accomplished by single dimension gel electrophoresis, two dimension gel electrophoresis, high performance liquid chromatography, paper chromatography or any other means which reveals a different behavior of the nucleic acid fragments when bound to a nucleic acid binding molecule as opposed to when the nucleic acid fragment is unbound.
5. Identifying and isolating fragments which do exhibit altered behavior when contacted with the nucleic acid binding molecule and either sequencing the nucleic acid fragment to determine whether known nucleic acid binding molecule motifs are present, or directly identifying the nucleic acid binding molecule bound to the nucleic acid. The latter can be achieved, for example, by contacting a two dimensional grid of the electrophoresed nucleic acids with differentially labeled antibodies which bind to the various nucleic acid binding molecules.

In this method, preferably nucleic acid motifs are used for either diagnostic or therapeutic purposes wherein the target nucleic acid has more than a single utilizable nucleic acid binding molecule target. In this way, a complex target binding assembly can be generated which takes advantage of the proximity of different nucleic acid binding molecular motifs to enhance the specificity of the TBA assembled from the individual nucleic acid binding components identified. The various nucleic acid binding portions of the nucleic acid binding molecules are then assembled into the complete TBAs as described above, for example, for HIV-LOCK™.

EXAMPLE 17

Method of Identifying Specific RNA Sequences in a Sample

According to the methods and compositions taught in this invention, any nucleic acid sequence can be specifically identified. Identification of target HIV RNA in a sample is achieved by obtaining a sample of a patients blood or other biological fluid or extract which may contain the HIV RNA, and testing for the presence of TAR binding sites. Tat is a positive regulator of HIV replication which binds to the TAR region of the HIV RNA. The smallest naturally occurring, fully active form of HIV-Tat is 72 amino acids in length, SEQ Id. 118 herein. Tat contains at least two functional domains, and transactivates gene expression from the HIV long terminal repeat (HIV LTR). Tat binds to an RNA stem loop structure formed from the self-hybridization of sequences in TAR, which is just 5' to the HIV LTR. HIV TAR RNA forms a dinucleotide bulge and two stem-loop structures (Rhim et al. 1994 Virology:202, 202-211). The Tat (SEQ. Id. 118) binds to this structure with lower avidity than does Tat variants wherein Ala58 is a threonine or where His65 is an Asp residue. (Derse et al., 1993 Virology:194,530-536). Utilizing these facts in the instant method is accomplished by:
1. Fragmenting a biological sample to expose the nucleic acids and reduce the size complexity of the nucleic acids.
2. Contacting a TBA with the sample which identifies a hybrid TAR binding protein sequence and a proximate flanking sequence in the HIV genome. The TBA used for this purpose is assembled on cro as the chaperone using Tat as the HIV RNA specific binding molecule. To provide specificity such that cross-talk between the HIV TAR site and closely related TAR sites which may be present due to such other pathogens as cytomegalovirus, the TBA also has an antibody component which recognizes the DNA-RNA hybrid target binding region formed when a probe nucleic acid binds to the HIV LTR RNA.
3. Eliminating any "cross-talk" produced by binding of Tat to the TAR region of the HIV RNA due to such contaminants (cousin RNAs) as the CMV TAR sequence by contacting the reaction with excess Tat variant (either the Ala58 to Thr or the His65 to Asp variants) which bind more avidly. In this way, single binding events due to the TBA binding to a cousin RNAs are competed from the nucleic acid sample by the Tat variant. On the other hand, by appropriately selecting the affinity of the double binding achieved as a result of the antibody and Tat, the TBA is not displaced from true targets. This process is illustrated in FIG. 16. In another aspect of this same method, the TBA could be one in which, rather than using a variant of Tat, an antibody is used which recognizes this nucleic acid segment, and the TBA used is a double antibody TBA.

In an alternate version of this method, a probe nucleic acid may be used which hybridizes with the HIV LTR RNA. Accordingly, a duplex segment of the LTR sp1 sites can be created as part of the target binding region. This region of the HIV RNA flanks the TAR region which is 5' to the LTR but is in close proximity thereto. A TBA containing Tat and two Sp1 binding units is chaperoned to provide Tat binding to TAR and Sp1 binding to the Sp1 binding sites. Amplification and detection is then carried out by adding appropriate BNAs, BBAs and HNAs. In yet another alternative, PNAs having Seq. ID. 38 and Seq. ID. 39 (see FIG. 7) could be used. A TBA is used which contains one or more Sp1 binding units and an antibody unit which binds to the DNA-RNA hybrid produced from sample RNA and the Seq. Id. 38 PNA. Appropriate BNAs, BBAs and HNAs are then added to amplify the signal.

Naturally, those skilled in the art will recognize that other TBA and TNA combinations could be used to optimize the methods exemplified herein.

It should be understood that the examples and embodiments described herein are for illustrative purposes only and that various modifications or changes in light thereof will be suggested to persons skilled in the art and are to be included within the spirit and purview of this application and the scope of the appended claims. It will be understood that sequences provided herein are exemplary only and that other like sequences suggested by these could he used in the methods of this invention. It will also be understood that although any sequence provided herein might be designated as linear, it could be used in a circularly or otherwise permuted form and although designated as not being anti-sense, it could be used in the coding or non-coding form or to bind to coding or non-coding complementary sequences.

What is claimed is:

1. An isolated target binding assembly (TBA) comprising a first and a second nucleic acid recognition unit, wherein:
said first nucleic acid recognition unit is capable of binding with specificity to a first target nucleotide sequence contained within a target polynucleotide;
said second nucleic acid recognition unit is capable of binding with specificity to a second target nucleotide sequence contained within a target polynucleotide;
said nucleic acid recognition units are polypeptides and are the same or different; and
wherein said TBA comprises a sequence selected from the group consisting of:
A. I+II+III;
B. IV+V+III; and
C. IV+III;
wherein
I indicates any of SEQ ID NOS:85-92;
II indicates Met Ser, linked to any of SEQ ID NOS:104-106, each of which is linked to SEQ ID NO:99;
III indicates SEQ ID NO:100 linked to any of SEQ ID NOS:75-84 or 94-98; SEQ ID NO: 101 linked to either SEQ ID NO:74 or SEQ ID NO:93; or SEQ ID NO:102 linked to SEQ ID NO:74 or SEQ ID NO:93; or any of SEQ ID NOS:72, 103, 73, or 63-71;
IV indicates any of SEQ ID NOS. 104-106; and
V indicates SEQ ID NO:99.

2. The TBA of claim 1, wherein each said target nucleotide sequence includes at least 7 contiguous nucleotides.

3. The TBA of claim 1, wherein said first nucleic acid recognition unit is capable of binding said first target nucleotide sequence at the same time that said second nucleic acid recognition unit is bound to said second target nucleotide sequence, when said first and second target nucleotide sequences:
are both contained within the same target polynucleotide; and
are separated from one another by intervening nucleotide(s).

4. The TBA of claim 3, wherein each said target nucleotide sequence includes at least 7 contiguous nucleotides.

5. The TBA of claim 2, wherein said first and second nucleic acid recognition units are DNA-binding polypeptides.

6. The TBA of claim 3, wherein said first and second nucleic acid recognition units are DNA-binding polypeptides.

7. The TBA of claim 4, wherein said first and second nucleic acid recognition units are DNA-binding polypeptides that bind reversibly and non-covalently to double-stranded DNA.

8. The TBA of claim 7, wherein said first and second nucleic acid recognition units, when considered separately, each have a binding affinity $K_d$ for their respective target nucleotide sequence that is numerically greater than $10^{-6}$ M.

9. A composition comprising the TBA of claim 1 bound to a target polynucleotide comprising said first target nucleotide sequence and said second target nucleotide sequence, whereby transcription of a gene contained within the target polynucleotide is hindered.

* * * * *

```
                         SEQUENCE LISTING (1) GENERAL INFORMATION:

(iii) NUMBER OF SEQUENCES: 118

(2) INFORMATION FOR SEQ ID NO: 1:

(i) SEQUENCE CHARACTERISTICS:
          (A) LENGTH: 13 base pairs
          (B) TYPE: nucleic acid
          (C) STRANDEDNESS: both
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

TGGGGATTCC CCA                                                              13

(2) INFORMATION FOR SEQ ID NO: 2:

(i) SEQUENCE CHARACTERISTICS:
          (A) LENGTH: 13 base pairs
          (B) TYPE: nucleic acid
          (C) STRANDEDNESS: both
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 2:

AAGGGACTTT CCC                                                              13

(2) INFORMATION FOR SEQ ID NO: 3:

(i) SEQUENCE CHARACTERISTICS:
          (A) LENGTH: 13 base pairs
          (B) TYPE: nucleic acid
          (C) STRANDEDNESS: both
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 3:

AGGGGACTTT CCG                                                              13

(2) INFORMATION FOR SEQ ID NO: 4:

(i) SEQUENCE CHARACTERISTICS:
          (A) LENGTH: 15 base pairs
          (B) TYPE: nucleic acid
          (C) STRANDEDNESS: both
          (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 4:

GCTGGGGACT TTCCA                                                        15

(2) INFORMATION FOR SEQ ID NO: 5:

(i) SEQUENCE CHARACTERISTICS:
            (A) LENGTH: 15 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

ACAAGGGACT TTCCG                                                        15

(2) INFORMATION FOR SEQ ID NO: 6:

(i) SEQUENCE CHARACTERISTICS:
            (A) LENGTH: 13 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 6:

CCGGGTTTTC CCC                                                          13

(2) INFORMATION FOR SEQ ID NO: 7:

(i) SEQUENCE CHARACTERISTICS:
            (A) LENGTH: 27 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

AAGGGACTTT CCGCTGGGGA CTTTCCA                                           27

(2) INFORMATION FOR SEQ ID NO: 8:

(i) SEQUENCE CHARACTERISTICS:
            (A) LENGTH: 27 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

AAGGGACTTT CCGCTGGGGA CTTTCCG                                          27

(2) INFORMATION FOR SEQ ID NO: 9:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 9:

GCTGGGGACT TTCCAGGGAG GCGTGG                                           26

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 10:

GCTGGGGACT TTCCAGGGGA GGTGTG                                           26

(2) INFORMATION FOR SEQ ID NO: 11:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 11:

GCTGGGGACT TTCCGGGGAG CGTGGC                                           26

(2) INFORMATION FOR SEQ ID NO: 12:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 12:

GCTGGGGACT TTCCGGGGAG GCGCGG                                                26

(2) INFORMATION FOR SEQ ID NO: 13:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 13:

GCTGGGGACT TTCCAGAGAG GCGTGG                                                26

(2) INFORMATION FOR SEQ ID NO: 14:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

GCTGGGGACT TTCCAGGGGA GGCGTG                                                26

(2) INFORMATION FOR SEQ ID NO: 15:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

GCTGGGGACT TTCCAGGGAG GCGTGG                                                26

(2) INFORMATION FOR SEQ ID NO: 16:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

GCTGGGGACT TTCCAGGGAG GCTGCC                                                26

(2) INFORMATION FOR SEQ ID NO: 17:

```
    (i) SEQUENCE CHARACTERISTICS:
        (A) LENGTH: 33 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 17:

TTTCCAGGGA GGCGTGGCCT GGGCGGGACT GGG                            33

(2) INFORMATION FOR SEQ ID NO: 18:

(i) SEQUENCE CHARACTERISTICS:
        (A) LENGTH: 33 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 18:

CGTGGCCTGG GCGGGACTGG GGAGTGGCGT CCC                            33

(2) INFORMATION FOR SEQ ID NO: 19:

(i) SEQUENCE CHARACTERISTICS:
        (A) LENGTH: 45 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 19:

CTACAAGGGA CTTTCCGCTG GGACTTTCC AGGGAGGCGT GGCCT                45

(2) INFORMATION FOR SEQ ID NO: 20:

(i) SEQUENCE CHARACTERISTICS:
        (A) LENGTH: 46 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 20:

CAGCAAGGGA CTTTCCGCTG GGACTTTCC AGGGGAGGTG TGGCCT               46

(2) INFORMATION FOR SEQ ID NO: 21:

(i) SEQUENCE CHARACTERISTICS:
        (A) LENGTH: 46 base pairs
        (B) TYPE: nucleic acid
```

```
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 21:

CATCAAGGGA CTTTCCGCTG GGGACTTTCC AGGGGAGGTG TGGCCT                46

(2) INFORMATION FOR SEQ ID NO: 22:

(i) SEQUENCE CHARACTERISTICS:
            (A) LENGTH: 46 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 22:

CAACAAGGGA CTTTCCGCTG GGGACTTTCC AGGGGAGGTG TGGCCT                46

(2) INFORMATION FOR SEQ ID NO: 23:

(i) SEQUENCE CHARACTERISTICS:
            (A) LENGTH: 45 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 23:

CTACAAGGGA CTTTCCGCTG GGGACTTTCC AGGGAGGCGT GGCAT                 45

(2) INFORMATION FOR SEQ ID NO: 24:

(i) SEQUENCE CHARACTERISTICS:
            (A) LENGTH: 44 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 24:

CTACAAGGGA CTTTCCGCTG GGGACTTTCC GGGGAGCGTG GCCT                  44

(2) INFORMATION FOR SEQ ID NO: 25:

(i) SEQUENCE CHARACTERISTICS:
            (A) LENGTH: 44 base pairs
            (B) TYPE: nucleic acid
            (C) STRANDEDNESS: both
            (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO: 25:

CTACAAGGGA CTTTCCGCTG GGGACTTTCC GGGGAGGCGC GGCT                            44

(2) INFORMATION FOR SEQ ID NO: 26:

(i) SEQUENCE CHARACTERISTICS:
            (A) LENGTH: 45 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 26:

CTACAAGGGA CTTTCCGCTG GGGACTTTCC AGAGAGGCGT GGACT                           45

(2) INFORMATION FOR SEQ ID NO: 27:

(i) SEQUENCE CHARACTERISTICS:
            (A) LENGTH: 46 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 27:

CTACAAGGGA CTTTCCGCTG GGGACTTTCC AGGGGAGGCG TGGACT                          46

(2) INFORMATION FOR SEQ ID NO: 28:

(i) SEQUENCE CHARACTERISTICS:
            (A) LENGTH: 46 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 28:

CTACAGGGGA CTTTCCGCTG GGGACTTTCC AGGGAGGCGT GGGGAG                          46

(2) INFORMATION FOR SEQ ID NO: 29:

(i) SEQUENCE CHARACTERISTICS:
            (A) LENGTH: 43 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 29:

CTACAGGGGA CTTTCCGCTG GGGACTTTCC AGGGAGGCTG CCT                43

(2) INFORMATION FOR SEQ ID NO: 30:

(i) SEQUENCE CHARACTERISTICS:
        (A) LENGTH: 48 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 30:

CTTTCCGCTG GGGACTTTCC AGGGAGGCGT GGCCTGGGCG GGACTGGG         48

(2) INFORMATION FOR SEQ ID NO: 31:

(i) SEQUENCE CHARACTERISTICS:
        (A) LENGTH: 45 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 31:

TTTCCAGGGA GGCGTGGCCT GGGCGGGACT GGGGAGTGGC GTCCC             45

(2) INFORMATION FOR SEQ ID NO: 32:

(i) SEQUENCE CHARACTERISTICS:
        (A) LENGTH: 59 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 32:

CTACAAGGGA CTTTCCGCTG GGGACTTTCC AGGGAGGCGT GGCCTGGGCG GGACTGGGG     59

(2) INFORMATION FOR SEQ ID NO: 33:

(i) SEQUENCE CHARACTERISTICS:
        (A) LENGTH: 59 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 33:

TTTCCGCTGG GGACTTTCCA GGGAGGCGTG GCCTGGGCGG GACTGGGGAG TGGCGTCCC     59

(2) INFORMATION FOR SEQ ID NO: 34:

(i) SEQUENCE CHARACTERISTICS:
        (A) LENGTH: 70 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 34:

```
CTACAAGGGA CTTTCCGCTG GGGACTTTCC AGGGAGGCGT GGCCTGGGCG GGACTGGGGA    60

GTGGCGTCCC                                                           70
```

(2) INFORMATION FOR SEQ ID NO: 35:

(i) SEQUENCE CHARACTERISTICS:
        (A) LENGTH: 61 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 35:

```
TATCACCGCC AGTGGTATTT ATGTCAACAC CGCCAGAGAT AATTTATCAC CGCAGATGGT    60

T                                                                    61
```

(2) INFORMATION FOR SEQ ID NO: 36:

(i) SEQUENCE CHARACTERISTICS:
        (A) LENGTH: 64 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 36:

```
TATCACCGCA AGGGATAAAT ATCTAACACC GTGCGTGTTG ACTATTTTAC CTCTGGCGGT    60

GATA                                                                 64
```

(2) INFORMATION FOR SEQ ID NO: 37:

(i) SEQUENCE CHARACTERISTICS:
        (A) LENGTH: 70 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 37:

```
CTACAAGGGA CTTTCCGCTG GGGACTTTCC AGGGAGGCGT GGCCTGGGCG GGACTGGGGA    60

GTGGCGTCCC                                                          70
```

(2) INFORMATION FOR SEQ ID NO: 38:

(i) SEQUENCE CHARACTERISTICS:
        (A) LENGTH: 37 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 38:

```
CTACAAGGGA CTTTCCGCTG GGGACTTTCC AGGGAGG                             37
```

(2) INFORMATION FOR SEQ ID NO: 39:

(i) SEQUENCE CHARACTERISTICS:
        (A) LENGTH: 22 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 39:

```
CGGGACTGGG GAGTGGCGTC CC                                             22
```

(2) INFORMATION FOR SEQ ID NO: 40:

(i) SEQUENCE CHARACTERISTICS:
        (A) LENGTH: 103 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 40:

```
CTACAAGGGA CTTTCCGCTG GGGACTTTCC AGGGAGGTAT CACCGCCAGT GGTATTTATG    60

TCAACACCGC CAGAGATAAT TTATCACCGC AGATGGTTCT GCA                     103
```

(2) INFORMATION FOR SEQ ID NO: 41:

(i) SEQUENCE CHARACTERISTICS:
        (A) LENGTH: 62 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 41:

```
GAACCATCTG CGGTGATAAA TTATCTCTGG CGGTGTTGAC ATAAATACCA CTGGCGGTGA      60

TA                                                                    62
```

(2) INFORMATION FOR SEQ ID NO: 42:

(i) SEQUENCE CHARACTERISTICS:
        (A) LENGTH: 71 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 42:

```
GATCCAACCA TCTGCGGTGA TAAATTATCT CTGGCGGTGT TGACATAAAT ACCACTGGCG      60

GTGATACTGC A                                                          71
```

(2) INFORMATION FOR SEQ ID NO: 43:

(i) SEQUENCE CHARACTERISTICS:
        (A) LENGTH: 63 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 43:

```
GTATCACCGC CAGTGGTATT TATGTCAACA CCGCCAGAGA TAATTTATCA CCGCAGATGG      60

TTG                                                                   63
```

(2) INFORMATION FOR SEQ ID NO: 44:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 44:

```
GATCCGGGGG GATACCCCCC G                                               21
```

(2) INFORMATION FOR SEQ ID NO: 45:

(i) SEQUENCE CHARACTERISTICS:
        (A) LENGTH: 91 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO -continued (xi) SEQUENCE DESCRIPTION: SEQ ID NO: 45:

CGGGACTGGG GAGTGGCGTC CCTATCACCG CAAGGGATAA ATATCTAACA CCGTGCGTGT    60

TGACTATTTT ACCTCTGGCG GTGATAGCAT G    91

(2) INFORMATION FOR SEQ ID NO: 46:

(i) SEQUENCE CHARACTERISTICS:
        (A) LENGTH: 53 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 46:

CTAAGGGCGT AACCGAAATC GGTTGAACCG AAACCGGTTA GTATAAAGC AGA    53

(2) INFORMATION FOR SEQ ID NO: 47:

(i) SEQUENCE CHARACTERISTICS:
        (A) LENGTH: 54 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 47:

AAAAGGGAGT AACCGAAAAC GGTCGGGACC GAAAACGGTG TATATAAAAG ATGT    54

(2) INFORMATION FOR SEQ ID NO: 48:

(i) SEQUENCE CHARACTERISTICS:
        (A) LENGTH: 54 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 48:

AGTAGGGTGT AACCGAAAGC GGTTCAACCG AAAACGGTGC ATATATAAAG CAAA    54

(2) INFORMATION FOR SEQ ID NO: 49:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 49:

```
GCTTCAACCG AATTCGGTTG CATG                                              24

(2) INFORMATION FOR SEQ ID NO: 50:

(i) SEQUENCE CHARACTERISTICS:
          (A) LENGTH: 24 base pairs
          (B) TYPE: nucleic acid
          (C) STRANDEDNESS: both
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 50:

TGTGCAACCG ATTTCGGTTG CCTT                                              24

(2) INFORMATION FOR SEQ ID NO: 51:

(i) SEQUENCE CHARACTERISTICS:
          (A) LENGTH: 24 base pairs
          (B) TYPE: nucleic acid
          (C) STRANDEDNESS: both
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 51:

TATGCAACCG AAATAGGTTG GGCA                                              24

(2) INFORMATION FOR SEQ ID NO: 52:

(i) SEQUENCE CHARACTERISTICS:
          (A) LENGTH: 24 base pairs
          (B) TYPE: nucleic acid
          (C) STRANDEDNESS: both
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 52:

TGCCTAACCG TTTTCGGTTA CTTG                                              24

(2) INFORMATION FOR SEQ ID NO: 53:

(i) SEQUENCE CHARACTERISTICS:
          (A) LENGTH: 24 base pairs
          (B) TYPE: nucleic acid
          (C) STRANDEDNESS: both
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 53:

GGACTAACCG TTTTAGGTCA TATT                                              24
```

(2) INFORMATION FOR SEQ ID NO: 54:

(i) SEQUENCE CHARACTERISTICS:
        (A) LENGTH: 52 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 54:

```
GACGACTATC CAGCGACCAA GATCAGAGCC AGACACCGGA AACCCCTGCC AC            52
```

(2) INFORMATION FOR SEQ ID NO: 55:

(i) SEQUENCE CHARACTERISTICS:
        (A) LENGTH: 53 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 55:

```
GACGACACGG TATCCGCTAC TCAGCTTGTT AAACAGCTAC AGCACACCCC CTC           53
```

(2) INFORMATION FOR SEQ ID NO: 56:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 56:

```
GACGACGACC TGCAGACACC ACAGACACCG CCCAGCCCCT TACAAAGCTG TTCTGTGCAG    60
```

(2) INFORMATION FOR SEQ ID NO: 57:

(i) SEQUENCE CHARACTERISTICS:
        (A) LENGTH: 68 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 57:

```
CATACCAAAG CCGTCGCCTT GGGCACCGAA GAAACACAAC CACTAAGTTG TTGCACAGAG    60
ACTCAGTG                                                             68
```

(2) INFORMATION FOR SEQ ID NO: 58:

(i) SEQUENCE CHARACTERISTICS:
            (A) LENGTH: 77 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 58:

TAATGTAATT GATTGTAATG ACTCTATGTG CAGTACCAGT ACCGTATTCC AGCACCGTGT    60

CCGTGGGCAC CGCAAAG                                                  77

(2) INFORMATION FOR SEQ ID NO: 59:

(i) SEQUENCE CHARACTERISTICS:
            (A) LENGTH: 80 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 59:

ACAGACAACG ATAACCGACC ACCACAAGCA GCGGCCAAAC ACCCCGCCTT GGACAATAGA    60

ACAGCACGTA CTGCAACTAA                                               80

(2) INFORMATION FOR SEQ ID NO: 60:

(i) SEQUENCE CHARACTERISTICS:
            (A) LENGTH: 266 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 60:

CATATGCAAT ACAATGCATT ATACAAACTG GACACATATA TATATTTGTG AAGAAGCATC    60

AGTAACTGTG GTAGAGGGTC AAGTTGACTA TTATGGTTTA TATTATGTTC ATGAAGGAAT   120

ACGAACATAT TTTGTGCAGT TTAAAGATGA TGCAGAAAAA TATAGTAAAA ATAAAGTATG   180

GGAAGTTCAT GCGGGTGGTC AGGTAATATT ATGTCCTACA TCTGTGTTTA GCAGCAACGA   240

AGTATCCTCT CCTGAAATTA TTAGGC                                       266

(2) INFORMATION FOR SEQ ID NO: 61:

(i) SEQUENCE CHARACTERISTICS:
            (A) LENGTH: 95 base pairs
            (B) TYPE: nucleic acid
            (C) STRANDEDNESS: both
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 61:

AGGATGTATA AAAAAACATG GATATACAGT GGAAGTGCAG TTTGATGGAG ACATATGCTA    60

TTAGGCAGCA CTTGGCCAAC CACCCCGCCG CGACC                              95

(2) INFORMATION FOR SEQ ID NO: 62:

(i) SEQUENCE CHARACTERISTICS:
        (A) LENGTH: 81 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 62:

CATGTTTTTT TATACATCCA TATCACCGCC AGTGGTATTT ATGTCAACAC CGCCAGAGAT    60

AATTTATCAC CGCAGATGGT T                                             81

(2) INFORMATION FOR SEQ ID NO: 63:

(i) SEQUENCE CHARACTERISTICS:
        (A) LENGTH: 322 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 63:

Met Ala Asp Asp Pro Tyr Gly Thr Gly Gln Met Phe His Leu Asn
1               5                   10                  15

Thr Ala Leu Thr His Ser Ile Phe Asn Ala Glu Leu Tyr Ser Pro Glu
                20                  25                  30

Ile Pro Leu Ser Thr Asp Gly Pro Tyr Leu Gln Ile Leu Glu Gln Pro
            35                  40                  45

Lys Gln Arg Gly Phe Arg Phe Arg Tyr Val Cys Glu Gly Pro Ser His
    50                  55                  60

Gly Gly Leu Pro Gly Ala Ser Ser Glu Lys Asn Lys Lys Ser Tyr Pro
65              70                  75                  80

Gln Val Lys Ile Cys Asn Tyr Val Gly Pro Ala Lys Val Ile Val Gln
                85                  90                  95

Leu Val Thr Asn Gly Lys Asn Ile His Leu His Ala His Ser Leu Val
                100                 105                 110

Gly Lys His Cys Glu Asp Gly Val Cys Thr Val Thr Ala Gly Pro Lys
            115                 120                 125

Asp Met Val Val Gly Phe Ala Asn Leu Gly Ile Leu His Val Thr Lys
    130                 135                 140

Lys Lys Val Phe Glu Thr Leu Glu Ala Arg Met Thr Glu Ala Cys Ile
145                 150                 155                 160

Arg Gly Tyr Asn Pro Gly Leu Leu Val His Ser Asp Leu Ala Tyr Leu
                165                 170                 175

Gln Ala Glu Gly Gly Gly Asp Arg Gln Leu Thr Asp Arg Glu Lys Glu

```
                     180                 185                 190
Ile Ile Arg Gln Ala Ala Val Gln Gln Thr Lys Glu Met Asp Leu Ser
            195                 200                 205

Val Val Arg Leu Met Phe Thr Ala Phe Leu Pro Asp Ser Thr Gly Ser
    210                 215                 220

Phe Thr Arg Arg Leu Glu Pro Val Val Ser Asp Ala Ile Tyr Asp Ser
225                 230                 235                 240

Lys Ala Pro Asn Ala Ser Asn Leu Lys Ile Val Arg Met Asp Arg Thr
                245                 250                 255

Ala Gly Cys Val Thr Gly Gly Glu Glu Ile Tyr Leu Leu Cys Asp Lys
            260                 265                 270

Val Gln Lys Asp Asp Ile Gln Ile Arg Phe Tyr Glu Glu Glu Glu Asn
    275                 280                 285

Gly Gly Val Trp Glu Gly Phe Gly Asp Phe Ser Pro Thr Asp Val His
            290                 295                 300

Arg Gln Phe Ala Ile Val Phe Lys Thr Pro Lys Tyr Lys Asp Val Asn
305                 310                 315                 320

Ile Thr (2) INFORMATION FOR SEQ ID NO: 64:

(i) SEQUENCE CHARACTERISTICS:
        (A) LENGTH: 325 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 64:

Met Ala Glu Asp Asp Pro Tyr Leu Gly Arg Pro Glu Gln Met Phe His
1               5                   10                  15

Leu Asp Pro Ser Leu Thr His Thr Ile Phe Asn Pro Glu Val Phe Gln
                20                  25                  30

Pro Gln Met Ala Leu Pro Thr Ala Asp Gly Pro Tyr Leu Gln Ile Leu
            35                  40                  45

Glu Gln Pro Lys Gln Arg Gly Phe Arg Phe Arg Tyr Val Cys Glu Gly
        50                  55                  60

Pro Ser His Gly Gly Leu Pro Gly Ala Ser Ser Glu Lys Asn Lys Lys
65                  70                  75                  80

Ser Tyr Pro Gln Val Lys Ile Cys Asn Tyr Val Gly Pro Ala Lys Val
                85                  90                  95

Ile Val Gln Leu Val Thr Asn Gly Lys Asn Ile His Leu His Ala His
                100                 105                 110

Ser Leu Val Gly Lys His Cys Glu Asp Gly Ile Cys Thr Val Thr Ala
            115                 120                 125

Gly Pro Glu Asp Cys Val His Gly Phe Ala Asn Leu Gly Ile Leu His
        130                 135                 140

Val Thr Lys Lys Lys Val Phe Glu Thr Leu Glu Ala Arg Met Thr Glu
145                 150                 155                 160

Ala Cys Ile Arg Gly Tyr Asn Pro Gly Leu Leu Val His Pro Asp Leu
                165                 170                 175

Ala Tyr Leu Gln Ala Glu Gly Gly Gly Asp Arg Gln Leu Gly Asp Arg
```

```
                       180                 185                 190
Glu Lys Glu Leu Ile Arg Gln Ala Ala Leu Gln Gln Thr Lys Glu Met
                195                 200                 205
Asp Leu Ser Val Val Arg Leu Met Phe Thr Ala Phe Leu Pro Asp Ser
        210                 215                 220
Thr Gly Ser Phe Thr Arg Arg Leu Glu Pro Val Val Ser Asp Ala Ile
225                 230                 235                 240
Tyr Asp Ser Lys Ala Pro Asn Ala Ser Asn Leu Lys Ile Val Arg Met
                245                 250                 255
Asp Arg Thr Ala Gly Cys Val Thr Gly Gly Glu Glu Ile Tyr Leu Leu
        260                 265                 270
Cys Asp Lys Val Gln Lys Asp Asp Ile Gln Ile Arg Phe Tyr Glu Glu
        275                 280                 285
Glu Glu Asn Gly Gly Val Trp Glu Gly Phe Gly Asp Phe Ser Pro Thr
        290                 295                 300
Asp Val His Arg Gln Phe Ala Ile Val Phe Lys Thr Pro Lys Tyr Lys
305                 310                 315                 320
Asp Ile Asn Ile Thr
                325

(2) INFORMATION FOR SEQ ID NO: 65:

(i) SEQUENCE CHARACTERISTICS:
        (A) LENGTH: 268 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 65:

Met Glu Pro Ala Asp Leu Leu Pro Leu Tyr Leu Gln Pro Glu Trp Gly
1               5                   10                  15
Glu Gln Glu Pro Gly Gly Ala Thr Pro Phe Val Glu Ile Leu Glu Gln
                20                  25                  30
Pro Lys Gln Arg Gly Met Arg Phe Arg Tyr Lys Cys Glu Gly Arg Ser
                35                  40                  45
Ala Gly Ser Ile Pro Gly Glu His Ser Thr Asp Ser Ala Arg Thr His
        50                  55                  60
Pro Thr Ile Arg Val Asn His Tyr Arg Gly Pro Gly Arg Val Arg Val
65                  70                  75                  80
Ser Leu Val Thr Lys Asp Pro Pro His Gly Pro His Pro His Glu Leu
                85                  90                  95
Val Gly Arg His Cys Gln His Gly Tyr Tyr Glu Ala Glu Leu Ser Pro
                100                 105                 110
Asp Arg Ser Ile His Ser Phe Gln Asn Leu Gly Ile Gln Cys Val Lys
                115                 120                 125
Lys Arg Glu Leu Glu Ala Ala Val Ala Glu Arg Ile Arg Thr Asn Asn
        130                 135                 140
Asn Pro Phe Asn Val Pro Met Glu Glu Arg Gly Ala Glu Tyr Asp Leu
145                 150                 155                 160
Ser Ala Val Arg Leu Cys Phe Gln Val Trp Val Asn Gly Pro Gly Gly
                165                 170                 175
```

```
Leu Cys Pro Leu Pro Val Leu Ser Gln Pro Ile Tyr Asp Asn Arg
            180                 185                 190

Ala Pro Ser Thr Ala Glu Leu Arg Ile Leu Pro Gly Asp Arg Asn Ser
        195                 200                 205

Gly Ser Cys Gln Gly Gly Asp Glu Ile Phe Leu Leu Cys Asp Lys Val
    210                 215                 220

Gln Lys Glu Asp Ile Glu Val Arg Phe Trp Ala Glu Gly Trp Glu Ala
225                 230                 235                 240

Lys Gly Ser Phe Ala Ala Ala Asp Val His Arg Gln Val Ala Ile Val
                245                 250                 255

Phe Arg Thr Pro Pro Phe Arg Glu Arg Ser Leu Arg
            260                 265
```

(2) INFORMATION FOR SEQ ID NO: 66:

(i) SEQUENCE CHARACTERISTICS:
        (A) LENGTH: 263 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 66:

```
Met Asp Asp Leu Phe Pro Leu Ile Phe Pro Ser Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Tyr Tyr Glu Ala Asp Leu Cys Pro Asp Arg Ser Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe His Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ala Gly Arg Pro Leu Leu Leu Thr
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240
```

```
Gln Ala Asp Val His Arg Gln Val Ala Ile Val Phe Arg Thr Pro Pro
            245                 250                 255

Tyr Ala Asp Pro Ser Leu Gln
            260

(2) INFORMATION FOR SEQ ID NO: 67:

(i) SEQUENCE CHARACTERISTICS:
        (A) LENGTH: 263 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 67:

Met Asp Glu Leu Phe Pro Leu Ile Phe Pro Ala Glu Pro Ala Gln Ala
1               5                  10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Pro His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln
            260

(2) INFORMATION FOR SEQ ID NO: 68:

(i) SEQUENCE CHARACTERISTICS:
```

(A) LENGTH: 299 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 68:

Met Phe Pro Asn Gln Asn Asn Gly Ala Ala Pro Gly Gln Gly Pro Ala
1               5                   10                  15

Val Asp Gly Gln Gln Ser Leu Asn Tyr Asn Gly Leu Pro Ala Gln Gln
            20                  25                  30

Gln Gln Gln Leu Ala Gln Ser Thr Lys Asn Val Arg Lys Lys Pro Tyr
        35                  40                  45

Val Lys Ile Thr Glu Gln Pro Ala Gly Lys Ala Leu Arg Phe Arg Tyr
    50                  55                  60

Glu Cys Glu Gly Arg Ser Ala Gly Ser Ile Pro Gly Val Asn Ser Thr
65                  70                  75                  80

Pro Glu Asn Lys Thr Tyr Pro Thr Ile Glu Ile Val Gly Tyr Lys Gly
                85                  90                  95

Arg Ala Val Val Val Ser Cys Val Thr Lys Asp Thr Pro Tyr Arg
            100                 105                 110

Pro His Pro His Asn Leu Val Gly Lys Glu Gly Cys Lys Lys Gly Val
            115                 120                 125

Cys Thr Leu Glu Ile Asn Ser Glu Thr Met Arg Ala Val Phe Ser Asn
        130                 135                 140

Leu Gly Ile Gln Cys Val Lys Lys Lys Asp Ile Glu Ala Ala Leu Lys
145                 150                 155                 160

Ala Arg Glu Glu Ile Arg Val Asp Pro Phe Lys Thr Gly Phe Ser His
                165                 170                 175

Arg Phe Gln Pro Ser Ser Ile Asp Leu Asn Ser Val Arg Leu Cys Phe
            180                 185                 190

Gln Val Phe Met Glu Ser Glu Gln Lys Gly Arg Phe Thr Ser Pro Leu
        195                 200                 205

Pro Pro Val Val Ser Glu Pro Ile Phe Asp Lys Lys Ala Met Ser Asp
210                 215                 220

Leu Val Ile Cys Arg Leu Cys Ser Cys Ser Ala Thr Val Phe Gly Asn
225                 230                 235                 240

Thr Gln Ile Ile Leu Leu Cys Glu Lys Val Ala Lys Glu Asp Ile Ser
                245                 250                 255

Val Arg Phe Phe Glu Glu Lys Asn Gly Gln Ser Val Trp Glu Ala Phe
            260                 265                 270

Gly Asp Phe Gln His Thr Asp Val His Lys Gln Thr Ala Ile Thr Phe
            275                 280                 285

Lys Thr Pro Arg Tyr His Thr Leu Asp Ile Thr
    290                 295

(2) INFORMATION FOR SEQ ID NO: 69:

(i) SEQUENCE CHARACTERISTICS:
        (A) LENGTH: 261 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 69:

Met Asp Phe Leu Thr Asn Leu Arg Phe Thr Glu Gly Ile Ser Glu Pro
1               5                  10                  15

Tyr Ile Glu Ile Phe Glu Gln Pro Arg Gln Arg Gly Thr Arg Phe Arg
            20                  25                  30

Tyr Lys Cys Glu Gly Arg Ser Ala Gly Ser Ile Pro Gly Glu His Ser
        35                  40                  45

Thr Asp Asn Asn Lys Thr Phe Pro Ser Ile Gln Ile Leu Asn Tyr Phe
    50                  55                  60

Gly Lys Val Lys Ile Arg Thr Thr Leu Val Thr Lys Asn Glu Pro Tyr
65                  70                  75                  80

Lys Pro His Pro His Asp Leu Val Gly Lys Gly Cys Arg Asp Gly Tyr
                85                  90                  95

Tyr Glu Ala Glu Phe Gly Pro Glu Arg Gln Val Leu Ser Phe Gln Asn
            100                 105                 110

Leu Gly Ile Gln Cys Val Lys Lys Lys Asp Leu Lys Glu Ser Ile Ser
        115                 120                 125

Leu Arg Ile Ser Lys Lys Asn Pro Phe Asn Val Pro Glu Glu Gln Leu
    130                 135                 140

His Asn Ile Asp Glu Tyr Asp Leu Asn Val Val Arg Leu Cys Phe Gln
145                 150                 155                 160

Ala Phe Leu Pro Asp Glu His Gly Asn Tyr Thr Leu Ala Leu Pro Pro
                165                 170                 175

Leu Ile Ser Asn Pro Ile Tyr Asp Asn Arg Ala Pro Asn Thr Ala Glu
            180                 185                 190

Leu Arg Ile Cys Arg Val Asn Lys Asn Cys Gly Ser Val Lys Gly Gly
        195                 200                 205

Asp Glu Ile Phe Leu Leu Cys Asp Lys Val Gln Lys Asp Asp Ile Glu
    210                 215                 220

Val Arg Phe Val Leu Gly Asn Trp Glu Ala Lys Gly Ser Phe Ser Gln
225                 230                 235                 240

Ala Asp Val His Arg Gln Val Ala Ile Val Phe Arg Thr Pro Pro Phe
                245                 250                 255

Leu Gly Asp Ile Thr
            260

(2) INFORMATION FOR SEQ ID NO: 70:

(i) SEQUENCE CHARACTERISTICS:
         (A) LENGTH: 262 amino acids
         (B) TYPE: amino acid
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 70:

Met Asp Phe Leu Thr Asn Leu Arg Phe Thr Glu Gly Ile Ser Glu Pro
1               5                  10                  15

```
Tyr Ile Glu Ile Phe Glu Gln Pro Arg Gln Arg Gly Met Arg Phe Arg
             20                  25                  30

Tyr Lys Cys Glu Gly Arg Ser Ala Gly Ser Ile Pro Gly Glu His Ser
             35                  40                  45

Thr Asp Asn Asn Lys Thr Phe Pro Ser Ile Gln Ile Leu Asn Tyr Phe
 50                      55                  60

Gly Lys Val Lys Ile Arg Thr Thr Leu Val Thr Lys Asn Glu Pro Tyr
 65                  70                  75                  80

Lys Pro His Pro His Asp Leu Val Gly Lys Gly Cys Arg Asp Gly Tyr
                 85                  90                  95

Tyr Glu Ala Glu Phe Gly Pro Glu Arg Gln Val Leu Ser Phe Gln Asn
                100                 105                 110

Leu Gly Ile Gln Cys Val Lys Lys Asp Leu Lys Glu Ser Ile Ser
            115                 120                 125

Leu Arg Ile Ser Lys Lys Ile Asn Pro Phe Asn Val Pro Glu Glu Gln
130                 135                 140

Leu His Asn Ile Asp Glu Tyr Asp Leu Asn Val Val Arg Leu Cys Phe
145                 150                 155                 160

Gln Ala Phe Leu Pro Asp Glu His Gly Asn Tyr Thr Leu Ala Leu Pro
                165                 170                 175

Pro Leu Ile Ser Asn Pro Ile Tyr Asp Asn Arg Ala Pro Asn Thr Ala
            180                 185                 190

Glu Leu Arg Ile Cys Arg Val Asn Lys Asn Cys Gly Ser Val Lys Gly
            195                 200                 205

Gly Asp Glu Ile Phe Leu Leu Cys Asp Lys Val Gln Lys Asp Asp Ile
210                 215                 220

Glu Val Arg Phe Val Leu Gly Asn Trp Glu Ala Lys Gly Ser Phe Ser
225                 230                 235                 240

Gln Ala Asp Val His Arg Gln Val Ala Ile Val Phe Arg Thr Pro Pro
                245                 250                 255

Phe Leu Gly Asp Ile Thr
            260

(2) INFORMATION FOR SEQ ID NO: 71:

(i) SEQUENCE CHARACTERISTICS:
        (A) LENGTH: 314 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 71:

Met Ser Asn Lys Lys Gln Ser Asn Arg Leu Thr Glu Gln His Lys Leu
 1               5                  10                  15

Ser Gln Gly Val Ile Gly Ile Phe Gly Asp Tyr Ala Lys Ala His Asp
             20                  25                  30

Leu Ala Val Gly Glu Val Ser Lys Leu Val Lys Ala Leu Ser Asn
            35                  40                  45

Glu Tyr Pro Gln Leu Ser Phe Arg Tyr Arg Asp Ser Ile Lys Lys Thr
 50                  55                  60

Glu Ile Asn Glu Ala Leu Lys Lys Ile Asp Pro Asp Leu Gly Gly Thr
```

```
            65                  70                  75                  80
Leu Phe Val Ser Asn Ser Ser Ile Lys Pro Asp Gly Gly Ile Val Glu
                        85                  90                  95
Val Lys Asp Asp Tyr Gly Glu Trp Arg Val Val Leu Val Ala Glu Ala
                100                 105                 110
Lys His Gln Gly Lys Asp Ile Ile Asn Ile Arg Asn Gly Leu Leu Val
                115                 120                 125
Gly Lys Arg Gly Asp Gln Asp Leu Met Ala Ala Gly Asn Ala Ile Glu
            130                 135                 140
Arg Ser His Asn Ile Ser Glu Ile Ala Asn Phe Met Leu Ser Glu Ser
145                 150                 155                 160
His Phe Pro Tyr Val Leu Phe Leu Glu Gly Ser Asn Phe Leu Thr Glu
                        165                 170                 175
Asn Ile Ser Ile Thr Arg Pro Asp Gly Arg Val Val Asn Leu Glu Tyr
                180                 185                 190
Asn Ser Gly Ser Glu Ser His Phe Pro Tyr Val Leu Phe Leu Glu Gly
            195                 200                 205
Ser Asn Phe Leu Thr Glu Asn Ile Ser Ile Thr Arg Pro Asp Gly Arg
    210                 215                 220
Val Val Asn Leu Glu Tyr Asn Ser Gly Ile Leu Asn Arg Leu Asp Arg
225                 230                 235                 240
Leu Thr Ala Ala Asn Tyr Gly Met Pro Ile Asn Ser Asn Leu Cys Ile
                        245                 250                 255
Asn Lys Phe Val Asn His Lys Asp Lys Ser Ile Met Leu Gln Ala Ala
                260                 265                 270
Ser Ile Tyr Thr Gln Gly Asp Gly Arg Glu Trp Asp Ser Lys Ile Met
            275                 280                 285
Phe Glu Ile Met Phe Asp Ile Ser Thr Thr Ser Leu Arg Val Leu Gly
        290                 295                 300
Arg Asp Leu Phe Glu Gln Leu Thr Ser Lys
305                 310

(2) INFORMATION FOR SEQ ID NO: 72:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 72:

Cys Asp Thr Asp Asp Arg His Arg Ile Glu Glu Lys Arg Lys Arg Lys
1               5                   10                  15
Thr (2) INFORMATION FOR SEQ ID NO: 73:

(i) SEQUENCE CHARACTERISTICS:
        (A) LENGTH: 168 amino acids
        (B) TYPE: amino acid
        (D) TOPOLOGY: linear (ii) MOLECULE TYPE: peptide
```

(iii) HYPOTHETICAL: NO (iv) ANTI-SENSE: NO (v) FRAGMENT TYPE: internal (xi) SEQUENCE DESCRIPTION: SEQ ID NO: 73:

```
Gly Asp Pro Gly Lys Lys Gln His Ile Cys His Ile Gln Gly Cys
1               5                   10                  15

Gly Lys Val Tyr Gly Lys Thr Ser His Leu Arg Ala His Leu Arg Trp
            20                  25                  30

His Thr Gly Glu Arg Pro Phe Met Cys Thr Trp Ser Tyr Cys Gly Lys
            35                  40                  45

Arg Phe Thr Arg Ser Asp Glu Leu Gln Arg His Lys Arg Thr His Thr
        50                  55                  60

Gly Glu Lys Lys Phe Ala Cys Pro Glu Cys Pro Lys Arg Phe Met Arg
65                  70                  75                  80

Ser Asp His Leu Ser Lys His Ile Lys Thr His Gln Asn Lys Lys Gly
                85                  90                  95

Gly Pro Gly Val Ala Leu Ser Val Gly Thr Leu Pro Leu Asp Ser Gly
            100                 105                 110

Ala Gly Ser Glu Gly Ser Gly Thr Ala Thr Pro Ser Ala Leu Ile Thr
            115                 120                 125

Thr Asn Met Val Ala Met Glu Ala Ile Cys Pro Glu Gly Ile Ala Arg
130                 135                 140

Leu Ala Asn Ser Gly Ile Asn Val Met Gln Val Ala Asp Leu Gln Ser
145                 150                 155                 160

Ile Asn Ile Ser Gly Asn Gly Phe
                165
```

(2) INFORMATION FOR SEQ ID NO: 74:

(i) SEQUENCE CHARACTERISTICS:
    (A) LENGTH: 181 amino acids
    (B) TYPE: amino acid
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 74:

```
Ser Gly Ile Val Pro Gln Leu Gln Asn Ile Val Ser Thr Val Asn Leu
1               5                   10                  15

Gly Cys Lys Leu Asp Leu Lys Thr Ile Ala Leu Arg Ala Arg Asn Ala
            20                  25                  30

Glu Tyr Asn Pro Lys Arg Phe Ala Ala Val Ile Met Arg Ile Arg Glu
            35                  40                  45

Pro Arg Thr Thr Ala Leu Ile Phe Ser Ser Gly Lys Met Val Cys Thr
        50                  55                  60

Gly Ala Lys Ser Glu Glu Gln Ser Arg Leu Ala Ala Arg Lys Tyr Ala
65                  70                  75                  80

Arg Val Val Gln Lys Leu Gly Phe Pro Ala Lys Phe Leu Asp Phe Lys
                85                  90                  95

Ile Gln Asn Met Val Gly Ser Cys Asp Val Lys Phe Pro Ile Arg Leu
            100                 105                 110
```

```
Glu Gly Leu Val Leu Thr His Gln Gln Phe Ser Ser Tyr Glu Pro Glu
            115                 120                 125
Leu Phe Pro Gly Leu Ile Tyr Arg Met Ile Lys Pro Arg Ile Val Leu
130                 135                 140
Leu Ile Phe Val Ser Gly Lys Val Val Leu Thr Gly Ala Lys Val Arg
145                 150                 155                 160
Ala Glu Ile Tyr Glu Ala Phe Glu Asn Ile Tyr Pro Ile Leu Lys Gly
                165                 170                 175
Phe Arg Lys Thr Thr
                180

(2) INFORMATION FOR SEQ ID NO: 75:

(i) SEQUENCE CHARACTERISTICS:
          (A) LENGTH: 85 amino acids
          (B) TYPE: amino acid
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 75:

Ser Cys Phe Ala Leu Ile Ser Gly Thr Ala Asn Gln Val Lys Cys Tyr
1               5                   10                  15
Arg Phe Arg Val Lys Lys Asn His Arg His Arg Tyr Glu Asn Cys Thr
                20                  25                  30
Thr Thr Trp Phe Thr Val Ala Asp Asn Gly Ala Glu Arg Gln Gly Gln
            35                  40                  45
Ala Gln Ile Leu Ile Thr Phe Gly Ser Pro Ser Gln Arg Gln Asp Phe
        50                  55                  60
Leu Lys His Val Pro Leu Pro Pro Gly Met Asn Ile Ser Gly Phe Thr
65                  70                  75                  80
Ala Ser Leu Asp Phe
                85

(2) INFORMATION FOR SEQ ID NO: 76:

(i) SEQUENCE CHARACTERISTICS:
          (A) LENGTH: 87 amino acids
          (B) TYPE: amino acid
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 76:

Cys Pro Cys Leu Leu Ile Gly Thr Ser Gly Asn Gly Asn Gln Val Lys
1               5                   10                  15
Cys Tyr Ser Phe Arg Val Lys Arg Trp His Asp Arg Asp Lys Tyr His
                20                  25                  30
His Thr Thr Thr Trp Trp Ala Val Gly Gly Gln Gly Ser Glu Arg Pro
            35                  40                  45
Gly Asp Ala Thr Val Ile Val Thr Phe Lys Asp Gln Ser Gln Arg Ser
        50                  55                  60
```

His Phe Leu Gln Gln Val Pro Leu Pro Pro Gly Met Ser Ala His Gly
65                  70                  75                  80

Val Thr Met Thr Val Asp Phe
                85

(2) INFORMATION FOR SEQ ID NO: 77:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 77:

Pro Pro Val Ile Cys Leu Lys Gly Gly His Asn Gln Leu Lys Cys Leu
1               5                   10                  15

Arg Tyr Arg Leu Lys Ser Lys His Ser Ser Leu Phe Asp Cys Ile Ser
                20                  25                  30

Thr Thr Trp Ser Trp Val Asp Thr Thr Ser Thr Cys Arg Leu Gly Ser
            35                  40                  45

Gly Arg Met Leu Ile Lys Phe Ala Asp Ser Glu Gln Arg Asp Lys Phe
        50                  55                  60

Leu Ser Arg Val Pro Leu Pro Ser Thr Thr Gln Val Phe Leu Gly Asn
65                  70                  75                  80

Phe Tyr Gly Leu (2) INFORMATION FOR SEQ ID NO: 78:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 78:

Pro Pro Val Ile Leu Val Arg Gly Gly Ala Asn Thr Leu Lys Cys Phe
1               5                   10                  15

Arg Asn Arg Ala Arg Val Arg Tyr Arg Gly Leu Phe Lys Tyr Phe Ser
                20                  25                  30

Thr Thr Trp Ser Trp Val Ala Gly Asp Ser Thr Glu Arg Leu Gly Arg
            35                  40                  45

Ser Arg Met Leu Ile Leu Phe Thr Ser Ala Cys Gln Arg Glu Lys Pro
        50                  55                  60

Asp Glu Thr Val Lys Tyr Pro Lys Gly Val Asp Thr Ser Tyr Gly Asn
65                  70                  75                  80

Leu Asp Ser Leu (2) INFORMATION FOR SEQ ID NO: 79:

(i) SEQUENCE CHARACTERISTICS:
            (A) LENGTH: 84 amino acids
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 79:

Pro Pro Val Val Cys Val Lys Gly Gly Ala Asn Gln Leu Lys Cys Leu
1               5                   10                  15

Arg Tyr Arg Leu Lys Ala Ser Thr Gln Val Asp Phe Asp Ser Ile Ser
            20                  25                  30

Thr Thr Trp His Trp Thr Asp Arg Lys Asn Thr Glu Arg Ile Gly Ser
            35                  40                  45

Ala Arg Met Leu Val Lys Phe Ile Asp Glu Ala Gln Arg Glu Lys Phe
        50                  55                  60

Leu Glu Arg Val Ala Leu Pro Arg Ser Val Ser Val Phe Leu Gly Gln
65                  70                  75                  80

Phe Asn Gly Ser (2) INFORMATION FOR SEQ ID NO: 80:

(i) SEQUENCE CHARACTERISTICS:
            (A) LENGTH: 84 amino acids
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 80:

Thr Pro Ile Val Gln Leu Gln Gly Asp Ser Asn Cys Leu Lys Cys Phe
1               5                   10                  15

Arg Tyr Arg Leu Asn Asp Lys Tyr Lys His Leu Phe Glu Leu Ala Ser
            20                  25                  30

Ser Thr Trp His Trp Ala Ser Pro Glu Ala Pro His Lys Asn Ala Ile
            35                  40                  45

Val Thr Leu Thr Tyr Ser Ser Glu Gly Gln Arg Gln Gln Phe Leu Asn
        50                  55                  60

Ser Val Lys Ile Pro Pro Thr Ile Arg His Lys Val Gly Phe Met Ser
65                  70                  75                  80

Leu His Leu Leu (2) INFORMATION FOR SEQ ID NO: 81:

(i) SEQUENCE CHARACTERISTICS:
            (A) LENGTH: 84 amino acids
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 81:

Thr Pro Ile Val Gln Phe Gln Gly Glu Ser Asn Cys Leu Lys Cys Phe
1               5                   10                  15

Arg Tyr Arg Leu Asn Arg Asp His Arg His Leu Phe Asp Leu Ile Ser
            20                  25                  30

Ser Thr Trp His Trp Ala Ser Ser Lys Ala Pro His Lys His Ala Ile
        35                  40                  45

Val Thr Val Thr Tyr Asp Ser Glu Glu Gln Arg Gln Gln Phe Leu Asp
    50                  55                  60

Val Val Lys Ile Pro Pro Thr Ile Ser His Lys Leu Gly Phe Met Ser
65              70                  75                  80

Leu His Leu Leu (2) INFORMATION FOR SEQ ID NO: 82:

(i) SEQUENCE CHARACTERISTICS:
        (A) LENGTH: 80 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 82:

Thr Pro Ile Ile His Leu Lys Gly Asp Arg Asn Ser Leu Lys Cys Leu
1               5                   10                  15

Arg Tyr Arg Leu Arg Lys His Ser Asp His Tyr Arg Asp Ile Ser Ser
            20                  25                  30

Thr Trp His Trp Thr Gly Ala Gly Asn Glu Lys Thr Gly Ile Leu Thr
        35                  40                  45

Val Thr Tyr His Ser Glu Thr Gln Arg Thr Lys Phe Leu Asn Thr Val
    50                  55                  60

Ala Ile Pro Asp Ser Val Gln Ile Leu Val Gly Tyr Asn Thr Met Tyr
65              70                  75                  80

(2) INFORMATION FOR SEQ ID NO: 83:

(i) SEQUENCE CHARACTERISTICS:
        (A) LENGTH: 80 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 83:

Thr Pro Ile Val His Leu Lys Gly Asp Ala Asn Thr Leu Lys Cys Leu
1               5                   10                  15

Arg Tyr Arg Phe Lys Lys His Cys Thr Leu Tyr Thr Ala Val Ser Ser
            20                  25                  30

Thr Trp His Trp Thr Gly His Asn Tyr Lys His Lys Ser Ala Ile Val

```
                35                  40                  45
Thr Leu Thr Tyr Asp Ser Glu Trp Gln Arg Asp Gln Phe Leu Ser Gln
 50                  55                  60

Val Lys Ile Pro Lys Thr Ile Thr Val Ser Thr Gly Phe Met Ser Ile
 65                  70                  75                  80
```

(2) INFORMATION FOR SEQ ID NO: 84:

(i) SEQUENCE CHARACTERISTICS:
        (A) LENGTH: 81 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 84:

```
Ala Pro Ile Val His Leu Lys Gly Glu Ser Asn Ser Leu Lys Cys Leu
 1               5                  10                  15

Arg Tyr Arg Leu Lys Pro Tyr Asn Glu Leu Tyr Ser Ser Met Ser Ser
                20                  25                  30

Thr Trp His Trp Thr Ser Asp Asn Lys Asn Ser Lys Asn Gly Ile Val
                35                  40                  45

Thr Val Thr Phe Val Thr Gly Gln Gln Gln Met Phe Leu Gly Thr
 50                  55                  60

Val Lys Ile Pro Pro Thr Val Gln Ile Ser Thr Gly Phe Met Thr Leu
 65                  70                  75                  80

Val
```

(2) INFORMATION FOR SEQ ID NO: 85:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 85:

```
Gly Ile Val Glu Gln Cys Cys Thr Ser Ile Cys Ser Leu Tyr Gln Leu
 1               5                  10                  15

Glu Asn Tyr Cys Asn
                20
```

(2) INFORMATION FOR SEQ ID NO: 86:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 86:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

(2) INFORMATION FOR SEQ ID NO: 87:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 87:

Gly Ile Val Glu Gln Cys Cys Ala Ser Val Cys Ser Leu Tyr Gln Leu
1               5                   10                  15

Glu Asn Tyr Cys Asn
            20

(2) INFORMATION FOR SEQ ID NO: 88:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 88:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

(2) INFORMATION FOR SEQ ID NO: 89:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 89:

Gln Leu Tyr Ser Ala Leu Ala Asn Lys Cys Cys His Val Gly Cys Ile
1               5                   10                  15

```
Lys Arg Ser Leu Ala Arg Phe Cys
            20
```

(2) INFORMATION FOR SEQ ID NO: 90:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 90:

```
Asp Ser Trp Met Glu Glu Val Ile Lys Ile Cys Gly Arg Glu Leu Val
1               5                   10                  15

Arg Ala Gln Ile Ala Ile Cys Gly Met Ser Thr Trp Ser Lys Arg Ser
            20                  25                  30

Leu
```

(2) INFORMATION FOR SEQ ID NO: 91:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 91:

```
Glu Glu Lys Met Gly Thr Ala Lys Lys Cys Cys Ala Ile Gly Cys Ser
1               5                   10                  15

Thr Glu Asp Phe Arg Met Val Cys
            20
```

(2) INFORMATION FOR SEQ ID NO: 92:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 92:

```
Arg Pro Asn Trp Glu Glu Arg Ser Arg Leu Cys Gly Arg Asp Leu Ile
1               5                   10                  15

Arg Ala Phe Ile Tyr Leu Cys Gly Gly Thr Arg Trp Thr Arg Leu Pro
            20                  25                  30

Asn Phe Gly Asn Tyr Pro Ile Met
            35                  40
```

(2) INFORMATION FOR SEQ ID NO: 93:

(i) SEQUENCE CHARACTERISTICS:
        (A) LENGTH: 182 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 93:

```
Ser Gly Ile Val Pro Thr Leu Gln Asn Ile Val Ser Thr Val Asn Leu
1               5                   10                  15

Asp Cys Lys Leu Asp Leu Lys Ala Ile Ala Leu Gln Ala Arg Asn Ala
                20                  25                  30

Glu Tyr Asn Pro Lys Arg Phe Ala Ala Val Ile Met Arg Ile Arg Glu
            35                  40                  45

Pro Lys Thr Thr Ala Leu Ile Phe Ala Ser Gly Lys Met Val Cys Thr
50                  55                  60

Gly Ala Lys Ser Glu Asp Phe Ser Lys Met Ala Ala Arg Lys Tyr Ala
65                  70                  75                  80

Arg Ile Val Gln Lys Leu Gly Phe Pro Ala Lys Phe Lys Asp Phe Lys
                85                  90                  95

Ile Gln Asn Ile Val Gly Ser Cys Asp Val Lys Phe Pro Ile Arg Leu
            100                 105                 110

Glu Gly Leu Ala Tyr Ser His Ala Ala Phe Ser Ser Tyr Glu Pro Glu
        115                 120                 125

Leu Phe Pro Gly Leu Ile Tyr Arg Met Lys Val Pro Lys Ile Val Leu
130                 135                 140

Leu Ile Phe Val Ser Gly Lys Ile Val Ile Thr Gly Ala Lys Met Arg
145                 150                 155                 160

Asp Glu Thr Tyr Lys Ala Phe Glu Asn Ile Tyr Pro Val Leu Ser Glu
                165                 170                 175

Phe Arg Lys Ile Gln Gln
            180
```

(2) INFORMATION FOR SEQ ID NO: 94:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 94:

```
Asn Ser Asn Ser Thr Pro Ile Val His Leu Lys Gly Asp Ala Asn Thr
1               5                   10                  15

Leu Lys Cys Leu Arg Tyr Arg Phe Lys Lys His Cys Thr Leu Tyr Thr
                20                  25                  30

Ala Val Ser Ser Thr Trp His Trp Thr Gly His Asn Val Lys His Lys
            35                  40                  45
```

Ser Ala Ile Val Thr Leu Thr Tyr Asp Ser Glu Trp Gln Arg Asp Gln
    50                  55                  60

Phe Leu Ser Gln Val Lys Ile Pro Lys Thr Ile Thr Val Ser Thr Gly
65                  70                  75                  80

Phe Met Ser Ile (2) INFORMATION FOR SEQ ID NO: 95:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 95:

Asn Ser Asn Thr Thr Pro Ile Val His Leu Lys Gly Asp Ala Asn Thr
1               5                   10                  15

Leu Lys Cys Leu Arg Tyr Arg Phe Lys Lys His Cys Thr Leu Tyr Thr
                20                  25                  30

Ala Val Ser Ser Thr Trp His Trp Thr Gly His Asn Val Lys His Lys
            35                  40                  45

Ser Ala Ile Val Thr Leu Thr Tyr Asp Ser Glu Trp Gln Arg Asp Gln
    50                  55                  60

Phe Leu Ser Gln Val Lys Ile Pro Lys Thr Ile Thr Val Ser Thr Gly
65                  70                  75                  80

Phe Met Ser Ile (2) INFORMATION FOR SEQ ID NO: 96:

(i) SEQUENCE CHARACTERISTICS:
        (A) LENGTH: 83 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 96:

Ser Gly Asn Thr Thr Pro Ile Ile His Leu Lys Gly Asp Arg Asn Ser
1               5                   10                  15

Leu Lys Cys Leu Arg Tyr Arg Leu Arg Lys His Ser Asp His Tyr Arg
                20                  25                  30

Asp Ile Ser Ser Thr Trp His Trp Thr Gly Ala Gly Asn Glu Lys Thr
            35                  40                  45

Gly Ile Leu Thr Val Thr Tyr His Ser Glu Thr Gln Arg Thr Lys Phe
    50                  55                  60

Leu Asn Thr Val Ala Ile Pro Asp Ser Val Gln Ile Leu Val Gly Tyr
65                  70                  75                  80

Met Thr Met (2) INFORMATION FOR SEQ ID NO: 97:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 97:

```
Ser Gly Asn Thr Ala Pro Ile Val His Leu Lys Gly Glu Ser Asn Ser
1               5                   10                  15

Leu Lys Cys Leu Arg Tyr Arg Leu Lys Pro Tyr Lys Glu Leu Tyr Ser
                20                  25                  30

Ser Met Ser Ser Thr Trp His Trp Thr Ser Asp Asn Lys Asn Ser Lys
            35                  40                  45

Asn Gly Ile Val Thr Val Thr Phe Val Thr Glu Gln Gln Gln Gln Met
        50                  55                  60

Phe Leu Gly Thr Val Lys Ile Pro Pro Thr Val Gln Ile Ser Thr Gly
65                  70                  75                  80

Phe Met Thr Leu
```

(2) INFORMATION FOR SEQ ID NO: 98:

(i) SEQUENCE CHARACTERISTICS:
        (A) LENGTH: 89 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 98:

```
Ser Gly Asn Thr Ser Cys Phe Ala Leu Ile Ser Gly Thr Ala Asn Gln
1               5                   10                  15

Val Lys Cys Tyr Arg Phe Arg Val Lys Lys Asn His Arg His Arg Tyr
                20                  25                  30

Glu Asn Cys Thr Thr Thr Trp Phe Thr Val Ala Asp Asn Gly Ala Glu
            35                  40                  45

Arg Gln Gly Gln Ala Gln Ile Leu Ile Thr Phe Gly Ser Pro Ser Gln
        50                  55                  60

Arg Gln Asp Phe Leu Lys His Val Pro Leu Pro Pro Gly Met Asn Ile
65                  70                  75                  80

Ser Gly Phe Thr Ala Ser Leu Asp Phe
                85
```

(2) INFORMATION FOR SEQ ID NO: 99:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 99:

Ser Asn Lys Lys Thr Thr Ala
1               5

(2) INFORMATION FOR SEQ ID NO: 100:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 100:

Asn Ser Asn Thr
1

(2) INFORMATION FOR SEQ ID NO: 101:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 101:

Ser Gly Asn Thr
1

(2) INFORMATION FOR SEQ ID NO: 102:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 102:

Ser Ser Gly Ser Ser Gly
1               5

(2) INFORMATION FOR SEQ ID NO: 103:

(i) SEQUENCE CHARACTERISTICS:
            (A) LENGTH: 15 amino acids
            (B) TYPE: amino acid (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 103:

Cys Tyr Pro Glu Ile Lys Asp Lys Glu Glu Val Gln Arg Lys Arg
1               5                   10                  15

(2) INFORMATION FOR SEQ ID NO: 104:

(i) SEQUENCE CHARACTERISTICS:
            (A) LENGTH: 66 amino acids
            (B) TYPE: amino acid
            (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 104:

Met Glu Gln Arg Ile Thr Leu Lys Asp Tyr Ala Met Arg Phe Gly Gln
1               5                   10                  15

Thr Lys Thr Ala Lys Asp Leu Gly Val Tyr Gln Ser Ala Ile Asn Lys
                20                  25                  30

Ala Ile His Ala Gly Arg Lys Ile Phe Leu Thr Ile Asn Ala Asp Gly
            35                  40                  45

Ser Val Tyr Ala Glu Glu Val Lys Pro Phe Pro Ser Asn Lys Lys Thr
        50                  55                  60

Thr Ala
65

(2) INFORMATION FOR SEQ ID NO: 105:

(i) SEQUENCE CHARACTERISTICS:
            (A) LENGTH: 66 amino acids
            (B) TYPE: amino acid
            (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 105:

Met Glu Gln Glu Ile Thr Leu Lys Asp Tyr Ala Met Arg Phe Gly Gln
1               5                   10                  15

Thr Lys Thr Ala Lys Asp Leu Gly Val Tyr Gln Ser Ala Ile Asn Lys
                20                  25                  30

Ala Ile His Ala Gly Arg Lys Ile Phe Leu Thr Ile Asn Ala Asp Gly
            35                  40                  45

Ser Val Tyr Ala Glu Glu Val Lys Pro Phe Pro Ser Asn Lys Lys Thr
        50                  55                  60

Thr Ala
65

(2) INFORMATION FOR SEQ ID NO: 106:

(i) SEQUENCE CHARACTERISTICS:
        (A) LENGTH: 66 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 106:

```
Met Arg Gln Arg Ile Thr Leu Lys Asp Tyr Ala Met Arg Phe Gly Gln
 1               5                  10                  15

Thr Lys Thr Ala Lys Asp Leu Gly Val Tyr Gln Ser Ala Ile Asn Lys
            20                  25                  30

Ala Ile His Ala Gly Arg Lys Ile Phe Leu Thr Ile Asn Ala Asp Gly
        35                  40                  45

Ser Val Tyr Ala Glu Glu Val Lys Pro Phe Pro Ser Asn Lys Lys Thr
    50                  55                  60

Thr Ala
65
```

(2) INFORMATION FOR SEQ ID NO: 107:

(i) SEQUENCE CHARACTERISTICS:
        (A) LENGTH: 96 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 107:

```
Ser Thr Lys Lys Lys Pro Leu Thr Gln Glu Gln Leu Glu Asp Ala Arg
 1               5                  10                  15

Arg Leu Lys Ala Ile Tyr Glu Lys Lys Lys Asn Glu Leu Gly Leu Ser
            20                  25                  30

Gln Glu Ser Val Ala Asp Lys Met Gly Met Gly Gln Ser Gly Val Gly
        35                  40                  45

Ala Leu Phe Asn Gly Ile Asn Ala Leu Asn Ala Tyr Asn Ala Ala Leu
    50                  55                  60

Leu Ala Lys Ile Leu Lys Val Ser Val Glu Glu Phe Ser Pro Ser Ile
65                  70                  75                  80

Ala Arg Glu Ile Tyr Glu Met Tyr Glu Ala Val Ser Met Glu Pro Ser
                85                  90                  95
```

(2) INFORMATION FOR SEQ ID NO: 108:

(i) SEQUENCE CHARACTERISTICS:
        (A) LENGTH: 96 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 108:

```
Ser Thr Lys Lys Lys Pro Leu Thr Gln Glu Gln Leu Glu Asp Ala Arg
1               5                   10                  15

Arg Leu Lys Ala Ile Tyr Glu Lys Lys Asn Glu Leu Gly Leu Ser
            20                  25                  30

Gln Glu Ser Val Ala Asp Lys Met Gly Met Gly Gln Ser Gly Val Gly
            35                  40                  45

Ala Leu Phe Asn Gly Ile Asn Ala Leu Asn Ala Tyr Asn Ala Ala Leu
        50                  55                  60

Leu Ala Lys Ile Leu Lys Val Ser Val Glu Glu Phe Ser Pro Ser Ile
65                  70                  75                  80

Ala Arg Glu Ile Tyr Glu Met Cys Glu Ala Val Ser Met Glu Pro Ser
                85                  90                  95
```

(2) INFORMATION FOR SEQ ID NO: 109:

(i) SEQUENCE CHARACTERISTICS:
        (A) LENGTH: 180 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 109:

```
Gly Ile Val Glu Gln Cys Cys Thr Ser Ile Cys Ser Leu Tyr Gln Leu
1               5                   10                  15

Glu Asn Tyr Cys Asn Met Ser Met Glu Gln Arg Ile Thr Leu Lys Asp
            20                  25                  30

Tyr Ala Met Arg Phe Gly Gln Thr Lys Thr Ala Lys Asp Leu Gly Val
            35                  40                  45

Tyr Gln Ser Ala Ile Asn Lys Ala Ile His Ala Gly Arg Lys Ile Phe
        50                  55                  60

Leu Thr Ile Asn Ala Asp Gly Ser Val Tyr Ala Glu Glu Val Lys Pro
65                  70                  75                  80

Phe Pro Ser Asn Lys Lys Thr Thr Ala Ser Asn Lys Lys Thr Thr Ala
                85                  90                  95

Asn Ser Asn Thr Thr Pro Ile Val His Leu Lys Gly Asp Ala Asn Thr
            100                 105                 110

Leu Lys Cys Leu Arg Tyr Arg Phe Lys Lys His Cys Thr Leu Tyr Thr
            115                 120                 125

Ala Val Ser Ser Thr Trp His Trp Thr Gly His Asn Val Lys His Lys
        130                 135                 140

Ser Ala Ile Val Thr Leu Thr Tyr Asp Ser Glu Trp Gln Arg Asp Gln
145                 150                 155                 160

Phe Leu Ser Gln Val Lys Ile Pro Lys Thr Ile Val Ser Thr Gly
                165                 170                 175

Phe Met Ser Ile
            180
```

-continued (2) INFORMATION FOR SEQ ID NO: 110:

(i) SEQUENCE CHARACTERISTICS:
        (A) LENGTH: 113 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 110:

```
Gly Ile Val Glu Gln Cys Cys Thr Ser Ile Cys Ser Leu Tyr Gln Leu
1               5                   10                  15

Glu Asn Tyr Cys Asn Met Ser Met Glu Gln Arg Ile Thr Leu Lys Asp
            20                  25                  30

Tyr Ala Met Arg Phe Gly Gln Thr Lys Thr Ala Lys Asp Leu Gly Val
        35                  40                  45

Tyr Gln Ser Ala Ile Asn Lys Ala Ile His Ala Gly Arg Lys Ile Phe
    50                  55                  60

Leu Thr Ile Asn Ala Asp Gly Ser Val Tyr Ala Glu Glu Val Lys Pro
65                  70                  75                  80

Phe Pro Ser Asn Lys Lys Thr Thr Ala Ser Asn Lys Lys Thr Thr Ala
                85                  90                  95

Cys Asp Thr Asp Asp Arg His Arg Ile Glu Lys Arg Lys Arg Lys
                100                 105                 110

Thr
```

(2) INFORMATION FOR SEQ ID NO: 111:

(i) SEQUENCE CHARACTERISTICS:
        (A) LENGTH: 292 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 111:

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Met Ser
            20                  25                  30

Met Glu Gln Glu Ile Thr Leu Lys Asp Tyr Ala Met Arg Phe Gly Gln
        35                  40                  45

Thr Lys Thr Ala Lys Asp Leu Gly Val Tyr Gln Ser Ala Ile Asn Lys
    50                  55                  60

Ala Ile His Ala Gly Arg Lys Ile Phe Leu Thr Ile Asn Ala Asp Gly
65                  70                  75                  80

Ser Val Tyr Ala Glu Glu Val Lys Pro Phe Pro Ser Asn Lys Lys Thr
                85                  90                  95

Thr Ala Ser Asn Lys Lys Thr Thr Ala Ser Ser Gly Ser Ser Gly Ser
                100                 105                 110
```

```
Gly Ile Val Pro Gln Leu Gln Asn Ile Val Ser Thr Val Asn Leu Gly
            115                 120                 125

Cys Lys Leu Asp Leu Lys Thr Ile Ala Leu Arg Ala Arg Asn Ala Glu
    130                 135                 140

Tyr Asn Pro Lys Arg Phe Ala Ala Val Ile Met Arg Ile Arg Glu Pro
145                 150                 155                 160

Arg Thr Thr Ala Leu Ile Phe Ser Ser Gly Lys Met Val Cys Thr Gly
                165                 170                 175

Ala Lys Ser Glu Glu Gln Ser Arg Leu Ala Ala Arg Lys Tyr Ala Arg
            180                 185                 190

Val Val Gln Lys Leu Gly Phe Pro Ala Lys Phe Leu Asp Phe Lys Ile
            195                 200                 205

Gln Asn Met Val Gly Ser Cys Asp Val Lys Phe Pro Ile Arg Leu Glu
    210                 215                 220

Gly Leu Val Leu Thr His Gln Gln Phe Ser Ser Tyr Glu Pro Glu Leu
225                 230                 235                 240

Phe Pro Gly Leu Ile Tyr Arg Met Ile Lys Pro Arg Ile Val Leu Leu
                245                 250                 255

Ile Phe Val Ser Gly Lys Val Val Leu Thr Gly Ala Lys Val Arg Ala
            260                 265                 270

Glu Ile Tyr Glu Ala Phe Glu Asn Ile Tyr Pro Ile Leu Lys Gly Phe
            275                 280                 285

Arg Lys Thr Thr
290

(2) INFORMATION FOR SEQ ID NO: 112:

(i) SEQUENCE CHARACTERISTICS:
        (A) LENGTH: 273 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 112:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Met Ser
            20                  25                  30

Met Arg Gln Arg Ile Thr Leu Lys Asp Tyr Ala Met Arg Phe Gly Gln
            35                  40                  45

Thr Lys Thr Ala Lys Asp Leu Gly Val Tyr Gln Ser Ala Ile Asn Lys
    50                  55                  60

Ala Ile His Ala Gly Arg Lys Ile Phe Leu Thr Ile Asn Ala Asp Gly
65                  70                  75                  80

Ser Val Tyr Ala Glu Glu Val Lys Pro Phe Pro Ser Asn Lys Lys Thr
                85                  90                  95

Thr Ala Ser Asn Lys Lys Thr Thr Ala Gly Asp Pro Gly Lys Lys Lys
            100                 105                 110

Gln His Ile Cys His Ile Gln Gly Cys Gly Lys Val Tyr Gly Lys Thr
            115                 120                 125

Ser His Leu Arg Ala His Leu Arg Trp His Thr Gly Glu Arg Pro Phe
    130                 135                 140
```

```
Met Cys Thr Trp Ser Tyr Cys Gly Lys Arg Phe Thr Arg Ser Asp Glu
145                 150                 155                 160

Leu Gln Arg His Lys Arg Thr His Thr Gly Glu Lys Lys Phe Ala Cys
                165                 170                 175

Pro Glu Cys Pro Lys Arg Phe Met Arg Ser Asp His Leu Ser Lys His
            180                 185                 190

Ile Lys Thr His Gln Asn Lys Lys Gly Gly Pro Gly Val Ala Leu Ser
            195                 200                 205

Val Gly Thr Leu Pro Leu Asp Ser Gly Ala Gly Ser Glu Gly Ser Gly
        210                 215                 220

Thr Ala Thr Pro Ser Ala Leu Ile Thr Thr Asn Met Val Ala Met Glu
225                 230                 235                 240

Ala Ile Cys Pro Glu Gly Ile Ala Arg Leu Ala Asn Ser Gly Ile Asn
                245                 250                 255

Val Met Gln Val Ala Asp Leu Gln Ser Ile Asn Ile Ser Gly Asn Gly
            260                 265                 270

Phe
```

(2) INFORMATION FOR SEQ ID NO: 113:

(i) SEQUENCE CHARACTERISTICS:
        (A) LENGTH: 421 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 113:

```
Gln Leu Tyr Ser Ala Leu Ala Asn Lys Cys Cys His Val Gly Cys Ile
1               5                   10                  15

Lys Arg Ser Leu Ala Arg Phe Cys Met Ser Met Arg Gln Arg Ile Thr
            20                  25                  30

Leu Lys Asp Tyr Ala Met Arg Phe Gly Gln Thr Lys Thr Ala Lys Asp
            35                  40                  45

Leu Gly Val Tyr Gln Ser Ala Ile Asn Lys Ala Ile His Ala Gly Arg
        50                  55                  60

Lys Ile Phe Leu Thr Ile Asn Ala Asp Gly Ser Val Tyr Ala Glu Glu
65                  70                  75                  80

Val Lys Pro Phe Pro Ser Asn Lys Lys Thr Thr Ala Ser Asn Lys Lys
                85                  90                  95

Thr Thr Ala Met Ala Asp Asp Pro Tyr Gly Thr Gly Gln Met Phe
            100                 105                 110

His Leu Asn Thr Ala Leu Thr His Ser Ile Phe Asn Ala Glu Leu Tyr
            115                 120                 125

Ser Pro Glu Ile Pro Leu Ser Thr Asp Gly Pro Tyr Leu Gln Ile Leu
            130                 135                 140

Glu Gln Pro Lys Gln Arg Gly Phe Arg Phe Arg Tyr Val Cys Glu Gly
145                 150                 155                 160

Pro Ser His Gly Gly Leu Pro Gly Ala Ser Ser Glu Lys Asn Lys Lys
            165                 170                 175

Ser Tyr Pro Gln Val Lys Ile Cys Asn Tyr Val Gly Pro Ala Lys Val
            180                 185                 190
```

```
Ile Val Gln Leu Val Thr Asn Gly Lys Asn Ile His Leu His Ala His
            195                 200                 205

Ser Leu Val Gly Lys His Cys Glu Asp Gly Val Cys Thr Val Thr Ala
210                 215                 220

Gly Pro Lys Asp Met Val Gly Phe Ala Asn Leu Gly Ile Leu His
225                 230                 235                 240

Val Thr Lys Lys Val Phe Glu Thr Leu Glu Ala Arg Met Thr Glu
            245                 250                 255

Ala Cys Ile Arg Gly Tyr Asn Pro Gly Leu Leu Val His Ser Asp Leu
            260                 265                 270

Ala Tyr Leu Gln Ala Glu Gly Gly Asp Arg Gln Leu Thr Asp Arg
            275                 280                 285

Glu Lys Glu Ile Ile Arg Gln Ala Ala Val Gln Thr Lys Glu Met
            290                 295                 300

Asp Leu Ser Val Val Arg Leu Met Phe Thr Ala Phe Leu Pro Asp Ser
305                 310                 315                 320

Thr Gly Ser Phe Thr Arg Arg Leu Glu Pro Val Val Ser Asp Ala Ile
            325                 330                 335

Tyr Asp Ser Lys Ala Pro Asn Ala Ser Asn Leu Lys Ile Val Arg Met
            340                 345                 350

Asp Arg Thr Ala Gly Cys Val Thr Gly Gly Glu Glu Ile Tyr Leu Leu
            355                 360                 365

Cys Asp Lys Val Gln Lys Asp Asp Ile Gln Ile Arg Phe Tyr Glu Glu
            370                 375                 380

Glu Glu Asn Gly Gly Val Trp Glu Gly Phe Gly Asp Phe Ser Pro Thr
385                 390                 395                 400

Asp Val His Arg Gln Phe Ala Ile Val Phe Lys Thr Pro Lys Tyr Lys
            405                 410                 415

Asp Val Asn Ile Thr
            420

(2) INFORMATION FOR SEQ ID NO: 114:

(i) SEQUENCE CHARACTERISTICS:
        (A) LENGTH: 391 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 114:

Met Arg Gln Arg Ile Thr Leu Lys Asp Tyr Ala Met Arg Phe Gly Gln
1               5                   10                  15

Thr Lys Thr Ala Lys Asp Leu Gly Val Tyr Gln Ser Ala Ile Asn Lys
            20                  25                  30

Ala Ile His Ala Gly Arg Lys Ile Phe Leu Thr Ile Asn Ala Asp Gly
            35                  40                  45

Ser Val Tyr Ala Glu Glu Val Lys Pro Phe Pro Ser Asn Lys Lys Thr
            50                  55                  60

Thr Ala Met Ala Glu Asp Asp Pro Tyr Leu Gly Arg Pro Glu Gln Met
65                  70                  75                  80

Phe His Leu Asp Pro Ser Leu Thr His Thr Ile Phe Asn Pro Glu Val
```

```
                85                  90                  95
Phe Gln Pro Gln Met Ala Leu Pro Thr Ala Asp Gly Pro Tyr Leu Gln
            100                 105                 110

Ile Leu Glu Gln Pro Lys Gln Arg Gly Phe Arg Phe Arg Tyr Val Cys
            115                 120                 125

Glu Gly Pro Ser His Gly Gly Leu Pro Gly Ala Ser Ser Glu Lys Asn
            130                 135                 140

Lys Lys Ser Tyr Pro Gln Val Lys Ile Cys Asn Tyr Val Gly Pro Ala
145                 150                 155                 160

Lys Val Ile Val Gln Leu Val Thr Asn Gly Lys Asn Ile His Leu His
                165                 170                 175

Ala His Ser Leu Val Gly Lys His Cys Glu Asp Gly Ile Cys Thr Val
            180                 185                 190

Thr Ala Gly Pro Glu Asp Cys Val His Gly Phe Ala Asn Leu Gly Ile
            195                 200                 205

Leu His Val Thr Lys Lys Lys Val Phe Glu Thr Leu Glu Ala Arg Met
            210                 215                 220

Thr Glu Ala Cys Ile Arg Gly Tyr Asn Pro Gly Leu Leu Val His Pro
225                 230                 235                 240

Asp Leu Ala Tyr Leu Gln Ala Glu Gly Gly Gly Asp Arg Gln Leu Gly
                245                 250                 255

Asp Arg Glu Lys Glu Leu Ile Arg Gln Ala Ala Leu Gln Gln Thr Lys
            260                 265                 270

Glu Met Asp Leu Ser Val Val Arg Leu Met Phe Thr Ala Phe Leu Pro
            275                 280                 285

Asp Ser Thr Gly Ser Phe Thr Arg Arg Leu Glu Pro Val Val Ser Asp
290                 295                 300

Ala Ile Tyr Asp Ser Lys Ala Pro Asn Ala Ser Asn Leu Lys Ile Val
305                 310                 315                 320

Arg Met Asp Arg Thr Ala Gly Cys Val Thr Gly Gly Glu Glu Ile Tyr
            325                 330                 335

Leu Leu Cys Asp Lys Val Gln Lys Asp Asp Ile Gln Ile Arg Phe Tyr
            340                 345                 350

Glu Glu Glu Glu Asn Gly Gly Val Trp Glu Gly Phe Gly Asp Phe Ser
            355                 360                 365

Pro Thr Asp Val His Arg Gln Phe Ala Ile Val Phe Lys Thr Pro Lys
            370                 375                 380

Tyr Lys Asp Ile Asn Ile Thr
385                 390

(2) INFORMATION FOR SEQ ID NO: 115:

(i) SEQUENCE CHARACTERISTICS:
        (A) LENGTH: 391 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 115:

Met Glu Gln Glu Ile Thr Leu Lys Asp Tyr Ala Met Arg Phe Gly Gln
1               5                   10                  15
```

Thr Lys Thr Ala Lys Asp Leu Gly Val Tyr Gln Ser Ala Ile Asn Lys
            20                  25                  30

Ala Ile His Ala Gly Arg Lys Ile Phe Leu Thr Ile Asn Ala Asp Gly
        35                  40                  45

Ser Val Tyr Ala Glu Glu Val Lys Pro Phe Pro Ser Asn Lys Lys Thr
    50                  55                  60

Thr Ala Met Ala Glu Asp Pro Tyr Leu Gly Arg Pro Glu Gln Met
65                  70                  75                  80

Phe His Leu Asp Pro Ser Leu Thr His Thr Ile Phe Asn Pro Glu Val
                85                  90                  95

Phe Gln Pro Gln Met Ala Leu Pro Thr Ala Asp Gly Pro Tyr Leu Gln
            100                 105                 110

Ile Leu Glu Gln Pro Lys Gln Arg Gly Phe Arg Phe Arg Tyr Val Cys
        115                 120                 125

Glu Gly Pro Ser His Gly Gly Leu Pro Gly Ala Ser Ser Glu Lys Asn
    130                 135                 140

Lys Lys Ser Tyr Pro Gln Val Lys Ile Cys Asn Tyr Val Gly Pro Ala
145                 150                 155                 160

Lys Val Ile Val Gln Leu Val Thr Asn Gly Lys Asn Ile His Leu His
                165                 170                 175

Ala His Ser Leu Val Gly Lys His Cys Glu Asp Gly Ile Cys Thr Val
            180                 185                 190

Thr Ala Gly Pro Glu Asp Cys Val His Gly Phe Ala Asn Leu Gly Ile
        195                 200                 205

Leu His Val Thr Lys Lys Val Phe Glu Thr Leu Glu Ala Arg Met
    210                 215                 220

Thr Glu Ala Cys Ile Arg Gly Tyr Asn Pro Gly Leu Leu Val His Pro
225                 230                 235                 240

Asp Leu Ala Tyr Leu Gln Ala Glu Gly Gly Gly Asp Arg Gln Leu Gly
                245                 250                 255

Asp Arg Glu Lys Glu Leu Ile Arg Gln Ala Ala Leu Gln Gln Thr Lys
            260                 265                 270

Glu Met Asp Leu Ser Val Val Arg Leu Met Phe Thr Ala Phe Leu Pro
        275                 280                 285

Asp Ser Thr Gly Ser Phe Thr Arg Arg Leu Glu Pro Val Val Ser Asp
    290                 295                 300

Ala Ile Tyr Asp Ser Lys Ala Pro Asn Ala Ser Asn Leu Lys Ile Val
305                 310                 315                 320

Arg Met Asp Arg Thr Ala Gly Cys Val Thr Gly Gly Glu Glu Ile Tyr
                325                 330                 335

Leu Leu Cys Asp Lys Val Gln Lys Asp Asp Ile Gln Ile Arg Phe Tyr
            340                 345                 350

Glu Glu Glu Glu Asn Gly Gly Val Trp Glu Gly Phe Gly Asp Phe Ser
        355                 360                 365

Pro Thr Asp Val His Arg Gln Phe Ala Ile Val Phe Lys Thr Pro Lys
    370                 375                 380

Tyr Lys Asp Ile Asn Ile Thr
385                 390

(2) INFORMATION FOR SEQ ID NO: 116:

(i) SEQUENCE CHARACTERISTICS:
        (A) LENGTH: 241 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 116:

Met Arg Gln Arg Ile Thr Leu Lys Asp Tyr Ala Met Arg Phe Gly Gln
1               5                  10                  15

Thr Lys Thr Ala Lys Asp Leu Gly Val Tyr Gln Ser Ala Ile Asn Lys
            20                  25                  30

Ala Ile His Ala Gly Arg Lys Ile Phe Leu Thr Ile Asn Ala Asp Gly
        35                  40                  45

Ser Val Tyr Ala Glu Glu Val Lys Pro Phe Pro Ser Asn Lys Lys Thr
    50                  55                  60

Thr Ala Ser Asn Lys Lys Thr Thr Ala Gly Asp Pro Gly Lys Lys
65                  70                  75                  80

Gln His Ile Cys His Ile Gln Gly Cys Gly Lys Val Tyr Gly Lys Thr
                85                  90                  95

Ser His Leu Arg Ala His Leu Arg Trp His Thr Gly Glu Arg Pro Phe
            100                 105                 110

Met Cys Thr Trp Ser Tyr Cys Gly Lys Arg Phe Thr Arg Ser Asp Glu
        115                 120                 125

Leu Gln Arg His Lys Arg Thr His Thr Gly Glu Lys Lys Phe Ala Cys
130                 135                 140

Pro Glu Cys Pro Lys Arg Phe Met Arg Ser Asp His Leu Ser Lys His
145                 150                 155                 160

Ile Lys Thr His Gln Asn Lys Lys Gly Gly Pro Gly Val Ala Leu Ser
                165                 170                 175

Val Gly Thr Leu Pro Leu Asp Ser Gly Ala Gly Ser Glu Gly Ser Gly
            180                 185                 190

Thr Ala Thr Pro Ser Ala Leu Ile Thr Thr Asn Met Val Ala Met Glu
        195                 200                 205

Ala Ile Cys Pro Glu Gly Ile Ala Arg Leu Ala Asn Ser Gly Ile Asn
    210                 215                 220

Val Met Gln Val Ala Asp Leu Gln Ser Ile Asn Ile Ser Gly Asn Gly
225                 230                 235                 240

Phe (2) INFORMATION FOR SEQ ID NO: 117:

(i) SEQUENCE CHARACTERISTICS:
         (A) LENGTH: 10 base pairs
         (B) TYPE: nucleic acid
         (C) STRANDEDNESS: both
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 117:

GGGAMTNYCC                                                    10

(2) INFORMATION FOR SEQ ID NO: 118:

(i) SEQUENCE CHARACTERISTICS:

-continued

```
        (A) LENGTH: 72 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO: 118:

Met Glu Pro Val Asp Pro Arg Leu Glu Pro Trp Lys His Pro Gly Ser
1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
            50                  55                  60

His Gln Ala Ser Leu Ser Lys Gln
65                  70
```